(12) United States Patent
Gallant et al.

(10) Patent No.: US 9,757,057 B2
(45) Date of Patent: Sep. 12, 2017

(54) DRY INSERTION AND ONE-POINT IN VIVO CALIBRATION OF AN OPTICAL ANALYTE SENSOR

(71) Applicant: MEDTRONIC MINIMED, INC., Northridge, CA (US)

(72) Inventors: Stuart L. Gallant, Mission Viejo, CA (US); William H. Markle, Mission Viejo, CA (US); Manouchehr Goharlaee, Encinitas, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 188 days.

(21) Appl. No.: 14/073,661

(22) Filed: Nov. 6, 2013

(65) Prior Publication Data

US 2014/0128694 A1    May 8, 2014

Related U.S. Application Data

(60) Provisional application No. 61/774,355, filed on Mar. 7, 2013, provisional application No. 61/723,745, filed on Nov. 7, 2012.

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/1455* (2013.01); *A61B 5/1459* (2013.01);
(Continued)

(58) Field of Classification Search
CPC . A61B 5/14532; A61B 5/1455; A61B 5/1495; A61B 5/1459; A61B 5/14546
See application file for complete search history.

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

| EP | 1692493 B1 | 4/2010 |
| WO | 2008001091 A1 | 1/2008 |

(Continued)

OTHER PUBLICATIONS

PCT International Search Report and Written Opinion for PCT/US2013/068784 dated Jan. 31, 2014.
(Continued)

*Primary Examiner* — Eric Winakur
(74) *Attorney, Agent, or Firm* — Medtronic Minimed, Inc.

(57) ABSTRACT

Disclosed are embodiments that relate to the deployment of a glucose sensor comprising an optical fiber into a physiological fluid, wherein the optical fiber has disposed along a distal region thereof a chemical indicator system comprising a fluorophore and a glucose binding moiety immobilized within a hydrogel, wherein the components of the chemical indicator system are in a dry state before deployment. Also disclosed is a one-point in vivo calibration of the chemical indicator system based on an independently measured glucose concentration.

16 Claims, 41 Drawing Sheets

(51) Int. Cl.
*A61B 5/1459* (2006.01)
*A61B 5/1473* (2006.01)
*A61B 5/1495* (2006.01)

(52) U.S. Cl.
CPC ........ *A61B 5/1495* (2013.01); *A61B 5/14735* (2013.01); *A61B 5/14539* (2013.01); *A61B 2562/043* (2013.01); *A61B 2562/223* (2013.01)

(56) References Cited

U.S. PATENT DOCUMENTS

| | | | |
|---|---|---|---|
| 5,485,408 | A | 1/1996 | Blomquist |
| 5,522,803 | A | 6/1996 | Teissen-Simony |
| 5,624,537 | A | 4/1997 | Turner et al. |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,232,609 | B1* | 5/2001 | Snyder ............... A61B 5/14532 250/459.1 |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,178,676 | B2 | 5/2012 | Gamsey et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 2005/0113658 | A1* | 5/2005 | Jacobson ............ A61B 5/14532 600/316 |
| 2007/0123819 | A1 | 5/2007 | Mernoe et al. |
| 2007/0128681 | A1* | 6/2007 | Barman ............... B01J 13/0091 435/14 |
| 2009/0149656 | A1* | 6/2009 | Singaram ................. B82Y 5/00 546/268.1 |
| 2009/0242425 | A1 | 10/2009 | Kamath et al. |
| 2009/0264719 | A1 | 10/2009 | Markle et al. |
| 2010/0160861 | A1 | 6/2010 | Causey, III et al. |
| 2011/0224516 | A1 | 9/2011 | Romey et al. |

FOREIGN PATENT DOCUMENTS

| | | |
|---|---|---|
| WO | 2012012135 A2 | 1/2012 |
| WO | 2012012135 A3 | 1/2012 |

OTHER PUBLICATIONS

Extended European Search Report for Application No. 13852944.1 dated Jun. 17, 2016.

Vilozny, Boaz et al., "Multiwell Plates Loaded with Fluorescent Hydrogel Sensors for Measuring pH and Glucose Concentration," Journal of Materials Chemistry, vol. 21, No. 21, Jan. 1, 2011, p. 7589.

Muscatello, Michelle M. Ward et al., "Polymerized Crystalline Colloidal Array Sensing of High Glucose Concentrations," Analytical Chemistry, American Chemical Society, USA, vol. 81, No. 12, Jun. 15, 2009, pp. 4978-4986.

\* cited by examiner

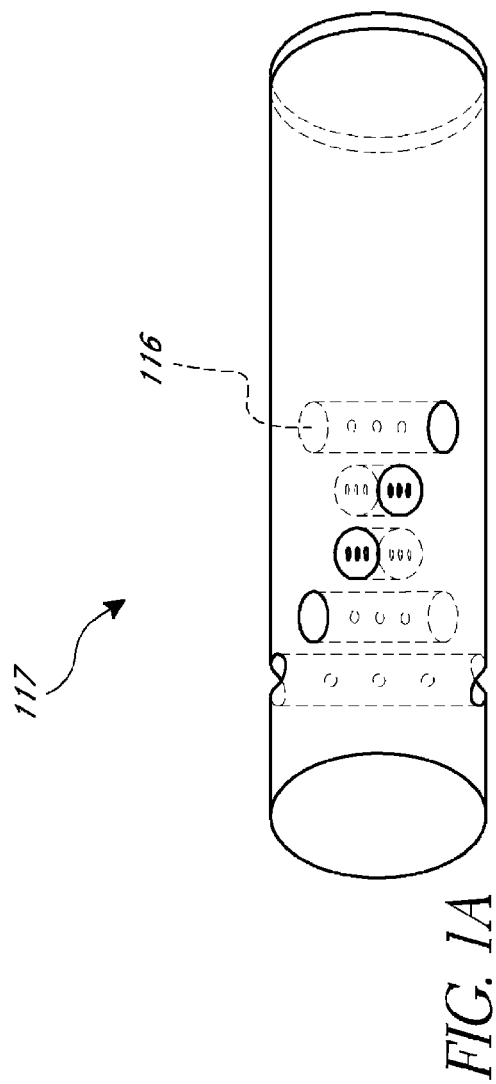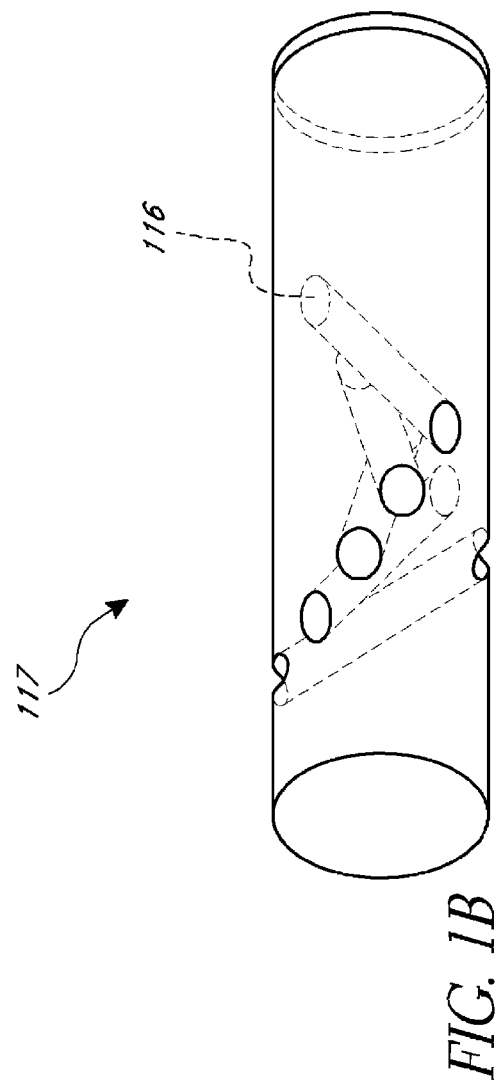
FIG. 1A
FIG. 1B

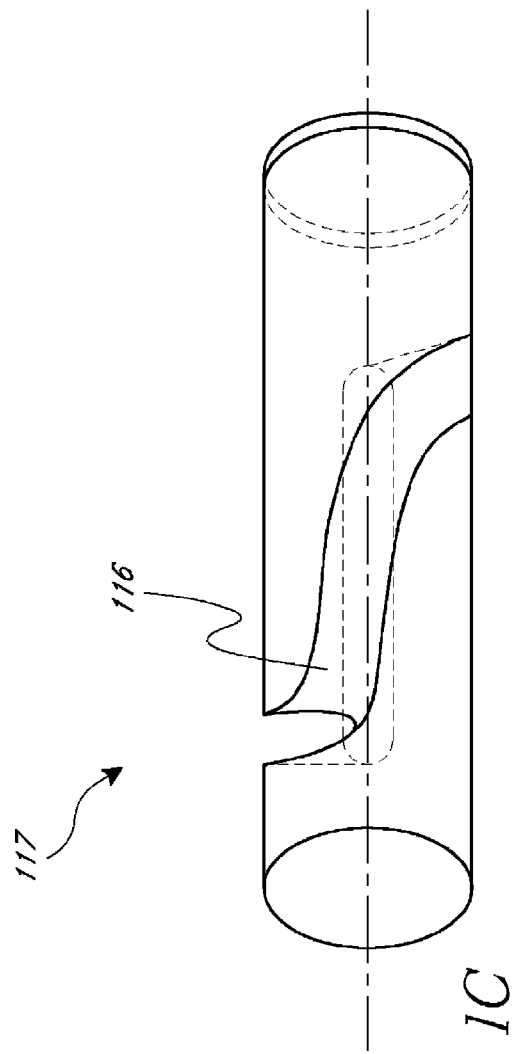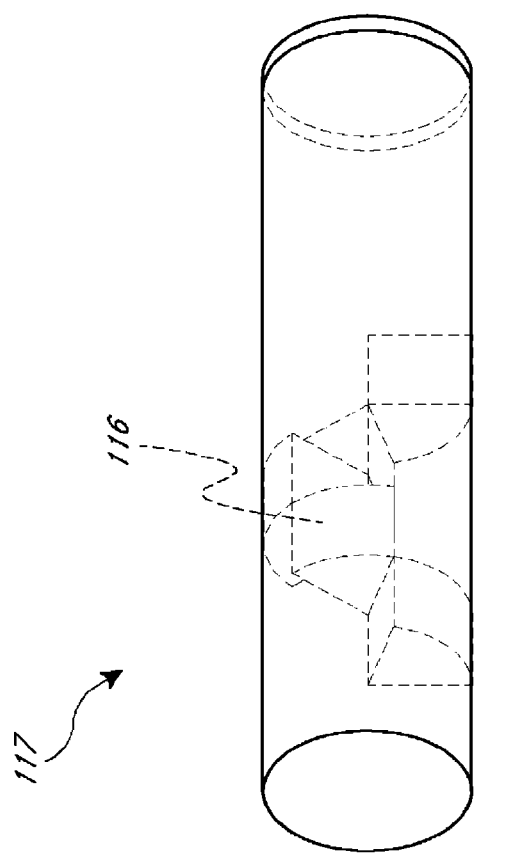
FIG. 1C
FIG. 1D

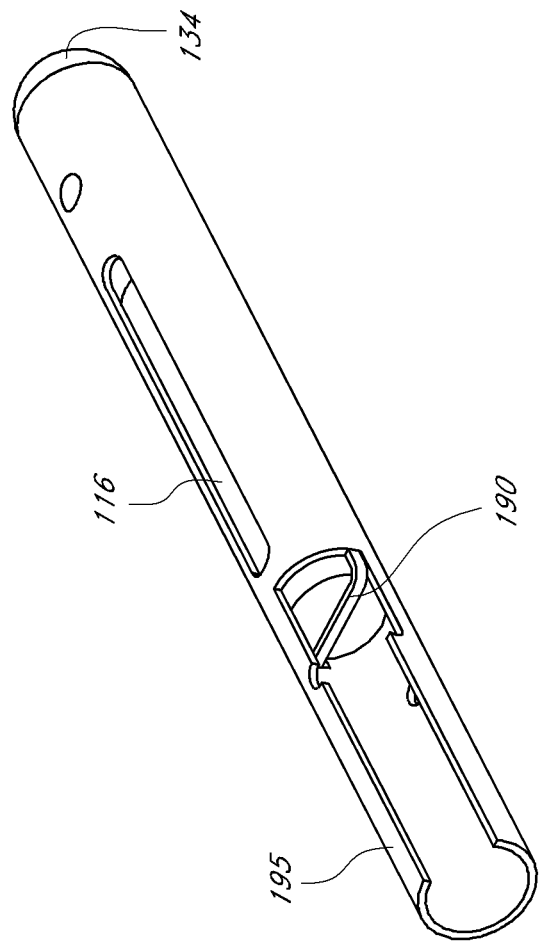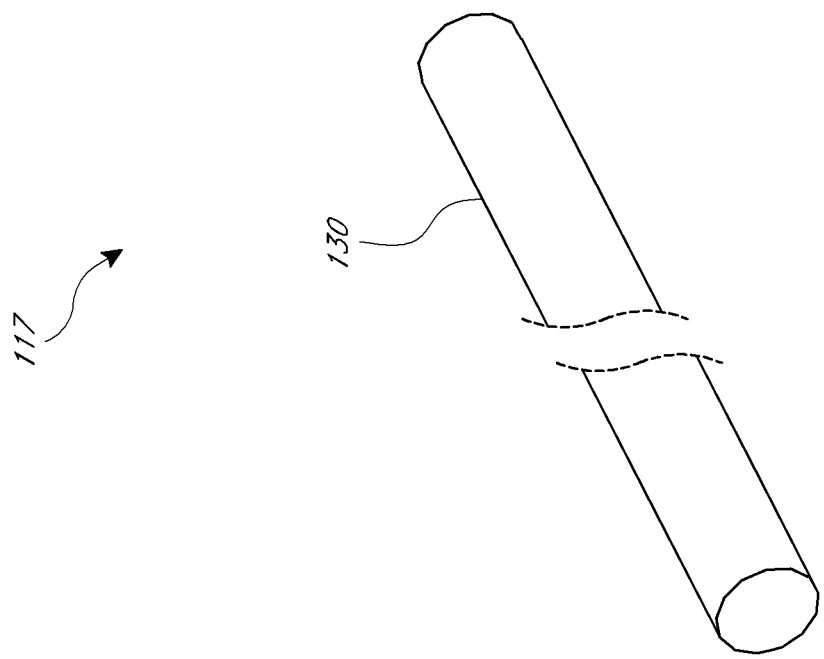
FIG. 8

DRY INSERTION AND ONE-POINT IN VIVO CALIBRATION OF AN OPTICAL ANALYTE SENSOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

Disclosed herein are methods and algorithms for calibrating an optical analyte sensor in vivo.

Description of the Related Art

Analyte sensors, such as glucose sensors, for detecting and measuring the presence of different chemical species in samples are well known. To assure analyte measurement accuracy, whether as a gauge of the amount of analyte present or to agree with a measurement made by another instrument, an analyte sensor generally requires calibration. Such calibration is frequently necessary to account for sensor-to-sensor variation and for differences in the environment where the sensor will be placed.

Current sensor calibration can be time-consuming, uncomfortable, and intrusive for a patient, requiring multiple blood draws or constant sampling for ex-vivo analysis of blood sugar concentration to compare to a signal comprising the output of the analyte sensor. In cases where the sensor output is not linear when compared to the concentration of analyte, or only linear for a range of concentrations, additional complexity and potential uncertainty arises, requiring greater attention, more time, and more difficulty in performing a reliable calibration.

In addition, analyte measurements of the same sample taken by different methodologies may result in different concentrations of analyte being reported. These differences in concentrations reported for the same sample may be due to differences in the analytical technique, differences in sample preparation, or for other reasons as well. For example, some analyte measurement techniques dilute a sample of blood prior to determining the analyte level in solution, while other techniques simply determine the analyte level on a non-diluted sample of blood. In some instances, such dilution can result in additional analyte being extracted from cells present in the blood sample, resulting in a change in the amount of analyte that would be reported by the different methods. Other changes in technique can also result in shifts in reported values, such as when samples are filtered or centrifuged as a part of the procedure, or when a sensor based on a different technology is used. In some instances, problems can occur when measurements for a patient are made by one methodology, and the treatment protocol had been determined based on another methodology.

Because of the above problems, calibration of some sensors has been performed outside of a patient's blood stream. While providing for less discomfort to a patient, calibration outside of a patient's body may not be as accurate as calibration inside a patient's blood stream, where the sensor could take into account the physiological conditions of the patient. Errors in calibration of analyte sensors can lead to erroneous measurements. Reliance on such erroneous measurements, such as for medical treatment, or a mismatch between analytical technique and treatment protocol can lead to adverse responses and possibly life-threatening situations. In view of the foregoing, there is a need for improved methods for calibration of analyte sensors in vivo while minimizing the inconveniences for the patient.

SUMMARY

A method for monitoring glucose concentration in a physiological fluid in a patient is disclosed. The method comprises: immobilizing an equilibrium fluorescence chemical indicator in a hydrogel disposed along a distal region of an optical fiber; drying the immobilized chemical indicator system; deploying the distal region of the optical fiber in the physiological fluid, wherein the hydrogel with immobilized chemical indicator system is deployed in a dry state; allowing the hydrogel with immobilized chemical indicator system to hydrate in the physiological fluid; performing an in vivo calibration of the chemical indicator system against an independently measured glucose concentration, and optionally pH levels, in the physiological fluid; and monitoring the glucose concentration in the physiological fluid.

In one embodiment, the chemical indicator system comprises a fluorophore having acid and base forms. The pH of the physiological fluid may be estimated based on a ratio of fluorescent emissions from the acid and base forms of the fluorophore. The in vivo calibration may be corrected based on the estimated pH of the physiological fluid.

In one embodiment, the method further comprises measuring the temperature of the physiological fluid. The in vivo calibration may be corrected based on the measured temperature of the physiological fluid.

In some embodiments of the method, the hydrogel is hydrated for at least about 10 minutes. In other embodiments, the hydrogel is hydrated for approximately 1-2 hours.

In one embodiment of the method, the in vivo calibration comprises applying the equation:

$$G = M^* \mathrm{Ln}(\mathrm{Glu}) + B$$

wherein G is a fluorescence intensity of the chemical indicator system, Glu is the glucose concentration in the physiological fluid, M is the slope of the straight line approximation at calibration, and B is the intercept of the straight line approximation at calibration; and wherein G is adjusted by a calibration factor to take into account pH using the equation $$CALglu = \frac{Glucal}{\exp(\mathrm{Ln}(glucalc))}$$

wherein CALgul is the calibration factor and Glucal is the value of the independently measured glucose concentration the physiological sample.

A glucose sensor is disclosed in accordance with an embodiment. The sensor comprises an optical fiber comprising an equilibrium fluorescence chemical indicator system immobilized within a hydrogel disposed along a distal end region of the optical fiber, wherein the immobilized chemical indicator system is in a dry state, and an optical coupling disposed along a proximal end region of the optical fiber.

BRIEF DESCRIPTION OF THE DRAWINGS

FIG. 1A shows a glucose sensor having a series of holes that form a helical configuration.

FIG. 1B shows a glucose sensor having a series of holes drilled or formed at an angle.

FIG. 1C shows a glucose sensor having at least one spiral groove.

FIG. 1D shows a glucose sensor having a series of triangular wedge cut-outs.

FIG. 8 shows a cross-sectional view of another embodiment of a glucose sensor having a cavity in a distal portion of the sensor enclosed within a cage and a reference material as a bar extending across the diameter of the cage.

DETAILED DESCRIPTION

Figure 2A:
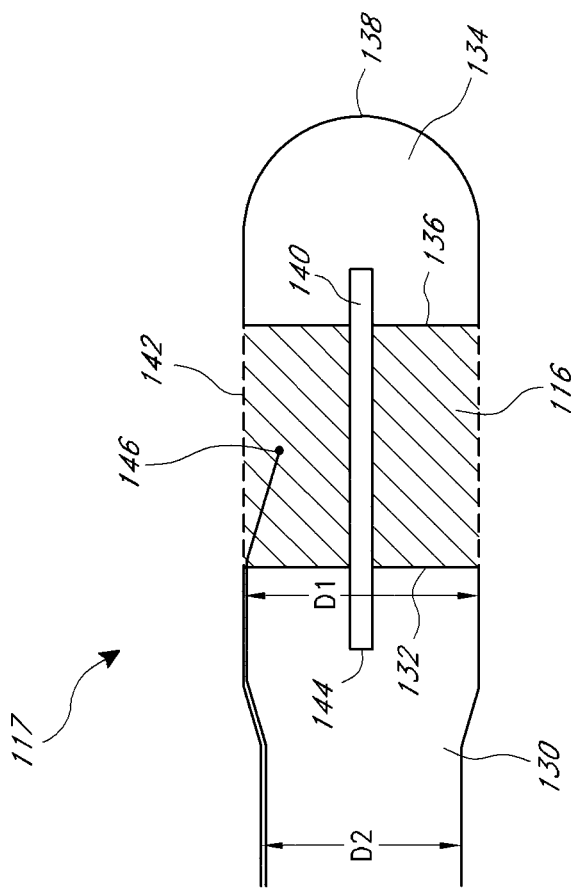
FIG. 2A shows a cross-sectional view of one embodiment of a glucose sensor having a cavity in the distal portion of the sensor and a temperature probe.

The following description and examples illustrate some embodiments of the disclosure in detail. Those of skill in the art will recognize that there are numerous variations and modifications of this disclosure that are encompassed by its scope. Accordingly, the description of a certain exemplary embodiment should not be deemed to limit the scope of the present disclosure.

Disclosed herein are methods of calibrating an analyte sensor capable of measuring the concentration of an analyte. The methods of calibrating can be used on various systems that are configured to measure the concentration of an analyte, such as a fluorescent based system, lifetime chemistry based system, electrochemical system, and other systems known in the art. In various embodiments, the calibration can be used with the sensor to determine the amount of analyte present, or the amount that another method or instrument would determine to be present, and in some embodiments to display the analyte concentration on a computer screen, display the analyte concentration on an instrument screen, record the analyte concentration on paper or computer readable medium, transmit the concentration to another device, or determine an amount of medication to deliver and to deliver the medication to the patient. In some embodiments, the calibration methods are used for calibrating a glucose sensor which in turn is used in conjunction with a glucose delivery device to achieve tight glycemic control over a patient's blood glucose level. In some preferred embodiments, the method of calibration can be used to relate readings made by a sensor being calibrated to readings made by another method, technique, or sensor which is sufficiently linear, or linearizable to provide acceptable agreement over a range of analyte concentrations of interest.

In some embodiments, the methods disclosed herein can be used to calibrate an optical sensor wherein a light-sensitive compound having or being bound to or functionally interacting with an analyte binding moiety which modifies the emitted, absorbed, or reflected spectrum or intensity of light in a reproducible and reversible fashion in response to changes in the amount of analyte bound to the binding moiety. In some embodiments, the amount of emitted light can increase or decrease, or a different wavelength can be detected after incident light interacts with the sensor, such as is described in U.S. Pat. Nos. 5,137,833, 5,512,246, 5,503,770, 6,304,766, 6,766,183, and 6,804,544, and U.S. patent application Ser. Nos. 11/671,880, 12/027,158, 11/671,880, 12/027,158, 12/172,059, 12/118,401, and 11/782,553, incorporated by reference herein in their entireties.

In some embodiments, a functionalized dye can be used which can include a boronic acid or arsenious acid or germanic acid group. In some embodiments, a fluorescent dye can be combined with an amine nitrogen quenching functionality and derivatized boronic, germanic, or arsenious acid in a single complex. In some embodiments, a derivatized boronic, germanic, or arsenious acid can be capable of binding to an analyte of interest. Particular analytes of interest can include those having multiple hydroxyl groups especially vicinal hydroxyl groups and can be carbohydrates such as simple sugars (for example, glucose). Preferred derivatives of boronic, germanic, or arsenious acid include those capable of binding to an analyte will depend upon the analyte of interest, and for analytes having vicinal hydroxyl groups can include aryl or more preferably, a phenyl group.

In some embodiments, increasing analyte concentrations can result in increases in the amount of light of particular wavelengths that can be detected by a receiver associated with a sensor. In some embodiments, increasing analyte concentrations can result in decreases in the amount of light of particular wavelengths that can be detected by a receiver associated with a sensor. In some embodiments, increases in the concentration of analyte can result in increases in the amount of light of one wavelength that can be detected by a receiver associated with a sensor and decreases in the amount of light of another wavelength that can be detected by a receiver associated with a sensor.

In some embodiments, the methods described herein can be applied to fluorescence-based analyte sensors which produce a fluorescent response in relation to a change in analyte concentration that the sensor is exposed to. Suitable analyte sensors include analyte sensors having a polymeric external surface on at least a portion of the sensor. Polymeric materials that can be utilized as a portion of the external surface include hydrophobic polymers such as polyolefin (for example polyethylene and polypropylene), polycarbonate, polysulfone, and fluorocarbons. Sensors can be constructed in various ways, appropriate to the sensing chemistry/technique that is utilized by the sensor. In one embodiment of an optical sensor, such as a sensor producing a fluorescent response in relation to the analyte concentration to which the sensor is exposed, the optical sensor can have a porous polymeric outer surface for a portion of the sensor assembly. Such sensors are described in, for example, U.S. patent application Ser. No. 12/026,396, to Markle, et al., incorporated herein by reference in its entirety.

In some embodiments, a sensor can include an insoluble polymeric matrix immobilizing the chemical indicator system, wherein the polymer matrix is sufficiently permeable to analytes of interest. Suitable polymeric matrix materials include those related to acrylic polymers. In some embodiments, fluorophores and/or binders/quenchers can be incorporated into the polymeric matrix.

Current analyte sensors on the market using hydrogel polymer matrices are typically stored as "wet" sensors, where the hydrogel is stored in a sterile liquid. This can lead to concerns with packaging and storing the sensor, where the liquid could potentially leak, or the sterility of the sensor could be compromised. Thus, in accordance with one embodiment, the polymer matrix, with associated chemical indicator system, is dried and stored in a sterile dry state—which is hydrated in situ once deployed within a patient (e.g., in blood or interstitial fluid). In some embodiments, the sensor can be factory calibrated before drying.

In one embodiment, a method for monitoring glucose in a physiological fluid is disclosed. The method involves preparing an equilibrium, non-consuming, fluorescence, optical glucose sensor as described in e.g., US 2011/0105866 A1. The sensor is optionally calibrated against a solution comprising a known glucose concentration at a known pH and a known temperature (see e.g., US 2011/0224516 A). The calibration data, e.g., mathematical model of the line that describes the relationship between fluorescence and glucose at a given pH and temperature may be stored for later use as 'factory calibration' data. The sensor is then dried (e.g., in air for about 1 hour at room temperature; of course other drying conditions may also be used) and sterilized (e.g., using EtO as is known in the art) for stable storage, packaging, shipping, etc. Once at the site of use, e.g., an ICU for critically ill patients, the sensor is deployed, while still in the dry state, within the physiological fluid in the patient (e.g., within a blood vessel or subcutaneously). Uniquely, by employing the disclosed dry insertion method(s), there is no need to use a calibration chamber, in which the 'wet' chemistry is exposed to one or more solutions having known glucose concentrations immediately before deployment, often at one or more controlled temperatures. The sensing chemistry hydrates in vivo and a one-point in vivo calibration is performed. The fluorescence emission of the sensor is calibrated against an independently measured glucose concentration in the physiological fluid, e.g, YSI laboratory analyzer. In some embodiments, the sensor chemistry comprises a fluorescent dye that exhibits two forms that change with pH, wherein the two forms are characterized by two different fluorescent emissions—thereby enabling ratiometric estimation of pH (see e.g., U.S. Pat. No. 7,751,863). In some embodiments, the sensor comprises a temperature detector (e.g., thermister or thermocouple). In one embodiment, the in vivo calibration comprises calibrating the fluorescence emission(s) against an independently measured glucose concentration, and correcting for the estimated pH and the detected temperature of the physiological fluid (without a pre-deployment 'wet' calibration or the need for any ex vivo calibration).

Analyte Sensors

With reference to FIGS. 1A-D, certain prior art embodiments (see US Patent Publication No. 2008/0188725) are illustrated. The glucose sensor 117 in FIG. 1A is an optical fiber with a series holes 116 drilled straight through the sides of the optical fiber. In certain embodiments, the holes 116 are filled with one or more glucose-sensing chemical indicator systems. These holes may be covered with a selectively permeable membrane, wherein the permeability is selected such that the molecules of the chemical indicator system (e.g., fluorophore and quencher) are retained within the cavities, whereas glucose is freely permeable. In certain embodiments, the series of holes 116 that are drilled through the glucose sensor 117 are evenly spaced horizontally and evenly rotated around the sides of the glucose sensor 117 to form a spiral or helical configuration. In certain embodiments, the series of holes are drilled through the diameter of the glucose sensor.

With reference to FIG. 1B, in certain embodiments, the glucose sensor 117 is a solid optical fiber with a series of holes 116 drilled through the sides of the fiber at an angle. In certain embodiments, the series of holes drilled at an angle, which are filled with hydrogel/chemical indicator system, are evenly spaced horizontally and evenly rotated around the sides the glucose sensor 117. With reference to FIG. 1C, in certain embodiments, the optical fiber comprises a groove 116 along the length of the optical fiber, wherein the groove is filled with hydrogel/chemical indicator system. In certain embodiments, the depth of the groove extends to the center of the optical fiber. In certain embodiments, the groove spirals around the optical fiber. In certain embodiments, the groove spirals around the optical fiber to complete at least one rotation. In certain embodiments, the groove spirals around the optical fiber to complete multiple rotations around the optical fiber.

With reference to FIG. 1D, in certain embodiments, the glucose sensor 117 is a solid optical fiber with triangular wedges 116 cut from the fiber. In certain embodiments, the triangular wedge areas are filled with hydrogel/chemical indicator system. In certain embodiments, the triangular wedges cut-outs are evenly spaced horizontally and around the sides of the glucose sensor 117. In certain embodiments, all light traveling in the glucose sensor 117 is transmitted through at least one hole or groove 116 filled with hydrogel/chemical indicator system.

In certain embodiments, as illustrated in FIGS. 2-6, the glucose sensor 117 comprises an optical fiber 130 having a distal end 132, an atraumatic tip portion 134 having a proximal end 136 and a distal end 138, a void or cavity 116 between the distal end 132 of the optical fiber 130 and the proximal end 136 of the atraumatic tip portion 134, and a rod 140 connecting the distal end 132 of the optical fiber 130 to the proximal end 136 of the atraumatic tip portion 134, wherein the rod traverses the void or cavity. In preferred embodiments, molecules of a chemical indicator system are disposed within the void or cavity 116 and immobilized (by covalent bonding or non-covalent interaction) or otherwise associated within hydrogel matrices. See e.g., the chemical indicator systems disclosed in U.S. Pat. Nos. 7,417,164 and 7,470,420. The cavity 116 may be loaded with hydrogel/chemical indicator system by any methods known in the art. In preferred embodiments, the cavity 116 is filled with hydrogel/chemical indicator system in a liquid state. The hydrogel/chemical indicator systems are preferably polymerized in situ, as detailed in co-pending U.S. patent application Ser. No. 12/026,396 (published as 2008/0187655).

In certain embodiments, the rod 140 is attached to the optical fiber 130 and/or atraumatic tip 134 by heating and expanding the optical fiber 130 and atraumatic tip 134 and embedding the rod 140 there between. In certain embodiments, the optical fiber 130 is heated to between about 100° C. and about 160° C., more preferably between about 110° C. and about 140° C. In other embodiments, the optical fiber 130 is first heated and then cooled one or more times. In certain embodiments, the rod 140 is attached to the optical fiber 130 and/or the atraumatic tip 134 by applying an adhesive. In preferred embodiments, the adhesive is biocompatible, such as for example, cyanoacrylates, epoxies, light cure adhesives, silicones, and urethanes. In certain embodiments, after applying the adhesive and joining the rod 140 with the optical fiber 130 and atraumatic tip 134, the adhesive is cured at room temperature, by heating, or by applying UV/visible light. In certain embodiments, the time to fix the rod 140 to the optical fiber 130 and/or atraumatic tip 134 can vary from about 5 seconds to about 60 seconds, from about 15 minutes to about 5 hours, from about 60 seconds to about 10 minutes, or up to about 24 hours.

In some embodiments, the proximal surface of the rod 144 is reflective so that a portion of the excitation light signal (or reference light signal) is reflected proximally down the optical fiber 130 to a detector (not shown). The term rod is used herein to refer to any elongate structural member, regardless of its geometry, configured to connect the atraumatic tip portion to the optical fiber. The rod may be centered coaxially (as illustrated) or off-centered with regard to the cross-section of the fiber and atraumatic tip portion. In some embodiments, there may be more than one rod extending between the fiber and the atraumatic tip portion. Where more than one rod is employed, the rods may be arranged symmetrically or asymmetrically with respect to the cross-section of the fiber and atraumatic tip portion.

Figure 5:
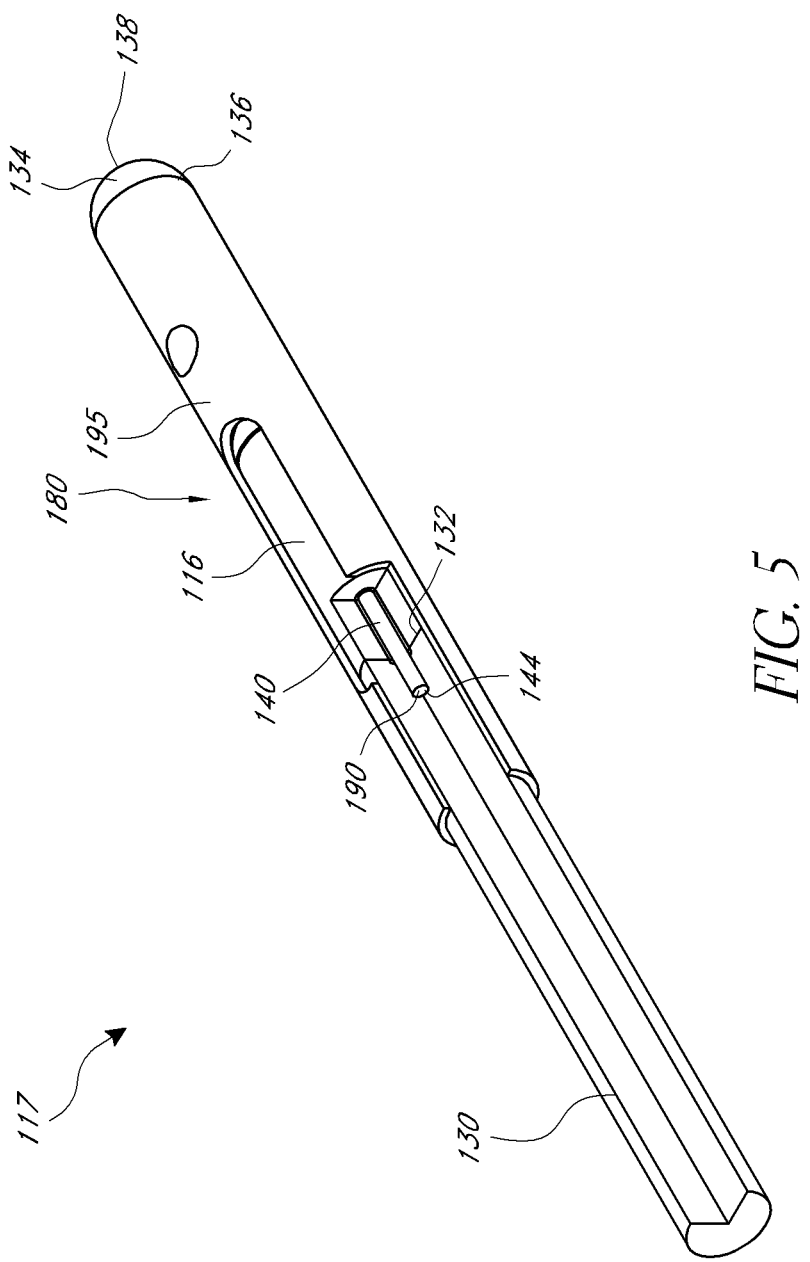
FIG. 5 shows a cross-sectional view of another embodiment of a glucose sensor having a cavity in a distal portion of the sensor enclosed within a cage and an additional reference material.
Figure 6:
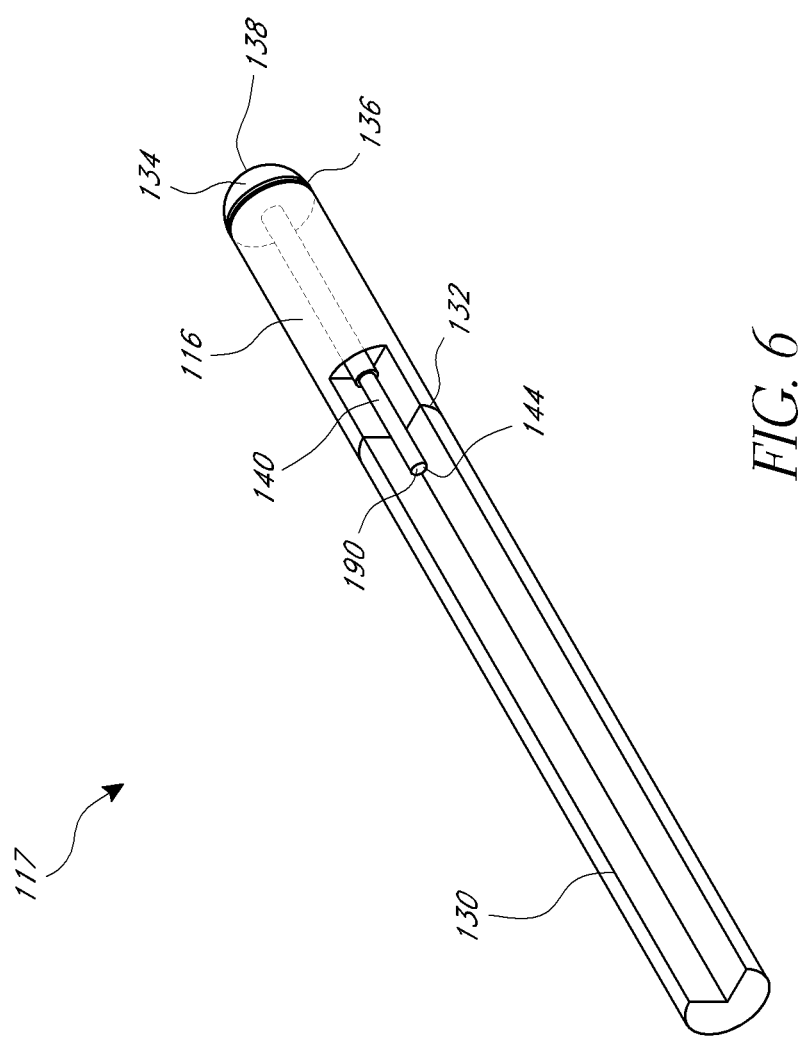
FIG. 6 shows a cross-sectional view of another embodiment of a glucose sensor having a cavity in a distal portion of the sensor and an additional reference material.

In certain embodiments, as illustrated in FIGS. 5 and 6, a reference material 190 may be attached to the proximal surface of the rod 144. The reference material 190 may be reflective (e.g., a mirror) and functions similar to embodiments in which the proximal surface of the rod 144 reflects at least a portion of the excitation light signal (or reference light signal) down the optical fiber 130 to a detector (not shown). In other embodiments, the reference material 190 comprises a separate dye indicator system, such as for example a glucose-insensitve fluorescent dye. The excitation light from the optical fiber 130 causes the glucose-insensitive fluorophore to emit a fluorescent light back to a detector (not shown) in order to reference the emission signal from the hydrogel/chemical indicator system. In certain embodiments, the separate dye indicator system is formed of a plastic material, such as for example polycarbonate, polyethylene, or polystyrene, infused with a fluorescent dye configured to emit a separate glucose-insensitive signal.

The hydrogel and glucose-sensing chemical indicator system is disposed within the cavity 116. In preferred embodiments, the hydrogel/chemical indicator system filled cavity 116 is covered by a selectively permeable membrane 142 that allows passage of glucose into and out of the hydrogel/chemical indicator system. Although these embodiments are described using a glucose sensor 117, it should be understood by a person of ordinary skill in the art that the sensor 117 can be modified to measure other analytes by changing, for example, the sensing chemistry, and if necessary, the selectively permeable membrane 142.

In certain embodiments, the selectively permeable membrane 142 is attached to the optical fiber 130 and the atraumatic tip 134 by means of an adhesive. In preferred embodiments, the adhesive is biocompatible, such as for example, cyanoacrylates, epoxies, light cure adhesives, silicones, and urethanes. In certain embodiments, after applying the adhesive and attaching the selectively permeable membrane 142 to the optical fiber 130 and atraumatic tip 134, the adhesive is cured at room temperature, by heating, or by applying UV/visible light. In certain embodiments, the time to adhere the selectively permeable membrane 142 to the optical fiber 130 and/or atraumatic tip 134 can vary from about 5 seconds to about 60 seconds, from about 15 minutes to about 5 hours, from about 60 seconds to about 10 minutes, or up to about 24 hours. In other embodiments, the selectively permeable membrane 142 is pre-fabricated as a sleeve. The sleeve may be slid into place and sealed using an adhesive and/or heated to form-fit the glucose sensor 117. In certain embodiments, the selectively permeable membrane 142 surrounds the entire circumference of the glucose sensor 117. In other embodiments, the selectively permeable membrane 142 covers a window 180 or opening in the glucose sensor 117 exposing the void or cavity 116 to analytes in the blood stream.

Figure 2B:
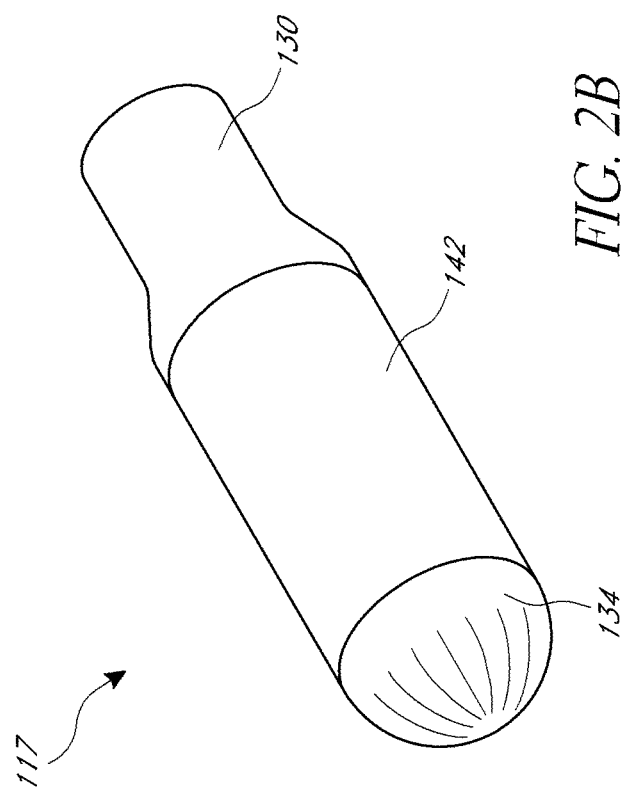
FIG. 2B shows a perspective view of the glucose sensor shown in FIG. 2A.

In some embodiments, as illustrated in FIGS. 2A and 2B, the sensor 117 comprises a distal portion and a proximal portion. The distal portion of the sensor 117 comprises the atraumatic tip portion 134, the hydrogel/chemical indicator system filled cavity 116, the rod 140, at least the portion of the selectively permeable membrane 142 that covers the cavity 116 and the distal end 132 of the optical fiber 130. The proximal portion of the sensor 117 comprises the proximal portion of the optical fiber 130. In some embodiments, the diameter, D1, of the distal portion of the sensor 117 is greater than the diameter, D2, of the proximal portion of the sensor 117. For example, the diameter D1 of the distal portion of the sensor 117 can be between about 0.0080 inches and 0.020 inches, while the diameter D2 of the proximal portion of the sensor 117 can be between about 0.005 inches to 0.015 inches. In some embodiments, the diameter D1 of the distal portion of the sensor 117 is about 0.012 inches, while the diameter D2 of the proximal portion of the sensor 117 is about 0.010 inches.

In some embodiments, the sensor 117, including the selectively permeable membrane 142, has a smooth surface. The smooth surface can be made for example by the method disclosed in co-pending U.S. patent application Ser. No. 12/026,396 (published as 2008/0187655). In summary, one preferred embodiment of the method comprises filling the cavity 116 with a solution comprising a monomer, cross-linker and an initiator, such as a thermal initiator. After the sensor 117 has been filled, the sensor 117 is dipped into liquid wax, which is allowed to harden around the sensor 117 and selectively permeable membrane 142.

The liquid wax has a melting point that is greater than the thermal initiation temperature. Therefore, in order to reduce the likelihood of initiation during the wax dipping and coating step, the filled sensor 117 can be chilled before the wax dipping and coating step. After the sensor 117 has been coated with wax, the solution in the cavity 116 can be deoxygenated by placing the sensor 117 in a water bath while bubbling an inert gas, such as nitrogen, in the bath.

After deoxygenation, polymerization can be initiated by heating the sensor 117 to a temperature above the thermal initiation temperature, but below the melting point of the wax. Once the solution is substantially polymerized into the hydrogel, the wax can be removed from the sensor by use of a solvent, such as hexane, leaving a sensor 117 with a smooth surface.

Figure 3A:
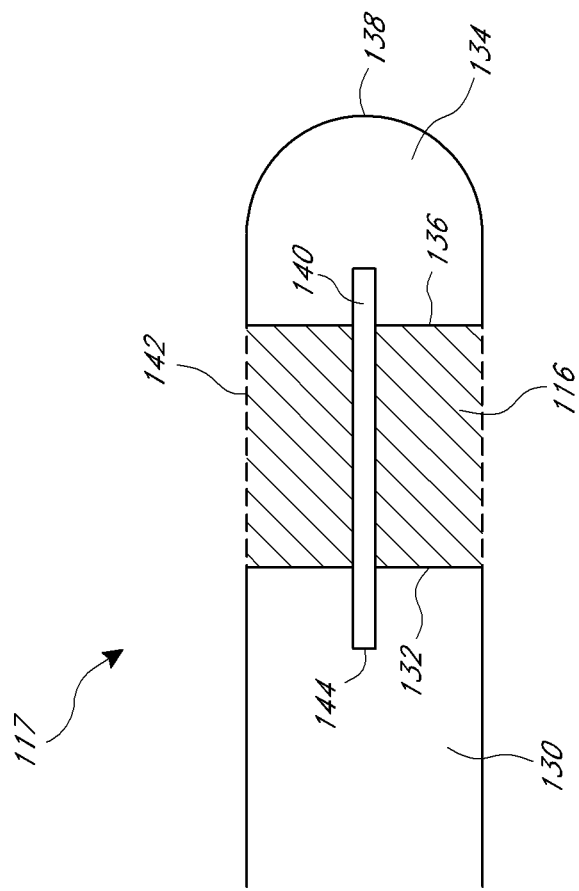
FIG. 3A shows a cross-sectional view of another embodiment of a glucose sensor having a cavity in the distal portion of the sensor.
Figure 3B:
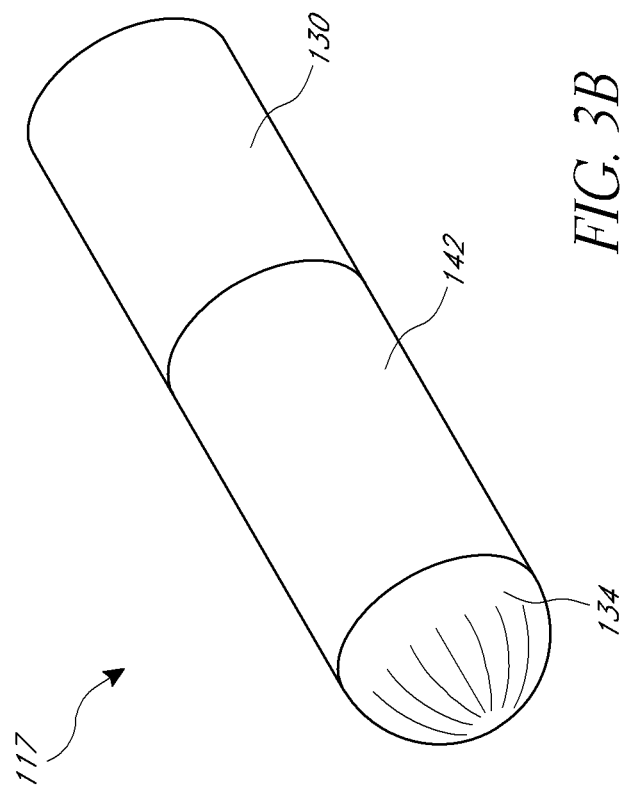
FIG. 3B shows a perspective view of the glucose sensor shown in FIG. 3A.

In some embodiments, as illustrated in FIGS. 3A and 3B, the sensor 117 comprises a distal portion and a proximal portion with substantially the same diameter. In some embodiments, the diameter of the sensor 117 is between about 0.005 inches and 0.020 inches. In other embodiments, the diameter of the sensor 117 is between about 0.008 inches and 0.014 inches. In other embodiments, the diameter of the sensor 117 is about 0.010 inches or about 0.012 inches.

In some embodiments, the rod 140 has a proximal portion that is connected to the distal portion of the optical fiber 130 and a distal portion that is connected to the proximal portion of the atraumatic tip portion 134. The rod 140 can be made of a metal, metal alloy, plastic, polymer, ceramic, composite material or any other material with suitable mechanical properties for connecting the atraumatic tip portion 134 with the distal portion of the optical fiber 130. For example, the rod 140 can be made of stainless steel, titanium or Nitinol. The rod 140 can be cylindrical or noncylindrical, such as a bar with a square, rectangular, oval or oblong cross-section. In some embodiments, the diameter of the rod 140 is generally between about 0.001 to 0.010 inches. In other embodiments, the diameter of the rod 140 is generally between about 0.004 to 0.008 inches. In other embodiments, the diameter of the rod 140 is about 0.001 inches, about 0.002 inches or 0.004 inches. In some embodiments, the diameter of the rod 140 may be less than about 0.001 inches. In some embodiments, the diameter of the rod 140 may be greater than about 0.010 inches. In some embodiments, the length of the rod 140 is generally less than about 0.005 inches. In some embodiments, the length of the rod 140 is between about 0.005 to 0.040 inches. In other embodiments, the length of the rod 140 is generally between about 0.020 to 0.040 inches. In other embodiments, the length of the rod 140 is generally about 0.015 inches. In some embodiments, the length of the rod 140 is generally greater than about 0.005 inches.

The rod 140 adds mechanical stability to the distal portion of the sensor 117. In some embodiments, the rod 140 also adds flexibility to the distal portion of the sensor 117, allowing the atraumatic tip portion 134 to flex back and forth relative to the orientation of the optical fiber 130. The flexibility of the rod 140, and thus the degree which the atraumatic tip portion 134 can flex, can be increased or decreased by decreasing or increasing the diameter of the rod 140. In addition, the flexibility of the rod 140 can be altered by making the rod 140 from a stiff or flexible material.

In some embodiments as illustrated in FIGS. 2A and 3A, a reflective surface 144 is disposed on the proximal end of the rod 140, which is inserted into the optical fiber 130. The reflective surface 144 is capable of reflecting back at least a portion of either reference light or excitation light emitted from the light source. The other end of the rod 140 is inserted into the atraumatic tip portion 134. In certain embodiments, the atraumatic tip portion may be made from a non-reflective material, for example polyethylene (e.g., black polyethylene) or polypropylene. The reference or excitation light that passes though the optical fiber 130 in the region corresponding to the diameter of the rod 140 is reflected off the reflective surface 144 without entering into the hydrogel filled cavity 116; the amount of light entering the hydrogel/chemical indicator system can be controlled by varying the diameter/cross-sectional area of the rod and/or by attaching a mirror or other reflective member 190 (illustrated in FIGS. 5 and 6) having a selected cross-sectional area to the proximal end of the rod. The hydrogel filled cavity 116 is preferably covered by a selectively permeable membrane 142, which is at least permeable to glucose. Therefore, the reflected reference or excitation light and the ratio between the reflected and emitted light is independent of the temperature, pH, glucose concentration, and chemistry formulation of the hydrogel filled cavity 116. The ratio between the reflected and emitted light is dependent, however, on the diameter of the rod and the ratio of the diameter of the rod to the area of the sensor. In certain embodiments, the rod 140 is sufficiently stiff to keep the hydrogel filled cavity 116 in a fixed orientation relative to the optical fiber 130 so that any light that is transmitted through the hydrogel cavity 116 is not reflected back to the optical fiber 130.

With regard to FIG. 3B, there is shown a perspective view of the distal region of the sensor 117 illustrated in FIG. 3A. It can be appreciated in the illustrated embodiment that there is no change in sensor diameter from the optical fiber 130, through the membrane 142 covered hydrogel cavity, until the tapered atraumatic distal tip portion 134.

Figure 4:
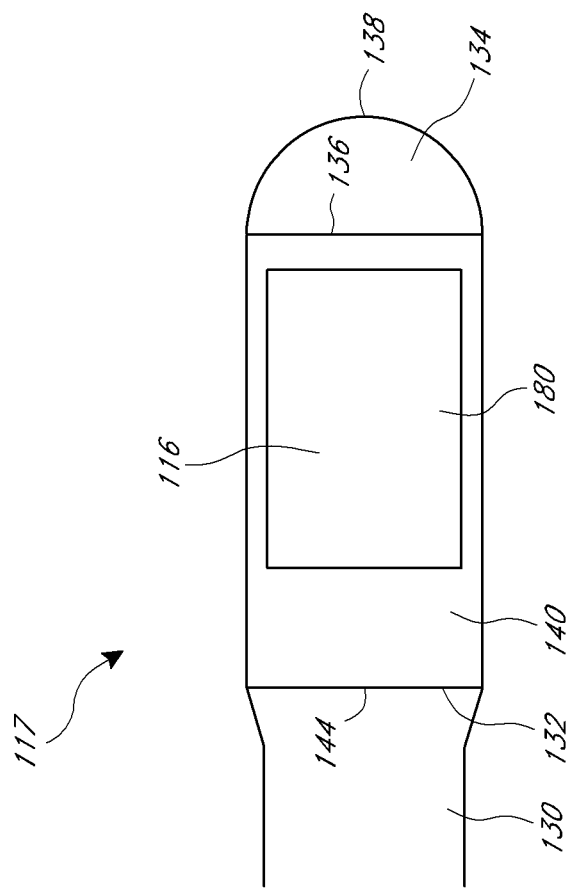
FIG. 4 shows a cross-sectional view of another embodiment of a glucose sensor having a window opening to a cavity in the distal portion of the sensor.

In some embodiments, as shown in FIG. 4, a window 180 is cut into a hypotube 140. The distal end 132 of the optical fiber 130 is inserted onto the reflective surface 144 (e.g., an annular mirror) and then heated such that the optical fiber 130 swells to fully contact the reflective surface 144 of the hypotube 140. In certain embodiments, heating the optical fiber 130 is carried out in a glass tube. In other embodiments, heating the optical fiber 130 is carried out in an oven. In still other embodiments, the optical fiber 130 is attached to the hypotube 140 using an adhesive. In preferred embodiments, the adhesive is biocompatible, such as for example, cyanoacrylates, epoxies, light cure adhesives, silicones, and urethanes. In certain embodiments, after applying the adhesive and attaching the optical fiber 130 to the hypotube 140, the adhesive is cured at room temperature, by heating, or by applying UV/visible light. In certain embodiments, the time to adhere the optical fiber 130 to the hypotube 140 can vary from about 5 seconds to about 60 seconds, from about 15 minutes to about 5 hours, from about 60 seconds to about 10 minutes, or up to about 24 hours. Similar methods may be employed for attaching the hypotube 140 to the atraumatic tip 134. Similar to previous embodiments, the reference or excitation light is reflected off the reflective surface 144 without entering the window 180 that opens to the cavity 116 which is filled with hydrogel/chemical indicator system. Therefore, the reflected reference or excitation light and the ratio between the reflected and emitted lights is independent of the temperature, pH, glucose concentration, and hydrogel chemistry. The surface area of the reflective surface can be varied to control the amount of excitation light that enters the hydrogel/chemical indicator system filed cavity 116. The distal end 136 of the hypotube 140, as in previous embodiments, may have a non-reflective surface, such as a black plug made of polyethylene so that light entering the hydrogel/chemical indicator system filled cavity 116 is not reflected back into the optical fiber 130. In some embodiments, the window 180 containing the hydrogel/chemical indicator system filled cavity 116 is covered by a selectively permeable membrane (not shown).

In some embodiments, as illustrated in FIG. 5, the glucose sensor 117 includes a cage 195, as an outer shell, connecting the atraumatic tip 134 with the optical fiber 130. The cage 195 can add mechanical stability to the distal portion of the sensor 117. In some embodiments, the cage 195 also adds flexibility to the distal portion of the sensor 117, allowing the atraumatic tip portion 134 to flex back and forth relative to the orientation of the optical fiber 130. The flexibility of the cage 195, and thus the degree which the atraumatic tip portion 134 can flex, can be increased or decreased by decreasing or increasing the thickness of the cage 195 walls. In addition, the flexibility of the cage 195 can be altered by making the cage 195 from a stiff or flexible material. In certain embodiments, the thickness of the cage 195 walls is about 0.001 inches, about 0.002 inches, or about 0.004 inches. In some embodiments, the thickness of the cage 195 walls may be less than about 0.001 inches. In some embodiments, the thickness of the cage 195 walls may be greater than about 0.010 inches.

In some embodiments, the diameter of the optical fiber 130 may be smaller than the diameter of the interior of the cage 195, allowing the optical fiber 130 to fit within the interior of the cage 195 and abut the void or cavity 116. For example, the diameter of the optical fiber 130 may be between about 0.005 inches and about 0.020 inches, between about 0.008 inches and about 0.014 inches, or between about 0.010 inches and about 0.012 inches. The diameter of the interior of the cage 195 may be about 0.001 inches larger.

In certain embodiments, the cage 195 has a window or opening 180, covered by a selectively permeable membrane 142 (not shown), which allows for at least the transmission of analytes, such a glucose, into the void or cavity 116. In certain preferred embodiments, the void or cavity 116 is filled with a hydrogel/chemical indicator system. A rod 140 may be positioned within the glucose sensor 117 having a reference material 190. As discussed above, the reference material 190 may be a mirror for reflecting excitation light from the optical fiber 130 back to a detector (not shown) or a glucose-insensitive fluorescent dye for emitting a glucose-insensitive reference signal back to a detector (not shown). The combination of the cage 195 and the rod 140 may provide a sufficiently rigid structure such that the excitation light which enters the void or cavity 116 remains separate from the light that enters the reference material 190.

In some embodiments, as illustrated in FIG. 6, the glucose sensor 117 does not have a cage 195 surrounding the void or cavity 116. Instead, similar to FIGS. 2A and 3A, the rod 140 connects the optical fiber 130 and atraumatic tip 134, providing structure for the glucose sensor 117, and is surrounded by the void or cavity 116, which in turn is covered by a selectively permeable membrane 142. Similar to FIG. 3A, the diameter of the optical fiber 130 is the same as the diameter of the hydrogel/chemical indicator system encased cavity 116. As discussed with respect to FIG. 5, the rod may have a reference material 190 attached to the proximal surface of the rod 144, which functions as previously discussed.

FIGS. 7-11 illustrate certain embodiments having different configurations for the reference material 190. As discussed previously, the reference material 190 in each of these embodiments may either comprise reflective material to return at least a portion of the excitation light back to a detector (not shown) or a separate dye indicator system to return an emission signal back to a detector (not shown). Similar to previous embodiments, the excitation or reference light is reflected off the reflective surface 190 without entering the cavity 116, which is filled with the hydrogel/chemical indicator system. Likewise, the emitted or reference light from the separate dye indicator system is independent of the glucose concentration. Therefore, the reference light and the ratio between the reference light and emitted glucose concentration dependent lights are independent of the temperature, pH, glucose concentration, and hydrogel chemistry. The surface area, shape, and configuration of the reference material 190 can be varied to control the amount of excitation light that enters the hydrogel/chemical indicator system filed cavity 116. The distal end 136 of the rod or hypotube 140, as in previous embodiments, or reference material 190 may have a non-reflective surface, such as a black plug made of polyethylene so that light entering the hydrogel/chemical indicator system filled cavity 116 is not reflected back into the optical fiber 130.

Figure 7:
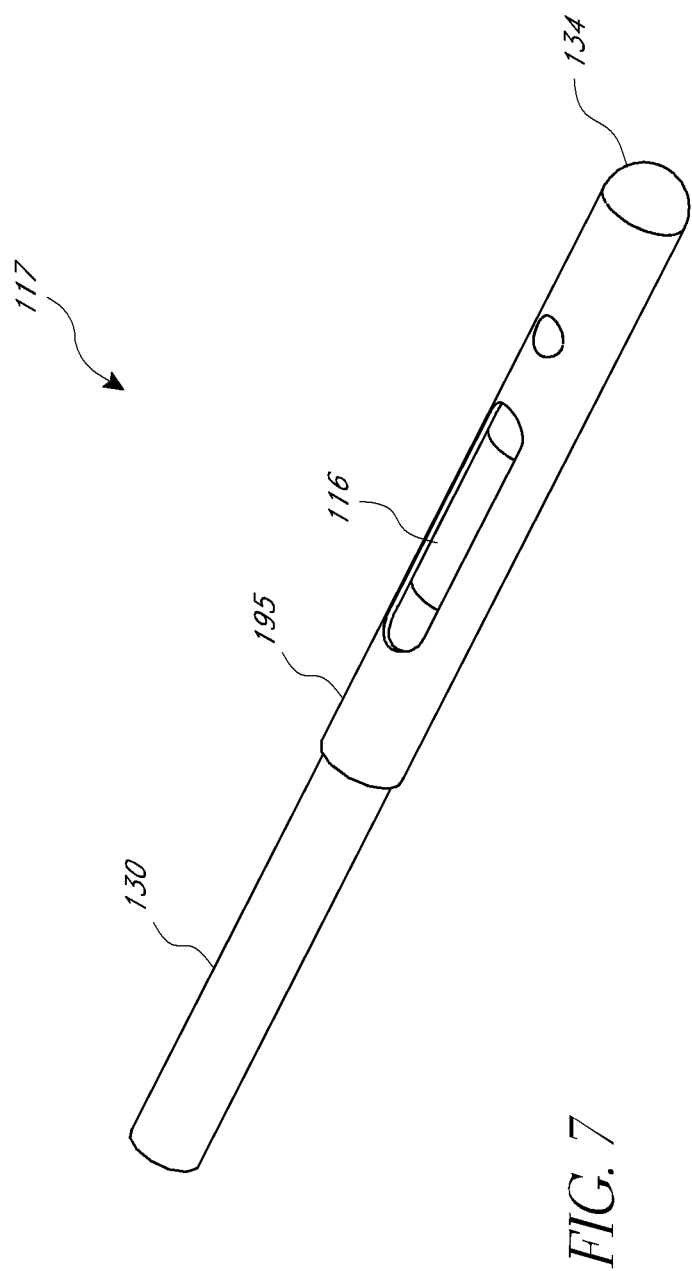
FIG. 7 shows a cross-sectional view of another embodiment of a glucose sensor having a cavity in a distal portion of the sensor enclosed within a cage and a reference material extending to the atraumatic tip.

In FIG. 7, the reference material 190 abuts the void or cavity 116 beneath the cage 195 and extends to and comprises the atraumatic tip 134. In certain embodiments, the atraumatic tip 134 is formed of a glucose-insensitive red dye plastic material. In FIG. 8, the reference material 190 is a reflective strip that spans the diameter of the hydrogel-filled cavity 116. The term reflective strip is used herein to refer to any elongate member, regardless of its geometry, width, or thickness that spans at least a cross-section of the glucose sensor 117. The reflective strip 190 may be centered at the diameter of the glucose sensor 117 (as illustrated) or off-centered with regard to the cross-section of the cage 195 or optical fiber 130. In some embodiments, there may be more than one reflective strip in one or more locations within the glucose sensor 117. Where more than one reflective strip is employed, the reflective strip may be arranged symmetrically or asymmetrically with respect to the cross-section of the glucose sensor 117. In certain embodiments, the reflective strip 190 may be between about 0.001 inches and about 0.005 inches wide and between about 0.001 inches and about 0.005 inches thick.

Figure 9:
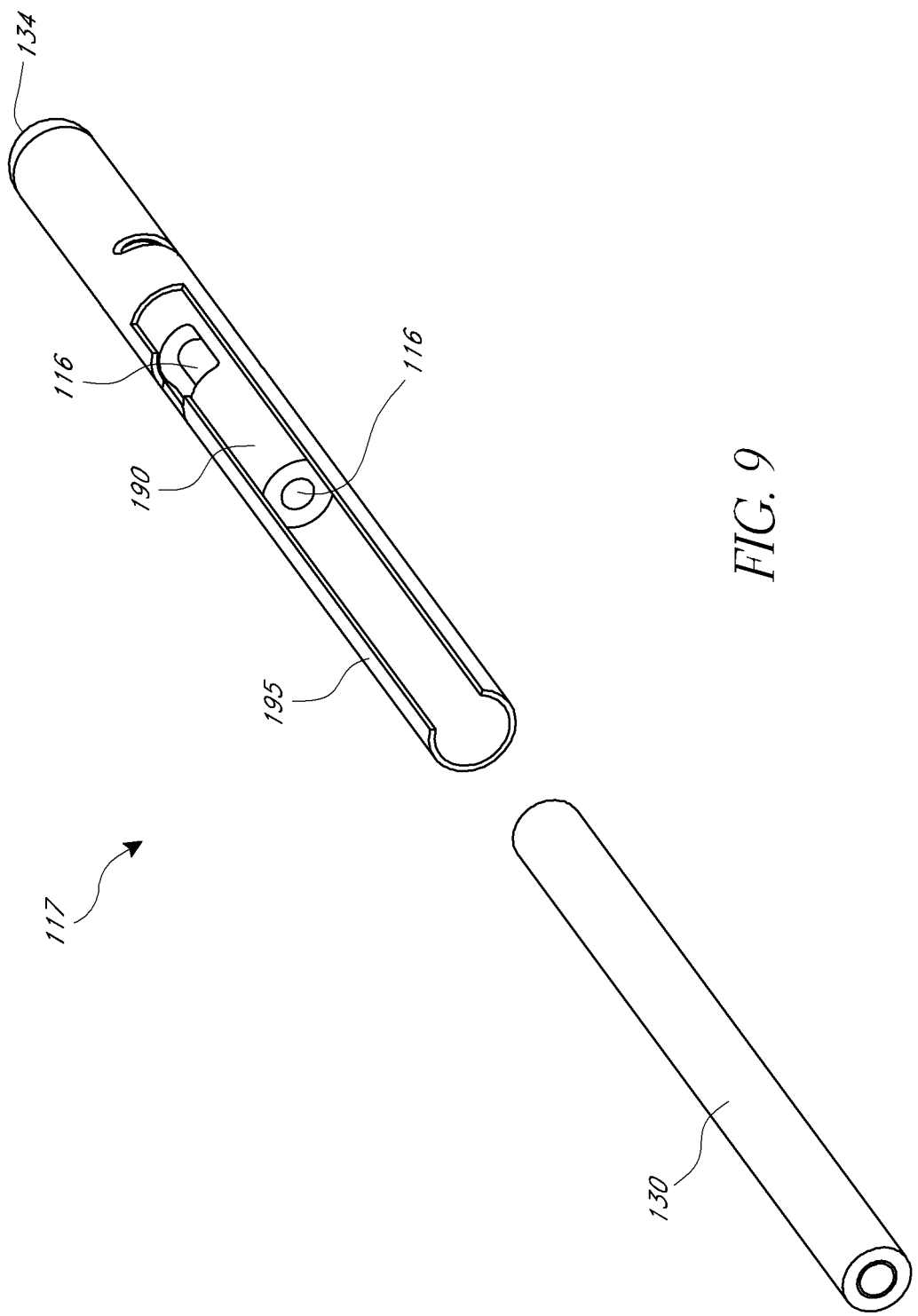
FIG. 9 shows a cross-sectional view of another embodiment of a glucose sensor having a cavity in a distal portion of the sensor enclosed within a reference material, further enclosed within a cage.
Figure 10:
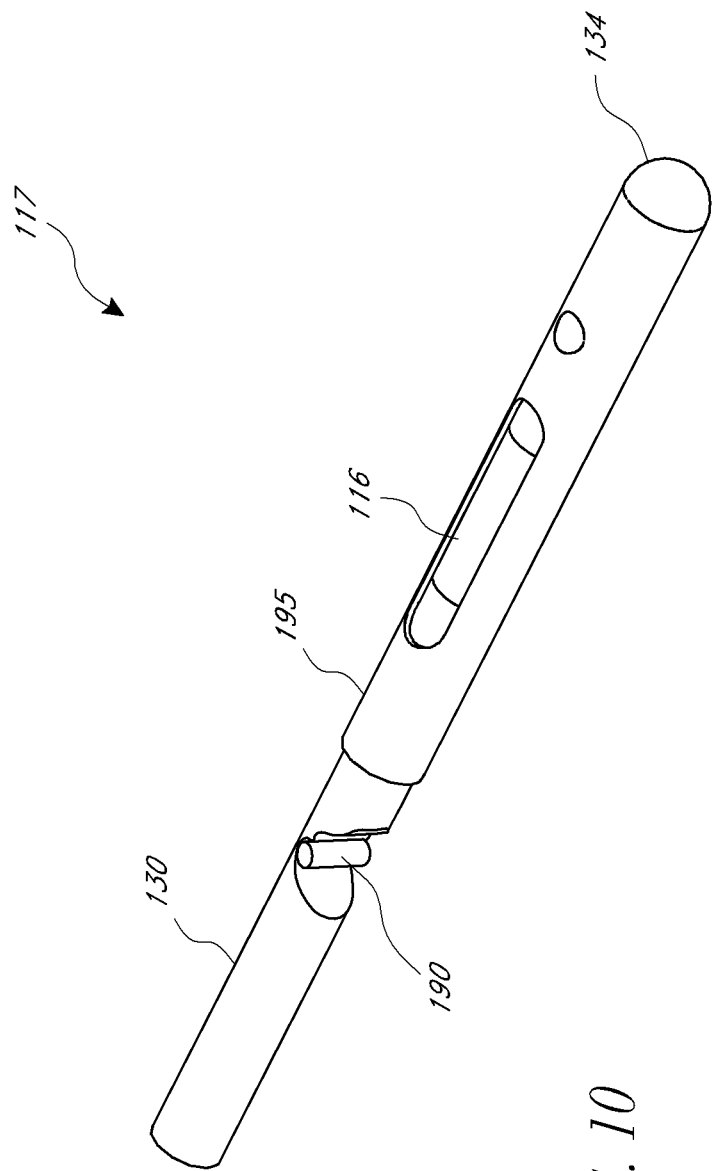
FIG. 10 shows a cross-sectional view of another embodiment of a glucose sensor having a cavity in the distal portion of the sensor enclosed within a cage and a reference material as a bar embedded within the optical fiber.
Figure 11:
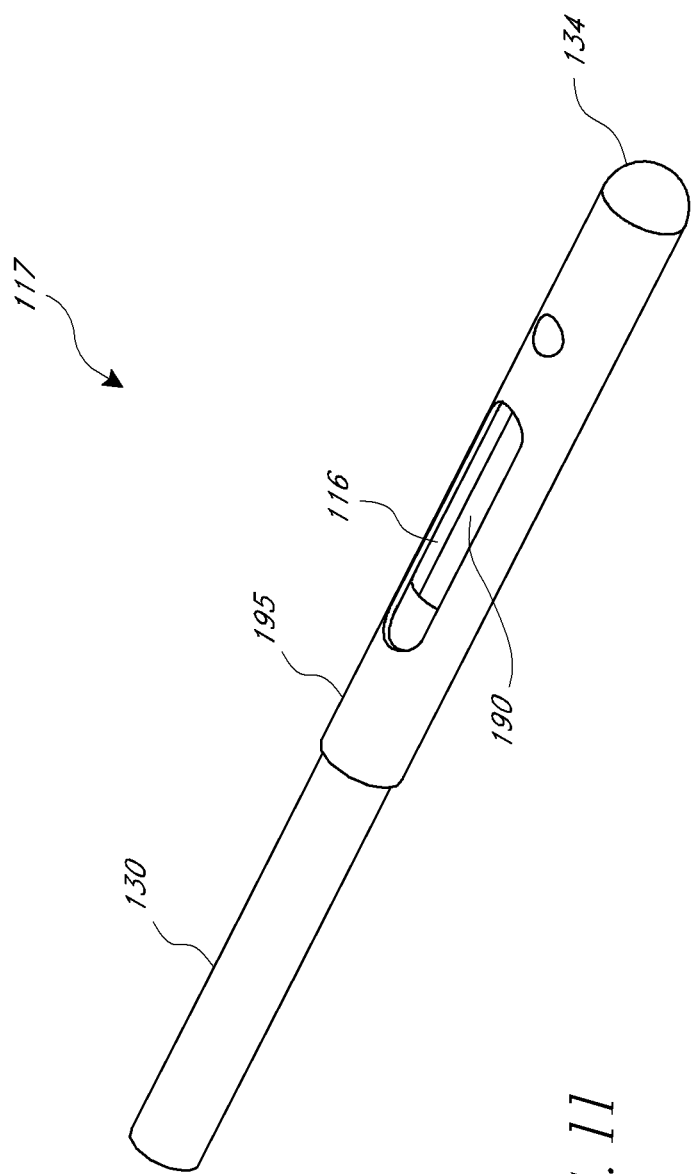
FIG. 11 shows a cross-sectional view of another embodiment of a glucose sensor having a cavity and a reference material side-by-side in the distal portion of the sensor enclosed within a cage.

In FIG. 9, the reference material 190 is disposed within the cage 195 as a hypotube containing the hydrogel-filled cavity 116 and having a reflective surface or annular mirror at the proximal surface of the hypotube 144. In certain embodiments, the hypotube 144 has an outer diameter equal to the outer diameter of the optical fiber 130. In FIG. 10, similar to FIG. 8, the reference material 190 is reflective strip, but the reflective strip in FIG. 10 is placed within a hole drilled in the optical fiber 130, rather than the abutting the hydrogel-filled cavity 116. FIG. 11 illustrates an embodiment in which the reference material 190 is located in the cavity 116 and is in a side-by-side configuration with the hydrogel/chemical indicator system.

Figure 12:
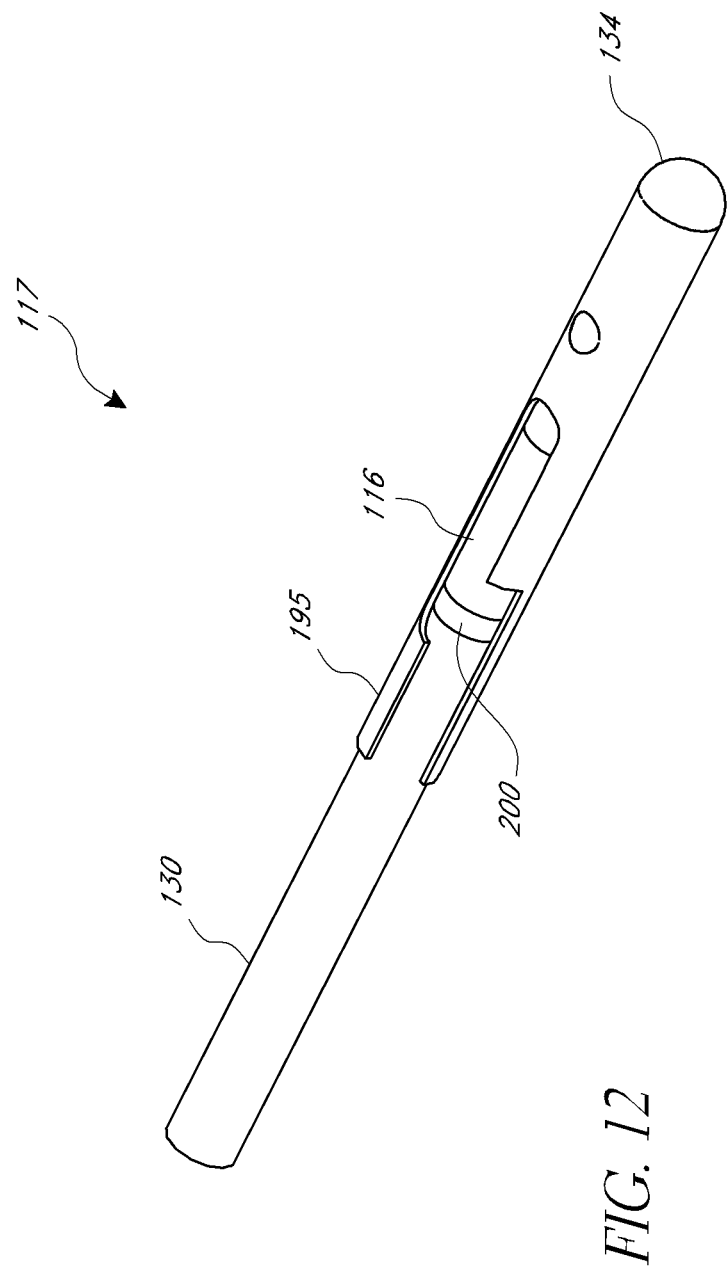
FIG. 12 shows a cross-sectional view of another embodiment of a glucose sensor having a cavity in the distal portion of the sensor enclosed within a cage and a translucent reference material between the optical fiber and cavity.

In certain embodiments, as illustrated in FIG. 12, a reference material 200 comprises a translucent material. In certain embodiments, this translucent material comprises a red dye, such as the glucose-insensitive fluorescent dye discussed previously. The red dye may allow some of the excitation light to be transmitted to the hydrogel-filled cavity 116, may reflect some of the excitation light back to a detector (not shown) before the excitation light reaches the hydrogel-filled cavity 116, and may emit a separate glucose-insensitive signal to a detector (not shown).

A person skilled in the art would readily understand that the above described embodiments, or components of the above described embodiments, may be combined within the scope of the present invention. For example, a glucose sensor may contain one or more structural elements, such as a cage, a hypotube, and/or a rod within the scope of the present invention. In addition, a glucose sensor may contain one or more reference materials, functioning as a reflective surface and/or as a separate dye indicator system, in different locations and configurations within the scope of the present invention.

In some embodiments (see e.g., FIGS. 2-12), the glucose sensor 117 comprises an atraumatic tip portion 134. The atraumatic tip portion 134 has a distal end 138 that is curved and substantially free of sharp edges. In addition, the atraumatic tip portion 134 can be flexible and deformable. The distal end 138 of the atraumatic tip portion 134 can be hemispherical, parabolic, elliptical or curved in any other suitable shape that is reduces the risk of injury to the patient. The atraumatic tip portion 134 can be made from a variety of materials, such as plastics, polymers, gels, metals and composites of the above.

In some embodiments, the glucose sensor 117 includes a temperature sensor or probe 146, such as thermocouple or thermistor (See e.g., FIG. 2A). The temperature sensor 146 can measure the temperature of the hydrogel and glucose sensing chemistry system, and/or the blood when disposed intravascularly. The temperature sensor 146 is particularly preferred when the glucose-sensing chemistry is affected by temperature. For example, in some embodiments, the fluorescence intensity emitted by the fluorophore system is dependent on the temperature of the fluorophore system. By measuring the temperature of the fluorophore system, temperature induced variations in fluorophore fluorescence intensity can be accounted for, allowing for more accurate determination of glucose concentration.

In certain embodiments, the temperature sensor can be a thermistor (as described above with regard to FIG. 2, reference numeral 146, a platinum resistance temperature device ("RTD"), another RTD, a thermocouple, an infrared-based temperature detector, a fluorescence-based temperature sensing element, or other temperature sensing elements with determinable temperature-dependent characteristics.

Devices such as thermistors, platinum RTDs, and other RTDs generally require one or more conductors, such as wires, to conduct the output of the sensor to a receiving unit which converts the output to a temperature signal. The conductors can be bundled with the optical fiber of fluorescence-based glucose sensors, such as those discussed above, or they can be routed separately. In one embodiment, the temperature sensor is placed inside the body, and the receiver is placed outside the body. In another embodiment, the temperature sensor is placed inside the body, and a transmitter, signal processor, etc. is also placed inside the body and is connected to or is a part of the temperature sensor. In preferred embodiments, the temperature sensing element is located at or near the glucose sensing moiety.

In another embodiment, a fluorescence-based temperature sensing technique can be used. Fluorescence-based temperature sensing techniques include those based on fluorescence decay, such as where an excitation light is provided to a phosphor, the excitation light is stopped, and the fluorescence is monitored versus time, with the rate of decrease in fluorescence being related to the temperature of the phosphor. Various techniques, can also include phase measurement and phase angle analysis.

Methods for performing fluorescence-based temperature measurement have been described. See for example, LumaSense Technologies, Inc. (Santa Clara, Calif.), "Fluoroptic Temperature Monitoring," http://www.lumasenseinc.com/technology/fluoroptic_thermometry.html. Fluorescent materials that can be used in fluorescence-based temperature measurement are known to, or readily identified by those having skill in the art.

In some embodiments, the fluorescent material can be surrounded by material which prevents or inhibits chemical interaction between the fluorescent material and blood components. Suitable materials include glass (for example, borosilicate, lime-soda, or other types including those used for fiberoptic cables), polymers (for example, Teflon, fluoropolymers, silicone, latex, polyolefins, polyisoprene, and other rigid and nonrigid polymeric materials), metals (for example, 300 series stainless steel, 400 series stainless steel, nickel, nickel alloys, chromium steels, zirconium and its alloys, titanium and its alloys, as well as other corrosion resistant metals and alloys including exotic metals and alloys), ceramics (for example, ceramic materials related to aluminum oxide, silica and oxide, zirconium, carbides, etc.), and combinations of these.

In some embodiments, the temperature sensor can be positioned within the glucose sensor, or near it. While in one preferred embodiment, the temperature sensor can be positioned as close as possible to (e.g., within) the glucose-sensing chemical indicator system of the glucose sensor, positions some distance away can also be successfully utilized, including those locations where the temperature measured provides an indication of the temperature at the glucose-sensing site(s) within an acceptable error for the use for which the temperature measurement is being made.

In some embodiments, the temperature sensor and/or the leads to the sensor can be isolated from the physiological environment, such as by coating, covering, or encasing the various parts with a material that prevents or inhibits chemical or physical interaction between the temperature sensor and/or its leads and blood components. Chemical interactions that are preferably avoided include corrosion, leaching of chemical species, generation of additional signals (e.g. optical, electrical, etc.) and take-up by the body of materials present in the sensor or leads, whether present from manufacture, corrosion or other means, such as compounds, metals, or ions causing a physiological response in some patients including copper, silver, organic compounds, organometallic compounds, etc.

Physical interactions can include breakage and physical separation (e.g. disconnection and potential loss), signal leakage (e.g. optical; electrical, etc.), signal degradation (including resistance, stray signal detection, noise, capacitance, electrochemical effects, induced voltages, ground loops, etc.). Suitable materials include glass (e.g., borosilicate, lime-soda, as well as other types of glass, such as those used in production of optic fibers), polymers (e.g., Teflon, fluoropolymers, silicone, latex, polyolefins, polyisoprene, acrylics, polycarbonates, and other rigid and nonrigid polymeric materials), metals (e.g., 300 series stainless steel, 400 series stainless steel, nickel, nickel alloys, chromium steels, zirconium and its alloys, titanium and its alloys, as well as other corrosion resistant metals and alloys including exotic metals and alloys), ceramics (e.g., ceramic materials related to aluminum oxide, silica and oxide, zirconium, carbides, etc.), and combinations of these.

Suitable methods for applying for isolating material to the temperature sensor or leads can include any appropriate method, including casting, painting, dipping, gluing, reacting, drawing, depositing, mechanically adhering, encapsulating, etc.

In some embodiments, suitable sizes for temperature sensors that will be incorporated into the glucose sensor include those temperature sensing elements resulting in an overall glucose sensor of between about 0.005 inches and 0.020 inches.

Figure 13:
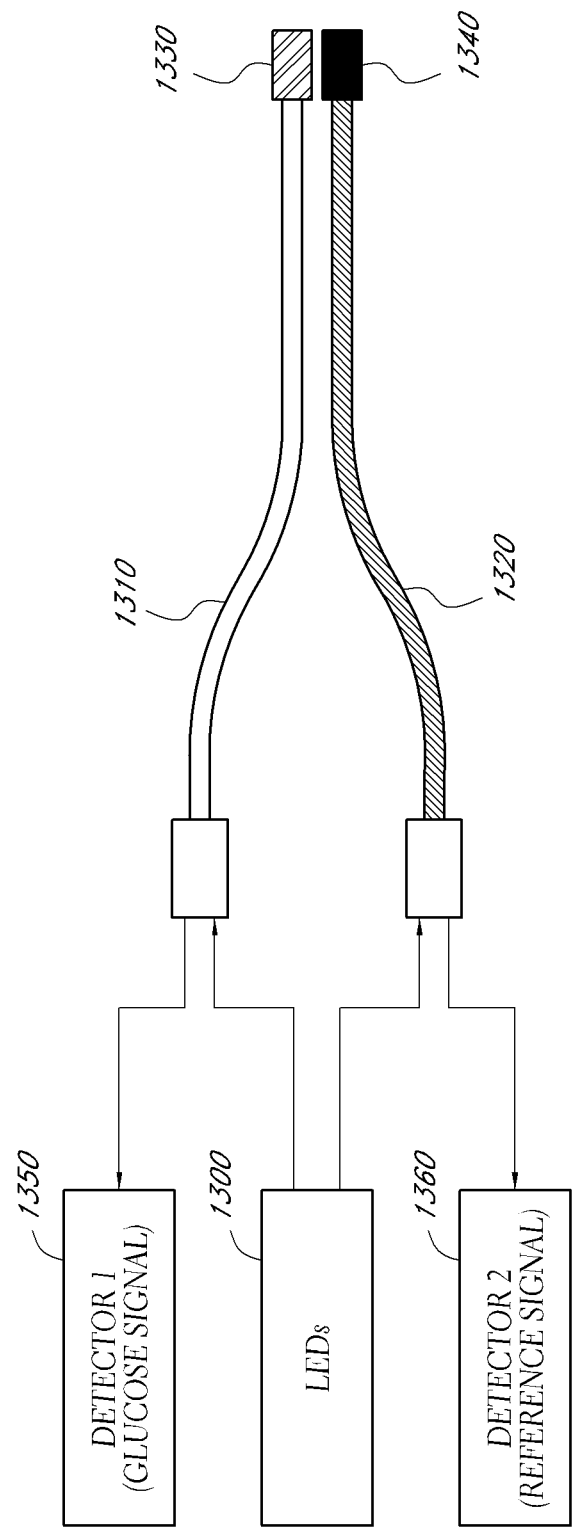
FIG. 13 shows a schematic view of another embodiment of a glucose sensor having a glucose sensing optical fiber adjacent to a reference optical fiber.

FIG. 13 illustrates another embodiment for measuring the glucose concentration in comparison to a reference signal. In this embodiment, a LED source 1300 sends an excitation signal down two separate adjacent optical fibers 1310, 1320. The first optical fiber, or the glucose fiber 1310, has a proximal tip and a distal tip. The distal tip has a glucose sensing hydrogel 1330 which contains a fluorophore or dye, a quencher, and glucose binding receptors. The second optical fiber, or the reference fiber 1320, also has a proximal tip and a distal tip. The distal tip of the reference fiber has a reference material 1340. In certain embodiments, the reference material 1340 contains the same or a different fluorophore or dye, may or may not contain the quencher, but does not contain glucose receptors. In other embodiments, the reference material 1340 has the same exact glucose sensing hydrogel, but it is encased in a glucose impermeable membrane. In both of these embodiments, the reference fiber 1320 emits a fluorescent return signal independent of the glucose concentration.

After the excitation light passes through the glucose fiber 1310 and the reference fiber 1320, the glucose sensing hydrogel 1330 and the reference material 1340 emit fluorescent signals back to two separate detectors, a glucose signal detector 1350 and a reference signal detector 1360, for ratiometric processing. The benefit of the dual fiber configuration is that both fibers 1310, 1320 experience the same external pressure, bending, temperature, and other external factors. In addition, both fibers 1310, 1320 contain substantially the same material in the glucose sensing hydrogel 1330 and reference material 1340. As a result, the ratio of the intensities between the two fibers 1310, 1320, as measured by the detectors 1350, 1360, produce a calibrated glucose signal that removes, inter alia, the effect of the fluctuations in the LED output or altered transmission along the optical fiber, and thereby increase the accuracy in the measurement of the glucose concentration.

Chemical Indicator Systems

Fluorophores

"Fluorophore" refers to a substance that when illuminated by light at a particular wavelength emits light at a longer wavelength; i.e. it fluoresces. Fluorophores include but are not limited to organic dyes, organometallic compounds, metal chelates, fluorescent conjugated polymers, quantum dots or nanoparticles and combinations of the above. Fluorophores may be discrete moieties or substituents attached to a polymer.

Fluorophores that may be used in preferred embodiments are capable of being excited by light of wavelength at or greater than about 400 nm, with a Stokes shift large enough that the excitation and emission wavelengths are separable by at least 10 nm. In some embodiments, the separation between the excitation and emission wavelengths may be equal to or greater than about 30 nm. These fluorophores are preferably susceptible to quenching by electron acceptor molecules, such as viologens, and are resistant to photobleaching. They are also preferably stable against photooxidation, hydrolysis and biodegradation.

In some embodiments, the fluorophore may be a discrete compound.

In some embodiments, the fluorophore may be a pendant group or a chain unit in a water-soluble or water-dispersible polymer having molecular weight of about 10,000 daltons or greater, forming a dye-polymer unit. In one embodiment, such dye-polymer unit may also be non-covalently associated with a water-insoluble polymer matrix $M^1$ and is physically immobilized within the polymer matrix $M^1$, wherein $M^1$ is permeable to or in contact with analyte solution. In another embodiment, the dye on the dye-polymer unit may be negatively charged, and the dye-polymer unit may be immobilized as a complex with a cationic water-soluble polymer, wherein said complex is permeable to or in contact with the analyte solution. In one embodiment, the dye may be one of the polymeric derivatives of hydroxypyrene trisulfonic acid. The polymeric dyes may be water-soluble, water-swellable or dispersible in water. In some embodiments, the polymeric dyes may also be cross-linked. In preferred embodiments, the dye has a negative charge.

In other embodiments, the dye molecule may be covalently bonded to the water-insoluble polymer matrix $M^1$, wherein said $M^1$ is permeable to or in contact with the analyte solution. The dye molecule bonded to $M^1$ may form a structure $M^1$-$L^1$-Dye. $L^1$ is a hydrolytically stable covalent linker that covalently connects the sensing moiety to the polymer or matrix. Examples of $L^1$ include lower alkylene (e.g., $C_1$-$C_8$ alkylene), optionally terminated with or interrupted by one or more divalent connecting groups selected from sulfonamide (—$SO_2NH$—), amide —(C=O)N—, ester —(C=O)—O—, ether.—O—, sulfide —S—, sulfone (—$SO_2$—), phenylene —$C_6H_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like, or a combination thereof. In one embodiment, the dye is bonded to a polymer matrix through the sulfonamide functional groups.

In some embodiments, useful dyes include pyranine derivatives (e.g. hydroxypyrene trisulfonamide derivatives and the like), which have the following formula:

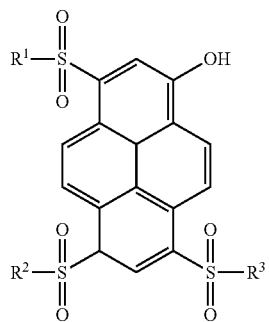

wherein $R^1$, $R^2$, $R^3$ are each —$NHR^4$, $R^4$ is —$CH_2CH_2$(—$OCH_2CH_2$—)$_n X^1$; wherein $X^1$ is —OH, —$OCH_3COOH$, —$CONH_2$, —$SO_3H$, —$NH_2$, or OMe; and n is between about 70 and 10,000. In one embodiment, the dyes may be bonded to a polymer through the sulfonamide functional groups. In other embodiments, the dye may be one of the polymeric derivatives of hydroxypyrene trisulfonic acid.

In some embodiments, the fluorescent dye may be 8-hydroxypyrene-1,3,6-trisulfonate (HPTS). The counterions can be $H^+$ or any other cation. HPTS exhibits two excitation wavelengths at around 450 nm and around 405 nm, which correspond to the absorption wavelengths of the acid and its conjugate base. The shift in excitation wavelength is due to the pH-dependent ionization of the hydroxyl group on HPTS. As the pH increases, HPTS shows an increase in absorbance at about 450 nm, and a decrease in absorbance below about 420 nm. The pH-dependent shift in the absorption maximum enables dual-excitation ratiometric detection in the physiological range. This dye has a molecular weight of less than 500 daltons, so it will not stay within the polymer matrix, but it can be used with an anion exclusion membrane.

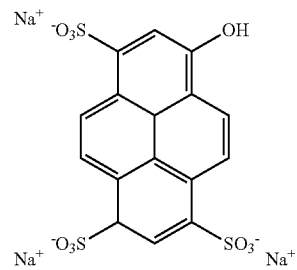

(the $Na^+$ salt of HPTS—"pyranine")

In another embodiment, the fluorescent dye may be polymers of 8-acetoxy-pyrene-1,3,6-N,N',N''-tris-(methacrylpropylamidosulfonamide) (acetoxy-HPTS-MA):

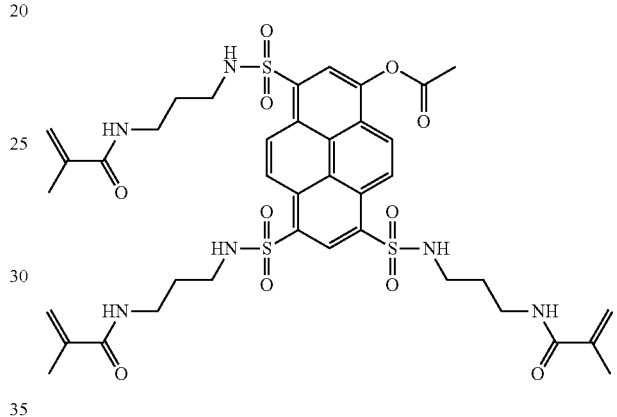

It is noted that dyes such as acetoxy-HPTS-MA (above) having no anionic groups, may not give very strong glucose response when operably coupled to a viologen quencher, particularly a viologen quencher having only a single boronic acid moiety.

In another embodiment, the fluorescent dye may be 8-hydroxy-pyrene-1,3,6-N,N',N''-tris-(carboxypropylsulfonamide) (HPTS-$CO_2$):

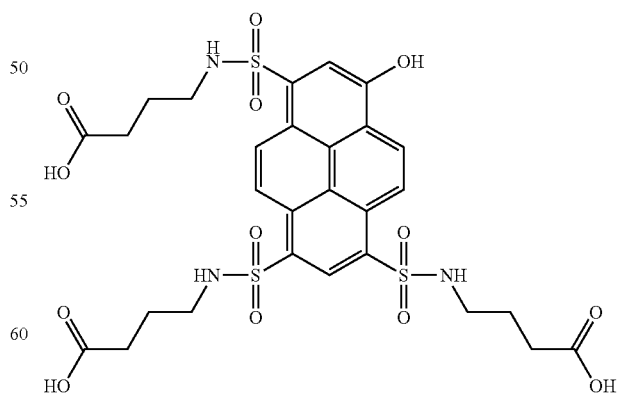

In another embodiment, the fluorescent dye may be 8-hydroxy-pyrene-1,3,6-N,N',N''-tris-(methoxypolyethoxyethyl (~125) sulfonamide) (HPTS-PEG):

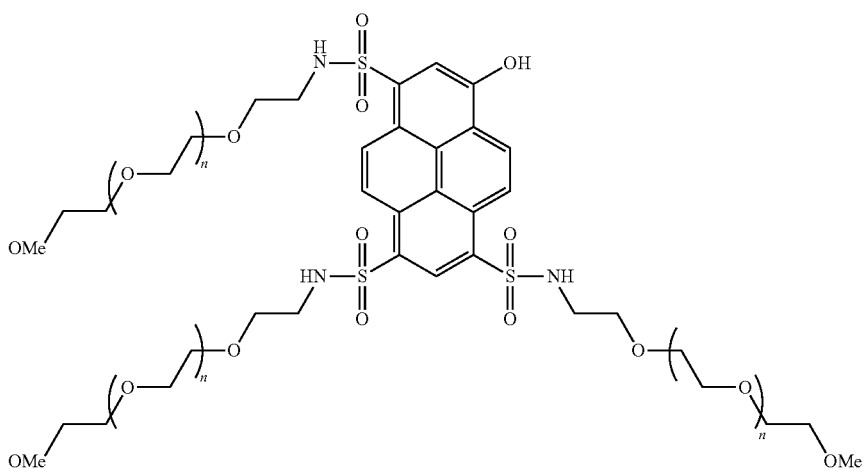

It is noted that dyes such as HPTS-PEG (above) having no anionic groups, may not provide a very strong glucose response when operably coupled to a viologen quencher, particularly a viologen quencher having only a single boronic acid moiety.

Representative dyes as discrete compounds are the tris adducts formed by reacting 8-acetoxypyrene-1,3,6-trisulfonylchloride (HPTS-Cl) with an amino acid, such as amino butyric acid. Hydroxypyrene trisulfonamide dyes bonded to a polymer and bearing one or more anionic groups are most preferred, such as copolymers of 8-hydroxypyrene-1-N-(methacrylamidopropylsulfonamido)-N',N"-3,6-bis(carboxypropylsulfonamide) HPTS-$CO_2$-MA with HEMA, PEGMA, and the like.

In another embodiment, the fluorescent dye may be HPTS-TriCys-MA:

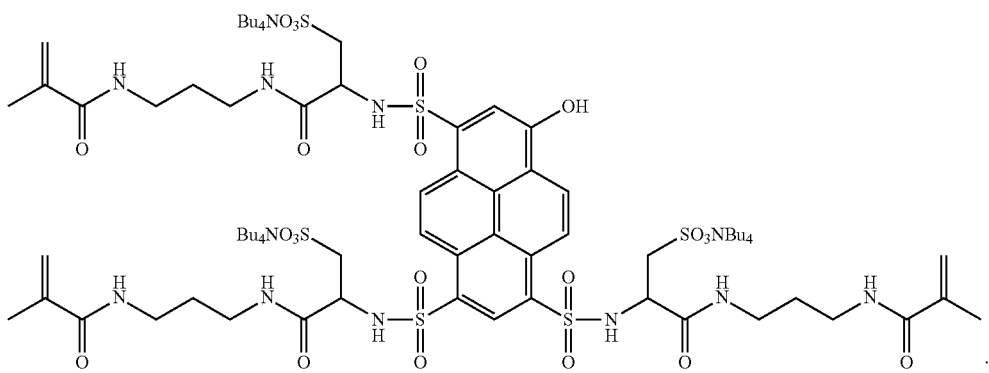

This dye may be used with a quencher comprising boronic acid, such as 3,3'-oBBV.

Of course, in some embodiments, substitutions other than Cys-MA on the HPTS core are consistent with aspects of the present invention, as long as the substitutions are negatively charged and have a polymerizable group. Either L or D stereoisomers of cysteine may be used. In some embodiments, only one or two of the sulfonic acids may be substituted. Likewise, in variations to HPTS-CysMA shown above, other counterions besides $NBu_4^+$ may be used, including positively charged metals, e.g., $Na^+$. In other variations, the sulfonic acid groups may be replaced with e.g., phosphoric, carboxylic, etc. functional groups.

Another suitable dye is HPTS-LysMA, which is pictured below as follows:

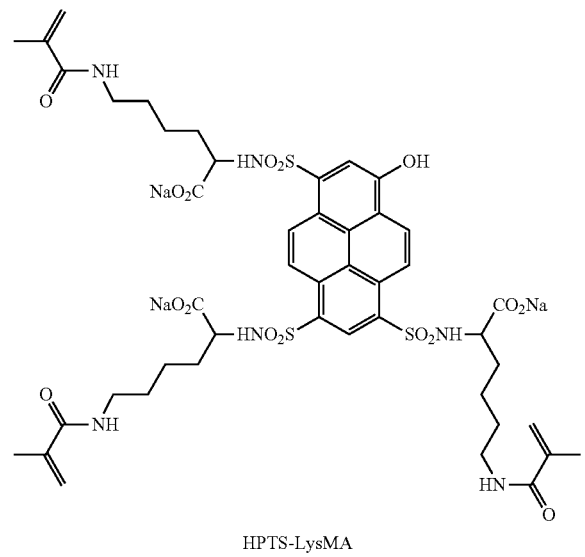

HPTS-LysMA

Other examples include soluble copolymers of 8-acetoxy-pyrene-1,3,6-N,N',N''-tris(methacrylamidopropylsulfonamide) with HEMA, PEGMA, or other hydrophilic comonomers. The phenolic substituent in the dye is protected during polymerization by a blocking group that can be removed by hydrolysis after completion of polymerization. Such suitable blocking groups, as for example, acetoxy, trifluoroacetoxy, and the like, are well known in the art.

Fluorescent dyes, including HPTS and its derivatives are known and many have been used in analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; and co-pending U.S. patent application Ser. No. 11/296,898 and 60/833,081; each of which is incorporated herein in its entirety by reference thereto.

The SNARF and SNAFL dyes from Molecular Probes may also be useful fluorophores in accordance with aspects of the present invention. The structures of SNARF-1 and SNAFL-1 are shown below.

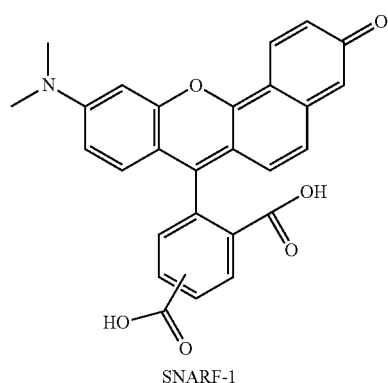

SNARF-1

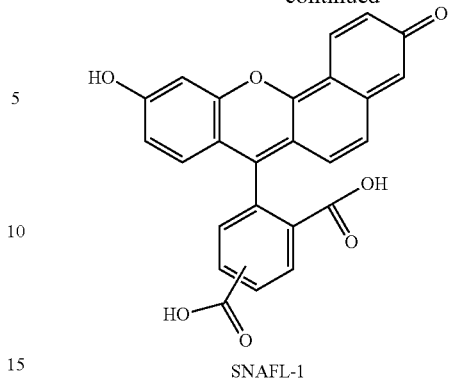

SNAFL-1

Additionally, a set of isomeric water-soluble fluorescent probes based on both the 6-aminoquinolinium and boronic acid moieties which show spectral shifts and intensity changes with pH, in a wavelength-ratiometric and colorimetric manner may be useful in accordance with some embodiments of the present invention (See e.g., Badugu, R. et al. 2005 Talanta 65 (3):762-768; and Badugu, R. et al. 2005 Bioorg. Med. Chem. 13 (1):113-119); incorporated herein in its entirety by reference.

Another example of a fluorescence dye that may be pH and saccharide sensitive is tetrakis(4-sulfophenyl)porphine (TSPP)—shown below. TSPP may not work optimally in blood, where the porphyrin ring may react with certain metal ions, like ferric, and become non-fluorescent.

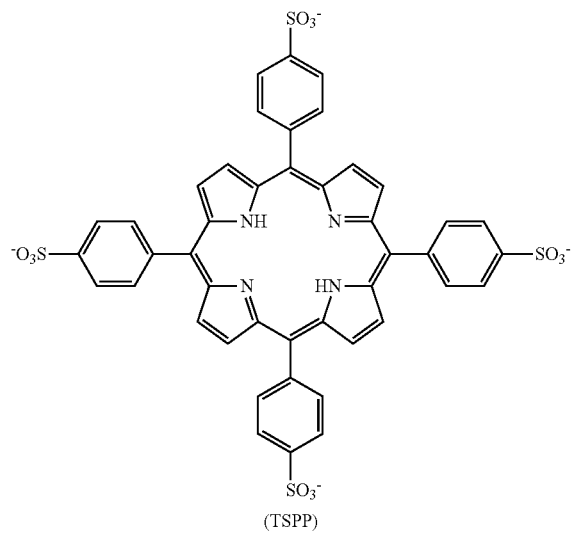

(TSPP)

Additional examples of pH sensitive fluorescent indicators that may be useful for simultaneous determination of pH and glucose in the sensor of the present invention are described in US 2005/0233465 and US 2005/0090014; each of which is incorporated herein by reference in its entirety.

In certain preferred embodiments, the fluorophore dye may be selected such that it exists in distinguishable acid and base conformations, each of which emit at a distinct wavelength, and wherein the relative proportion of acid and base forms depend on the pH. The ratio of intensities of the acid and base emissions can be used to determine the pH of the blood (as detailed in US Patent Publication No. 2008/0188722; incorporated herein in its entirety by reference thereto). The ratio of the acid or base emission intensity over the excitation light can be used to determine the level of glucose in the blood. Of course in a variation to this single exciter-dual emitter fluorophore system, one could employ a single exciter-single emitter for detection of glucose concentration without simultaneous ratiometric determination of pH. Indeed, a great variety of design options are available (see e.g., US Patent Publication Nos. 2008/0188725 and 2008/0188722), wherein the chemical indicator and optical systems may be selected based on the preferred use.

Analyte Binding Moieties—Quenchers

In accordance with broad aspects of the present disclosure, the analyte binding moiety provides the at least dual functionality of being able to bind analyte and being able to modulate the apparent concentration of the fluorophore (e.g., detected as a change in emission signal intensity) in a manner related to the amount of analyte binding. In preferred embodiments, the analyte binding moiety is associated with a quencher. "Quencher" refers to a compound that reduces the emission of a fluorophore when in its presence. Quencher (Q) is selected from a discrete compound, a reactive intermediate which is convertible to a second discrete compound or to a polymerizable compound or Q is a pendant group or chain unit in a polymer prepared from said reactive intermediate or polymerizable compound, which polymer is water-soluble or dispersible or is an insoluble polymer, said polymer is optionally crosslinked.

In one example, the moiety that provides glucose recognition in the embodiments is an aromatic boronic acid. The boronic acid is covalently bonded to a conjugated nitrogen-containing heterocyclic aromatic bis-onium structure (e.g., a viologen). "Viologen" refers generally to compounds having the basic structure of a nitrogen containing conjugated N-substituted heterocyclic aromatic bis-onium salt, such as 2,2'-, 3,3'- or 4,4'-N,N' bis-(benzyl) bipyridium dihalide (i.e., dichloride, bromide chloride), etc. Viologen also includes the substituted phenanthroline compounds. The boronic acid substituted quencher preferably has a pKa of between about 4 and 9, and reacts reversibly with glucose in aqueous media at a pH from about 6.8 to 7.8 to form boronate esters. The extent of reaction is related to glucose concentration in the medium. Formation of a boronate ester diminishes quenching of the fluorphore by the viologen resulting in an increase in fluorescence dependent on glucose concentration. A useful bis-onium salt is compatible with the analyte solution and capable of producing a detectable change in the fluorescent emission of the dye in the presence of the analyte to be detected.

Bis-onium salts in the embodiments of this disclosure are prepared from conjugated heterocyclic aromatic di-nitrogen compounds. The conjugated heterocyclic aromatic di-nitrogen compounds are selected from dipyridyls, dipyridyl ethylenes, dipyridyl phenylenes, phenanthrolines, and diazafluorenes, wherein the nitrogen atoms are in a different aromatic ring and are able to form an onium salt. It is understood that all isomers of said conjugated heterocyclic aromatic di-nitrogen compounds in which both nitrogens can be substituted are useful in this disclosure. In one embodiment, the quencher may be one of the bis-onium salts derived from 3,3'-dipyridyl, 4,4'-dipyridyl and 4,7-phenanthroline.

In some embodiments, the viologen-boronic acid adduct may be a discrete compound having a molecular weight of about 400 daltons or greater. In other embodiments, it may also be a pendant group or a chain unit of a water-soluble or water-dispersible polymer with a molecular weight greater than about 10,000 daltons. In one embodiment, the quencher-polymer unit may be non-covalently associated with a polymer matrix and is physically immobilized therein. In yet another embodiment, the quencher-polymer unit may be immobilized as a complex with a negatively charge water-soluble polymer.

In other embodiments, the viologen-boronic acid moiety may be a pendant group or a chain unit in a crosslinked, hydrophilic polymer or hydrogel sufficiently permeable to the analyte (e.g., glucose) to allow equilibrium to be established.

In other embodiments, the quencher may be covalently bonded to a second water-insoluble polymer matrix $M^2$, which can be represented by the structure $M^2$-$L^2$-Q. $L^2$ is a linker selected from the group consisting of a lower alkylene (e.g., $C_1$-$C_8$ alkylene), sulfonamide, amide, quaternary ammonium, pyridinium, ester, ether, sulfide, sulfone, phenylene, urea, thiourea, urethane, amine, and a combination thereof. The quencher may be linked to $M^2$ at one or two sites in some embodiments.

For the polymeric quencher precursors, multiple options are available for attaching the boronic acid moiety and a reactive group which may be a polymerizable group or a coupling group to two different nitrogens in the heteroaromatic centrally located group. These are:

a) a reactive group on a first aromatic moiety is attached to one nitrogen and a second aromatic group containing at least one —B(OH)$_2$ group is attached to the second nitrogen;

b) one or more boronic acid groups are attached to a first aromatic moiety which is attached to one nitrogen and one boronic acid and a reactive group are attached to a second aromatic group which second aromatic group is attached to the second nitrogen;

c) one boronic acid group and a reactive group are attached to a first aromatic moiety which first aromatic group is attached to one nitrogen, and a boronic acid group and a reactive group are attached to a second aromatic moiety which is attached to the second nitrogen; and d) one boronic acid is attached to each nitrogen and a reactive group is attached to the heteroaromatic ring.

Preferred embodiments comprise two boronic acid moieties and one polymerizable group or coupling group wherein the aromatic group is a benzyl substituent bonded to the nitrogen and the boronic acid groups are attached to the benzyl ring and may be in the ortho-meta or para-positions.

In some embodiments, the boronic acid substituted viologen as a discrete compound useful for in vitro sensing may be represented by one of the following formulas:

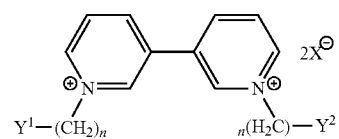

-continued

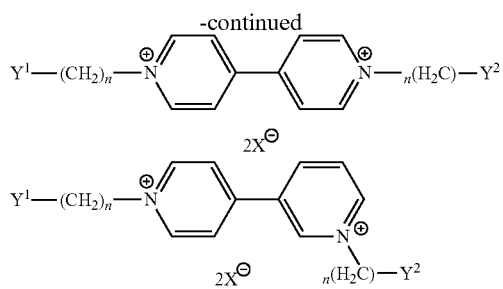

where n=1-3, X is halogen, and $Y^1$ and $Y^2$ are independently selected from phenyl boronic acid (o- m- or p-isomers) and naphthyl boronic acid. In other embodiments, the quencher may comprise a boronic acid group as a substituent on the heterocyclic ring of a viologen.

A specific example used with TSPP is m-BBV:

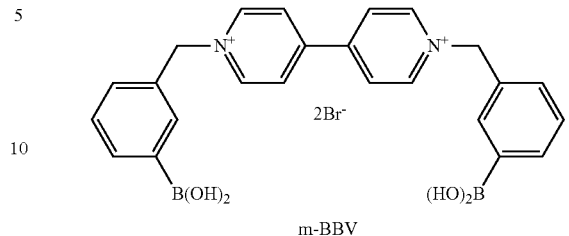

m-BBV

The quencher precursors suitable for making sensors may be selected from the following:

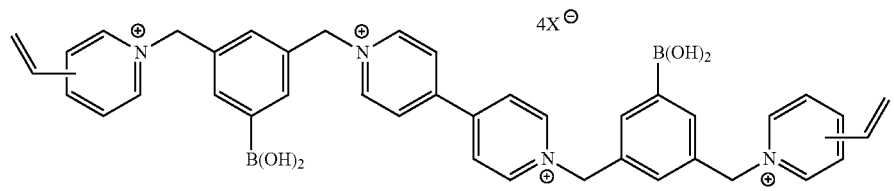

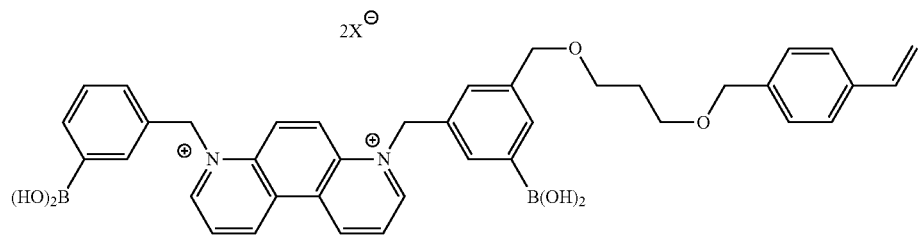

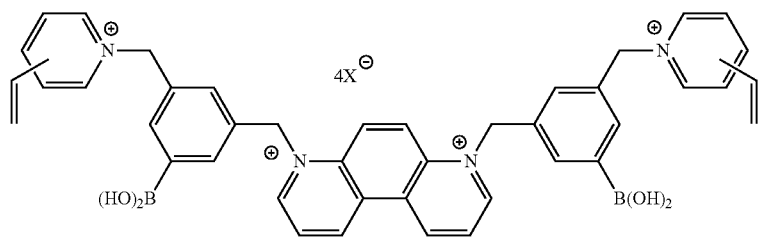

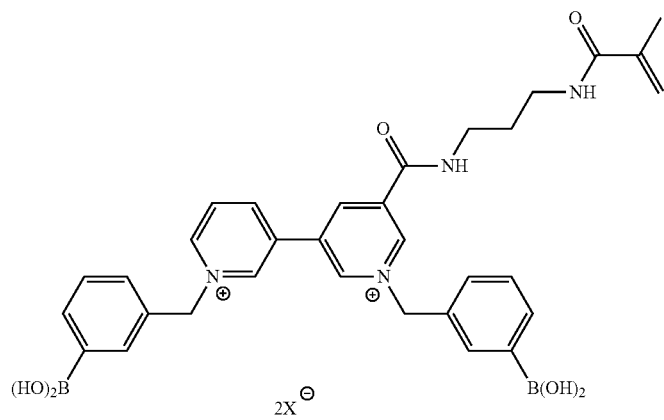

-continued
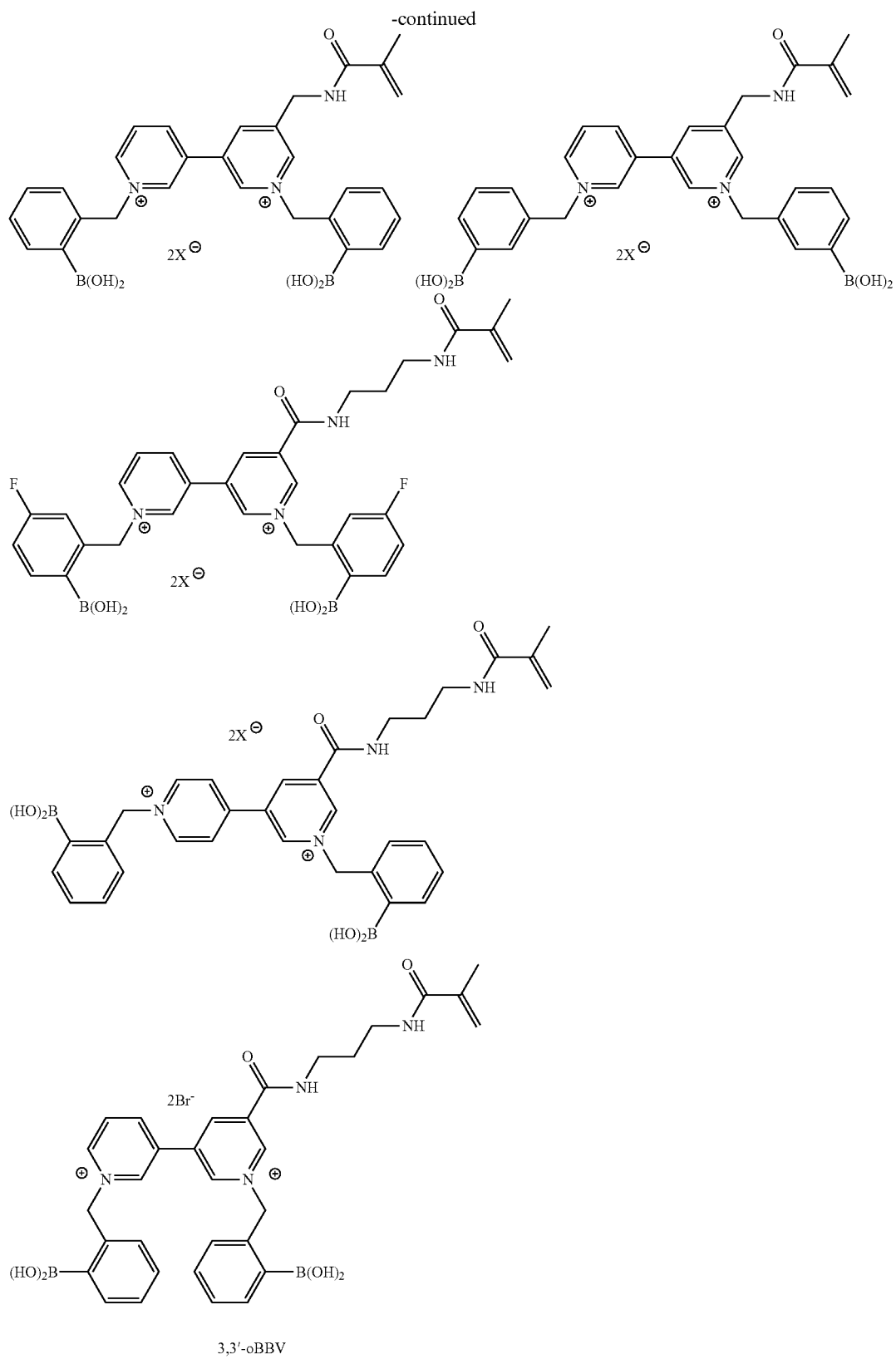
3,3'-oBBV
The quencher precursor 3,3'-oBBV may be used with HPTS-LysMA or HPTS-CysMA to make hydrogels in accordance with preferred aspects of the disclosure.
Preferred quenchers are prepared from precursors comprising viologens derived from 3,3'-dipyridyl substituted on the nitrogens with benzylboronic acid groups and at other positions on the dipyridyl rings with a polymerizable group or a coupling group. Representative viologens include:

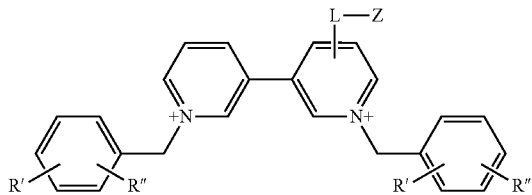

where L is L1 or L2 and is a linking group

Z is a reactive group; and

R' is —B(OH)$_2$ in the ortho- meta- or para-positions on the benzyl ring and R" is H—; or optionally R" is a coupling group as is defined herein or a substituent specifically used to modify the acidity of the boronic acid such as fluoro- or methoxy- L is a divalent moiety that covalently connects the sensing moiety to a reactive group that is used to bind the viologen to a polymer or matrix. Examples of L include those which are each independently selected from a direct bond or, a lower alkylene having 1 to 8 carbon atoms, optionally terminated with or interrupted by one or more divalent connecting groups selected from sulfonamide (—SO$_2$NH—), amide —(C═O)N—, ester —(C═O)—O—, ether —O—, sulfide —S—, sulfone (—SO$_2$—), phenylene —C$_6$H$_4$—, urethane —NH(C═O)—O—, urea —NH(C═O)NH—, thiourea —NH(C═S)—NH—, amide —(C═O)NH—, amine —NR— (where R is defined as alkyl having 1 to 6 carbon atoms) and the like.

Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$.

Boronic acid substituted polyviologens are another class of preferred quenchers. The term polyviologen includes: a discrete compound comprised of two or more viologens covalently bonded together by a linking group, a polymer comprised of viologen repeat units in the chain, a polymer with viologen groups pendant to the chain, a dendrimer comprised of viologen units, preferably including viologen terminal groups, an oligomer comprised of viologen units, preferably including viologen endgroups, and combinations thereof. Polymers in which mono-viologen groups form a minor component are not included. The preferred quenchers are water soluble or dispersible polymers, or crosslinked, hydrophilic polymers or hydrogels sufficiently permeable to glucose to function as part of a sensor. Alternatively the polyviologen boronic acid may be directly bonded to an inert substrate.

A polyviologen quencher as a polymer comprised of viologen repeat units has the formula:

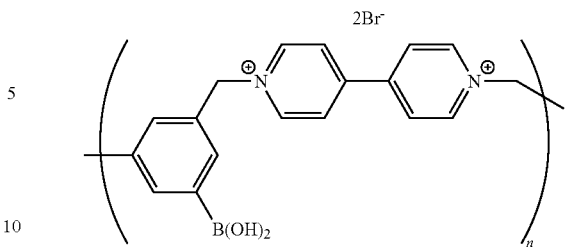

In another embodiment, the polyviologen boronic acid adducts are formed by covalently linking two or more viologen/boronic acid intermediates. The bridging group is typically a small divalent radical bonded to one nitrogen in each viologen, or to a carbon in the aromatic ring of each viologen, or one bond may be to a ring carbon in one viologen and to a nitrogen in the other. Two or more boronic acid groups are attached to the polyviologen. Optionally, the polyviologen boronic acid adduct is substituted with a polymerizable group or coupling group attached directly to the viologen or to the bridging group. Preferably the polyviologen moiety includes only one such group. Preferably, the bridging group is selected to enhance cooperative binding of the boronic acids to glucose.

The coupling moiety is a linking group as defined previously with the proviso that the linking group is optionally further substituted with a boronic acid, a polymerizable group, an additional coupling group, or is a segment in a polymer chain in which the viologen is a chain unit, a pendant group, or any combination thereof.

Polymer Matrices (Immobilizing Means)

For in vivo applications, the sensor is used in a moving stream of physiological fluid (e.g. in a blood vessel) or within the intradermal space, subcutaneous space, or in tissues—bathed in interstitial fluid, wherein the physiological fluid (blood or interstitial fluid) contains one or more polyhydroxyl organic compounds. Therefore, it is preferred that none of the sensing moieties escape from the sensor assembly. Thus, for use in vivo, the sensing components are preferably part of an organic polymer sensing assembly. Soluble dyes and quenchers can be confined by a semipermeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained.

Preferably the sensing moieties are immobilized in an insoluble polymer matrix, which is freely permeable to glucose. The polymer matrix is comprised of organic, inorganic or combinations of polymers thereof. The matrix may be composed of biocompatible materials. Alternatively, the matrix is coated with a second biocompatible polymer that is permeable to the analytes of interest.

The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium. chloride, vinyl benzyl trimethyl ammonium chloride, sodium sulfopropyl methacrylate, and the like; crosslinkers include ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is derived from an ethylenically unsaturated derivative of a dye molecule, such as 8-acetoxypyrene-1,3,6-N,N',N'''-tris(methacrylamidopropylsulfonamide), the quencher moiety is derived from an ethylenically unsaturated viologen such as 4-N-(benzyl-3-boronic acid)-4'-N'-(benzyl-4-ethenyl)-dipyridinium dihalide (m-SBBV) and the matrix is made from HEMA and PEGDMA. The concentration of dye is chosen to optimize emission intensity. The ratio of quencher to dye is adjusted to provide sufficient quenching to produce the desired measurable signal.

In some embodiments, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2 hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

In other embodiments, multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multicomponent system is an interpenetrating polymer network (IPN) or a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and polymerizing the mixture. In some embodiments, the sensing moieties are immobilized by an insoluble polymer matrix which is freely permeable to polyhydroxyl compounds. Additional details on hydrogel systems have been disclosed in US Patent Publications Nos. US2004/0028612, and 2006/0083688 which are hereby incorporated by reference in their entireties.

The polymer matrix is comprised of organic, inorganic or combinations of polymers thereof. The matrix may be composed of biocompatible materials. Alternatively, the matrix is coated with a second biocompatible polymer that is permeable to the analytes of interest. The function of the polymer matrix is to hold together and immobilize the fluorescent dye and quencher moieties while at the same time allowing contact with the analytes (e.g., polyhydroxyl compounds, $H^+$ and $OH^-$), and binding of the polyhydroxyl compounds to the boronic acid. Therefore, the matrix is insoluble in the medium and in close association with it by establishing a high surface area interface between matrix and analyte solution. The matrix also does not interfere with transport of the analyte to the binding sites so that equilibrium can be established between the two phases. In one embodiment, an ultra-thin film or microporous support matrix may be used. In another embodiment, the matrix that is swellable in the analyte solution (e.g. a hydrogel matrix) can be used for aqueous systems. In some embodiments, the sensing polymers are bonded to a surface such as the surface of a light conduit, or impregnated in a microporous membrane. Techniques for preparing ultra-thin films, microporous polymers, microporous sol-gels, and hydrogels have been established in the prior art.

In one preferred embodiment, the boronic acid substituted viologen may be covalently bonded to a fluorescent dye. The adduct may be a polymerizable compound or a unit in a polymer. One such adduct for example may be prepared by first forming an unsymmetrical viologen from 4,4'-dipyridyl by attaching a benzyl-3-boronic acid group to one nitrogen and an aminoethyl group to the other nitrogen atom. The viologen is condensed sequentially first with 8-acetoxy-pyrene-1,3,6-trisulfonyl chloride in a 1:1 mole ratio followed by reaction with excess PEG diamine to obtain a prepolymer mixture. An acid acceptor is included in both steps to scavange the byproduct acid. The prepolymer mixture is crosslinked by reaction with a polyisocyanate to obtain a hydrogel. The product is treated with base to remove the acetoxy blocking group. Incomplete reaction products and unreacted starting materials are leached out of the hydrogel by exhaustive extraction with deionized water before further use. The product is responsive to glucose when used as the sensing component as described herein.

Alternatively, such adducts are ethylenically unsaturated monomer derivatives. For example, dimethyl bis-bromomethyl benzene boronate is reacted with excess 4,4'-dipyridyl to form a half viologen adduct. After removing the excess dipyridyl, the adduct is further reacted with an excess of bromoethylamine hydrochloride to form the bis-viologen adduct. This adduct is coupled to a pyranine dye by reaction with the 8-acetoxypyrene-tris sulfonyl chloride in a 1:1 mole ratio in the presence of an acid acceptor followed by reaction with excess aminopropylmethacrylamide. Finally, any residual amino groups may be reacted with methacrylol chloride. After purification, the dye/viologen monomer may be copolymerized with HEMA and PEGDMA to obtain a hydrogel.

Ratiometric pH Sensing

Ratiometric pH sensing is known. See e.g., US Pat. Publication Nos. 2006/0105174; 2005/0090014; incorporated herein in their entirety by reference. Given an indicator system comprising a fluorophore (e.g., a fluorescent indicator dye) that exists in two forms (an acid form and a base form) the ratio of the emission intensity at the two wavelengths can be used to measure pH independent of the fluorophore concentration. The fluorescent indicator dyes suitable for ratiometric pH sensing may be: (1) dyes that exhibit dual excitation wavelengths (corresponding to acid and conjugate base forms) and single emission wavelengths (e.g., HPTS dyes); (2) single excitation wavelengths and dual emission wavelengths (acid and base forms); or (3) dual excitation-dual emission dyes. Some dyes, such as the SNARF or SNAFL dyes may have both dual-emission and dual-excitation properties. However a dual-dual dye, e.g., SNARF can be used as a single-dual or a dual-single.

Dual emission fiber-optic sensors based on seminapthofluorescein and carboxynaphthofluorescein have been described that rapidly and reliably correlate intensity ratios to pH. See e.g., respectively, Xu, Z., A. Rollins, et al. (1998) "A novel fiber-optic pH sensor incorporating carboxy SNAFL-2 and fluorescent wavelength-ratiometric detection" Journal of Biomedical Materials Research 39: 9-15, and Song, A., S. Parus, et al. (1997) "High-performance fiber-optic pH microsensors for practical physiological measurements using a dual-emission sensitive dye" Analytical Chemistry 69: 863-867. The extensive photobleaching observed for these dyes may be accounted for by the ratiometric approach, but it would still limit the useful lifetime of the sensor.

The fluorescent dye 8-hydroxy-1,3,6-pyrene trisulphonic acid trisodium salt (HPTS) consists of a pyrene core with three sulfonic acid groups and a hydroxyl group that imparts pH sensitivity around a pKa of approximately 7.3 (Wolfbeis, O. S., E. Fuerlinger, et al. (1983). "Fluorimetric analysis. I. Study on fluorescent indicators for measuring near neutral ('physiological') pH values." Fresneius' Z. Anal. Chem. 314(2): 119-124); Wolfbeis et al. also have several patents on immobilized HPTS. Yafuso and Hui describe another immobilized fluorescent dye pH sensor in U.S. Pat. No. 4,886,338; incorporated herein in its entirety by reference thereto. HPTS exhibits two excitation wavelengths, one at 405 nm and one at 457 nm, that correspond to the acid and its conjugate base (Agayn, V. I. and Dr. R. Walt (1993). "Fiber-optic sensor for continuous monitoring of fermentation pH." Biotechnology 72(6):6-9). The subsequent pH-dependent shift in excitation maximum about the pKa of 7.3 enables dual-excitation/single emission ratiometric detection in the physiological range. This, together with a low toxicity (Lutty, G. A. (1978). "The acute intravenous toxicity of stains, dyes, and other fluorescent substances." Toxical Pharmacol. 44: 225-229) and insensitivity to oxygen concentration (Zhujun, Z. and W. R. Seitz (1984). "A fluorescence sensor for quantifying pH in the range from 6.5 to 8.5." Analytical Chimica Acta 160: 47-55), makes HPTS a suitable probe for physiological and bioprocess pH measurements.

The presence of the three strongly anionic sulphonic acid groups allows for HPTS to be immobilized by ionic binding to cationic supports. To date, covalent attachment of HPTS has been via sulfonamide coupling (U.S. Pat. No. 4,798,738). While effective in immobilizing the dye and preserving pH sensitivity, polymer substrates are limited to those that contain primary amines. In addition, amine groups which remain on the substrate after coupling will affect the local pH inside the polymer matrix. The dye has been covalently attached to controlled pore glass (Offenbacher, H., O. S. Wolfbeis, et al. (1986). "Fluorescence optical sensors for continuous determination of near-neutral pH values." Sensor Actuator 9: 73-84) and aminoethyl cellulose (Schulman, S. G., S. Chen, et al. (1995). "Dependence of the fluorescence of immobilized 1-hydroxypyrene-3,6,8-trisulfonate on solution pH: extension of the range of applicability of a pH fluorosensor." Anal Chim Acta 304: 165-170) in the development of fluorescence-based pH sensors that operate in neutral and acidic environments, as well as an intravascular blood gas monitoring system where it was used for both pH and $pCO_2$ detection (Gehrich, J. L., D. W. Lubbers, et al. (1986). "Optical fluorescence and its application to an intravascular blood gas monitoring system." IEE TBio-med Eng BME-33: 117-132). Fiber-optic pH sensors have been described with HPTS bound to an anion exchange membrane (Zhujun, Z. and W. R. Seitz (1984)) or resin (Zhang, S., S. Tanaka, et al. (1995). "Fibre-optical sensor based on fluorescent indicator for monitoring physiological pH values." Med Biol Eng Comput 33: 152-156) and fixed to the tip of the optical fiber.

For example U.S. Pat. No. 5,114,676 (incorporated by reference herein in its entirety) provides a pH sensor with a fluorescent indicator which may be covalently attached to a particle or to a microcrystalline cellulose fiber. The sensor comprises an optically transparent substrate, a thermoplastic layer and a hydrogel. Part of the particle with the indicator attached thereto is imbedded in a thermoplastic layer that is coated on the substrate and mechanically adhered using heat and pressure. The majority of the particle/indicator is imbedded within a hydrogel layer that is applied over the thermoplastic layer. The pH sensor is applied to the tip of an optical waveguide.

Furthermore, with the recent availability of low cost UV LEDs, the dye can be measured with relatively inexpensive instrumentation that combines UV and blue LEDs and a photodiode module. Such a setup has been described (Kostov, Y., P. Harms, et al. (2001). "Low-cost microbioreactor for high-throughput bioprocessing." Biotechnol Bioeng 72: 346-352) to detect the pH of a high throughput microbioreactor system via HPTS directly dissolved in the fermentation media.

In one embodiment of the present invention, the preferred sensing device comprises at least one light source, a detector, and a sensor comprising a fluorescent reporter dye system. In one embodiment, the fluorescent reporter dye system comprises a fluorescent dye operably coupled to an analyte-binding quencher. The dye may be covalently bound to the quencher or merely associated with the quencher. The dye and quencher are preferably operably coupled, which means that in operation, the quencher is in close enough proximity to the dye to interact with and modulate its fluorescence. In one embodiment, the dye and quencher may be constrained together within an analyte-permeable hydrogel or other polymeric matrix. When excited by light of appropriate wavelength, the fluorescent dye emits light (e.g., fluoresces). The intensity of the light is dependent on the extent of quenching which varies with the amount of analyte binding. In other embodiments, the fluorescent dye and the quencher may be covalently attached to hydrogel or other polymeric matrix, instead of to one another.

In one embodiment, a separate pH indicator dye is combined with a different dye that is functionalized with an analyte-binding moiety, such that the two dye system are immobilized together (e.g., in a hydrogel) in the sensor.

Some fluorescent pH indicator molecules absorb light at a particular wavelength and emit light at a second, longer wavelength. Their pH indicating function typically involves protonation and deprotonation. This means that these fluorescent pH indicators include a hydrogen atom (proton, $H^+$) which forms part of the molecule (is bound to the molecule) in one pH range, but within another pH range the proton is dissociated from the molecule. When the proton is disassociated from the molecule, the molecule takes on a negative charge, which is balanced by a positively-charged ion (e.g., $Na^+$) in solution with the indicator. This arrangement is illustrated by Equation 1. $R-H \leftrightarrows R^- + H^+$ Where R represents a fluorescent molecule, it generally will exhibit fluorescence at a different wavelength (will be visible as a very different color) based upon whether it is in the R—H form or in the $R^-$ form. For most molecules represented by R, this change will occur generally quite abruptly within a very narrow pH range, allowing R to serve as a very simple and reliable pH indicator. When placed in solution, it will exhibit one very distinct color (a color associated with its R—H form), and another very distinct color associated with its $R^-$.

For example, 8-Hydroxyl-1,3,6-pyrenetrisulphonate (HPTS) has been considered one of the best potential indicators for pH determination because of its excellent photo-stability, high quantum yield, dual excitation, large Stokes' shift and long fluorescence emission. A desirable feature of this indicator is that the acidic (associated HPTS form) and basic (dissociated $PTS^-$) forms have different excitation wavelengths at 406 and 460 nm, with an isosbestic point at 418 nm, but exhibit a similar fluorescence emission maximum at 515 nm. The dual excitation and single emission make HPTS suitable for ratiometric detection of pH. The fluorescence intensity at 406 nm for the acid form decreases but the intensity at 460 nm for the base form increases as the pH is raised accompanying the conversion of the acidic into basic forms of the dye.

Due to the hydroxyl (—OH) group on dyes such as HPTS and its derivatives, these dyes are sensitive to the pH changes in the environment. The pH-dependent ionization of the hydroxyl group causes these pyranine derivatives to have a pH-dependent absorption spectra with different absorption maxima in its acidic form and basic form. The first absorption maximum is the first excitation wavelength and the second absorption maximum is the second excitation wavelength. The amounts of light absorbed by the fluorescent dye at the first excitation wavelength and the second excitation wavelength depend on or relate to the pH of the medium the fluorescent dye is in contact with. The amount of light emitted by the dye (e.g., the fluorescent emission) at the emission wavelength depends on the amount of light absorption when the dye is irradiated at the excitation wavelength. Since the absorption is affected by the pH of the medium, the fluorescent emission is also affected by the pH. This provides the basis for the pH determination while being able to measure the polyhydroxyl compound concentration.

In one preferred embodiment of the present invention, ratiometric pH sensing is accomplished using an optical sensor comprising at least one excitation light source operably coupled to the proximal end region of an optical fiber, wherein the fiber has disposed along its distal end region within the light path of the fiber, an indicator system configured to generate a detectable emission signal in response to the excitation light. Preferred embodiments of the sensor further comprise optical means for sending the emission signal to a detector. Such optical means are well known in the art, and may involve e.g., a mirror to return light, filters, lens, beam splitters, and optical fiber bundles and split configurations.

In preferred embodiments, the indicator system comprises a fluorophore that exhibits at least two different forms and a pH-dependent shift between these different forms, wherein this shift can be detected as a change in the emission intensity at a single wavelength or at two different wavelengths. For example, one indicator system for ratiometric pH sensing comprises an fluorescent dye (e.g., HPTS) that absorbs light at two different wavelength maxima's ($\lambda_{acid}$ and $\lambda_{base}$) depending on whether the dye is in its acid or base forms, and it emits light at a single longer emission wavelength. More particularly, as pH is increased, HPTS shows an increase in absorbance corresponding to the $\lambda_{base}$ and a decrease in absorbance corresponding to the $\lambda_{acid}$. These changes are due to the pH-dependent ionization of the hydroxyl group. The emission spectrum for HPTS is independent of pH, with a peak emission wavelength of about 511 nm, but the intensity of the emitted light depends on the amount of light absorbed (which varies with pH and the excitation wavelength). So for example, if one excites HPTS at a given pH with light of a first wavelength (e.g., $\lambda_{acid}$), one can measure the emission intensity at the single emission wavelength; the intensity will depend on the form of the dye (i.e., degree of ionization—which depends on the pH). One can also excite at a second wavelength (e.g., $\lambda_{base}$) and measure the emission intensity at the same given pH. The ratio of the emission intensities relates to the pH and is independent on the amount of the dye as well as certain optical artifacts in the system. It is noted that any excitation wavelengths may be used for the ratiometric sensing, but the $\lambda_{acid}$ and $\lambda_{base}$ are preferred in accordance with one embodiment of the invention. The wavelength at which the absorption is the same for the acid and base forms of the dye is called the isobestic point—excitation at this wavelength ($\lambda_{iso}$) may also be used in ratiometric sensing in accordance with other preferred variations to the invention. When a ratio of emission intensities (e.g., $I_{base}/I_{iso}$ or $I_{base}/I_{acid}$) is plotted against pH, a standard or calibration curve is generated (See e.g., FIGS. 3, 5 and 9). The ratiometric method is similar regardless of whether the dye used is a dual exciter—single emitter (like HPTS), or a single exciter—dual emitter, or a dual exciter—dual emitter, as long as the dye undergoes a pH sensitive shift in form that yields a detectable change in spectral property.

Optical Glucose Sensing

Details related to some preferred fluorescent dyes, glucose binding moieties, and methods for optically determining glucose concentrations are disclosed in U.S. Pat. Nos. 5,763,238, 6,653,141, 6,627,177, 5,512,246, 5,137,833, 6,800,451, 6,794,195, 6,804,544, 6,002,954, 6,319,540, 6,766,183, 5,503,770, 7,470,420, 7,968,714, 7,751,863, 7,417,164, 7,767,846, 8,110,251, 8,202,731, 7,939,664, and 8,088,097; each of which is incorporated herein in its entirety by reference thereto.

Lifetime Chemistry

In another embodiment, glucose concentrations can be determined by exploiting the phenomena of fluorescence resonance energy transfer (FRET). FRET is the transfer of energy from a donor fluorophore to an acceptor molecule. FRET occurs when the donor fluorophore, which fluoresces at a wavelength absorbed at least in part by the acceptor molecule, is in close proximity to the acceptor such that the donor fluorophore can transfer energy to the acceptor through molecular interactions. The fluorescence lifetime of the fluorophore, where the fluorescence lifetime is the time the fluorophore remains in the excited state, is altered by FRET. Thus, measuring the fluorescence lifetime of the fluorophore allows one to determine whether the fluorophore is bound to the acceptor.

Lifetime can be measured by using a time-domain method where the fluorophore is excited by a brief pulse of excitation light and the fluorescence intensity is measured over time. The excitation pulse can be a pulse from a laser with a duration in the picoseconds range up to a duration of about a few nanoseconds. In other embodiments, the pulse duration can be greater than about a few nanoseconds. The fluorescence intensity of the fluorophore as a function of time is given by the equation:

$$I(t) = I_0 * \exp(-t/\tau) \qquad \text{Equation A}$$

Figure 14:
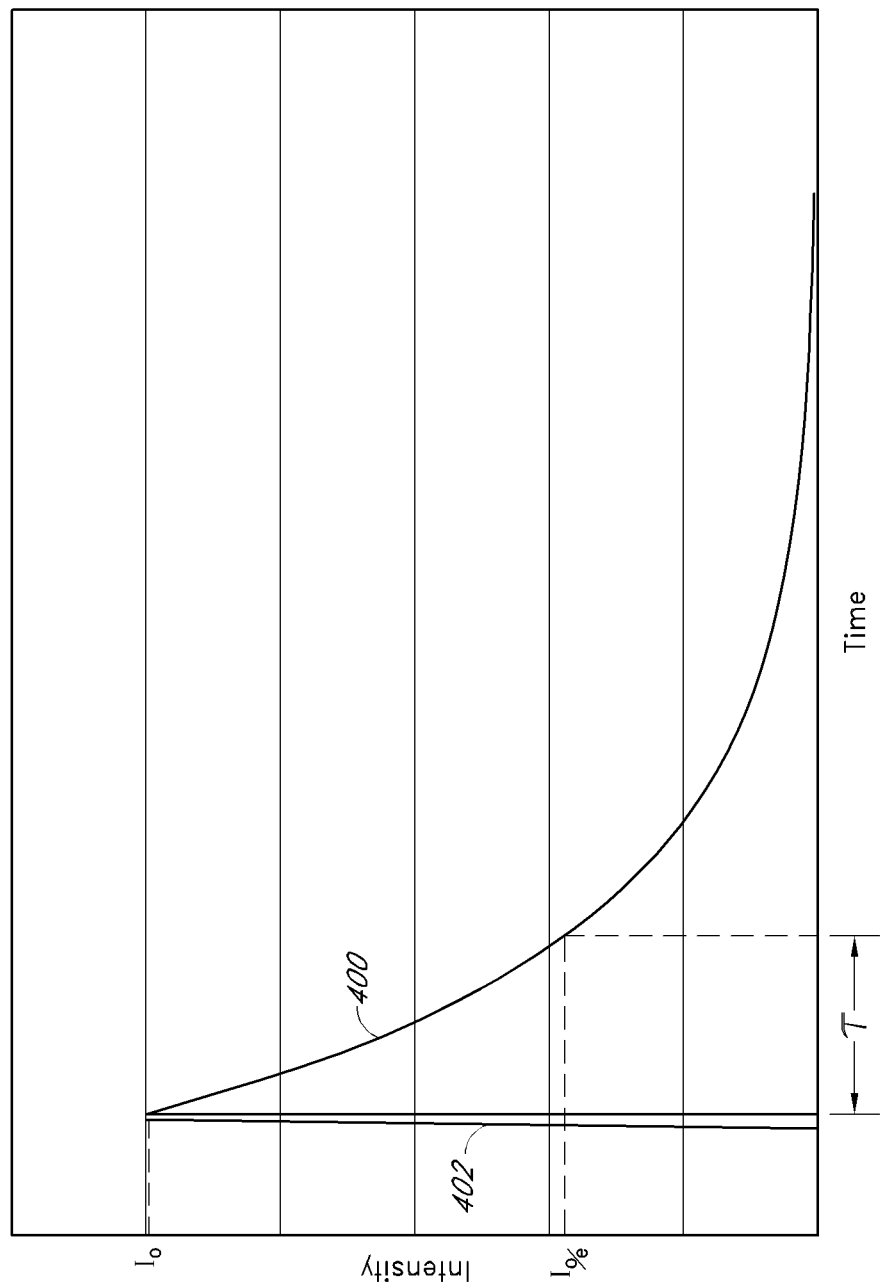
FIG. 14 displays a graph of the decay of the fluorescent emission over time after a pulse of excitation light.

I(t) is the fluorescence intensity at time (t), $I_0$ is the initial intensity after excitation and $\tau$ is the fluorescence lifetime which is defined as the time required for I(t) to decay to $I_0/e$. Equation A is applicable to a fluorophore with a single exponential decay of fluorescence and a lifetime that is substantially longer than the excitation pulse. FIG. 14 shows a graph of the decay of the fluorescent emission 400 over time after a pulse of excitation light 402. The time it takes the initial intensity, $I_0$, to drop to $I_0/e$ is equal to the lifetime, $\tau$.

An alternative method of measuring lifetime is by a frequency-domain method where the fluorophore is excited by a frequency modulated excitation light. The fluorescence lifetime, $\tau$, can be determined by measuring the phase shift of the emission from the fluorophore relative to the excitation light, or by measuring the modulation ratio, using the following equations:

$$\tau_\phi = \omega^{-1} * \tan(\phi) \qquad \text{Equation B}$$

$$\omega = 2\pi f \qquad \text{Equation C}$$

$$\tau_M = \omega^{-1} * (M^{-2} - 1)^{1/2} \qquad \text{Equation D}$$

$$M = \frac{(AC/DC)_{EM}}{(AC/DC)_{EX}} \qquad \text{Equation E}$$

Figure 15:
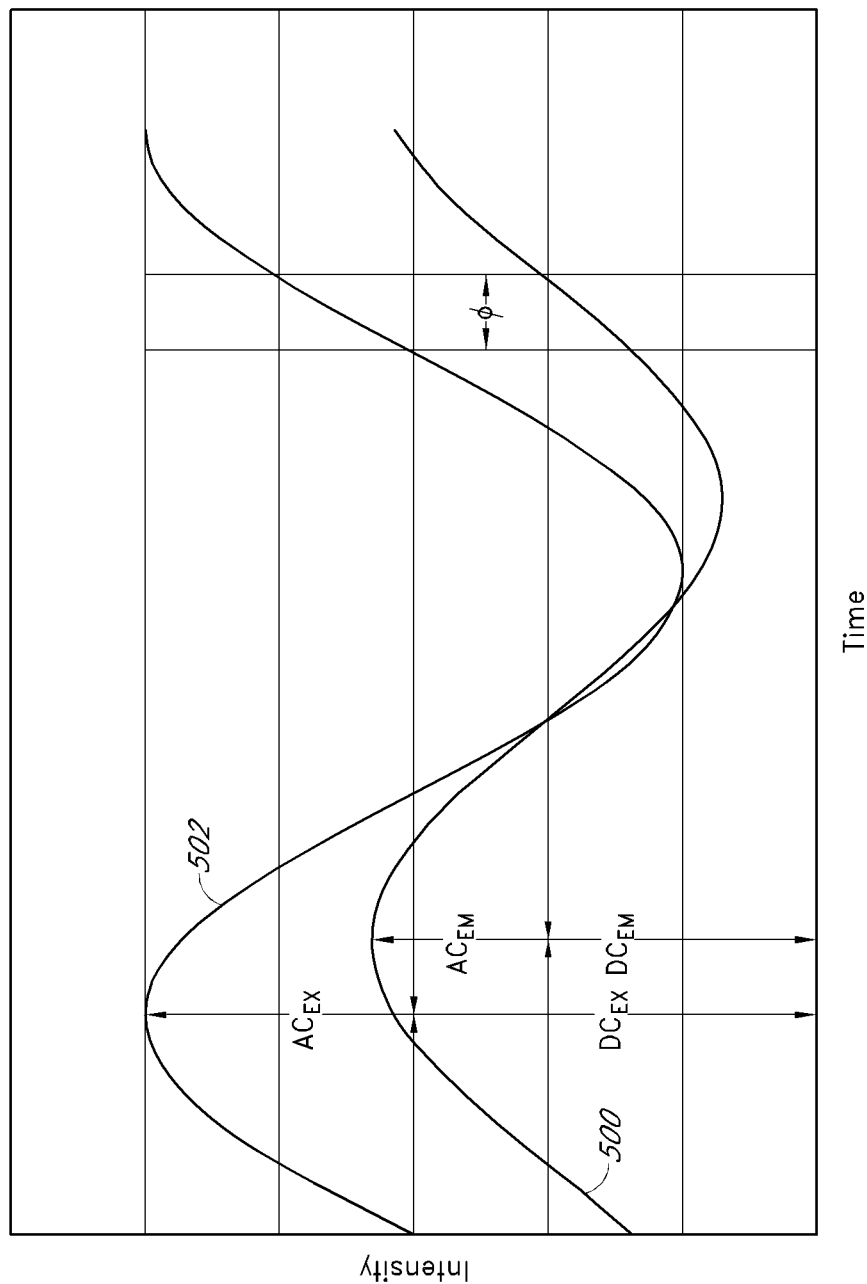
FIG. 15 displays a graph showing the relationship between the emission signal and the excitation signal.

$\tau_\phi$ is the lifetime determined by measuring the phase shift, $\phi$. $\omega$ is the angular frequency of the frequency modulated excitation light and f is the linear frequency. $\tau_M$ is the lifetime determined by measuring the modulation ratio, M. AC is the magnitude of the alternating portion of the signal, or the amplitude of the wave, while DC is the amplitude of the DC portion of the signal. EM refers to the emission signal, and EX refers to the excitation signal. FIG. 15 is a graph showing the relationship between the emission signal 500 and the excitation signal 502 and the variables described in Equations B-E.

Preferred binding assay configurations for use in the sensor include a reversible competitive, reagent limited, binding assay, the components of which include an analyte analog and an analyte binding agent capable of reversibly binding both the analyte of interest and the analyte analog. The analyte of interest and the analyte analog compete for binding to the same binding site on the analyte binding agent. Such competitive binding assay configurations are well known in the art of clinical diagnostics and are described, by way of example, in The Immunoassay Handbook, ed. David Wild, Macmillan Press 1994. Suitable analyte binding agents for use in the assay would include antibodies or antibody fragments which retain an analyte binding site (e.g. Fab fragments), lectins (e.g. concanavalin A), hormone receptors, drug receptors, aptamers and molecularly-imprinted polymers. Preferably the analyte analog should be a substance of higher molecular weight than the analyte such that it cannot freely diffuse out of the sensor. For example, an assay for glucose might employ a high molecular weight glucose polymer such as dextran as the analyte analog.

Suitable optical signals which can be used as an assay readout in accordance with the disclosure include any optical signal which can be generated by a proximity assay, such as those generated by fluorescence resonance energy transfer, fluorescence polarisation, fluorescence quenching, phosphorescence technique, luminescence enhancement, luminescence quenching, diffraction or plasmon resonance.

In some preferred embodiments of the sensor of the disclosure incorporates a competitive, reagent limited binding assay which generates an optical readout using the technique of fluorescence resonance energy transfer. In this assay format the analyte analog is labeled with a first chromophore and the analyte binding agent is labeled with a second chromophore. One of the first and second chromophores acts as a donor chromophore and the other acts as an acceptor chromophore. It is an important feature of the assay that the fluorescence emission spectrum of the donor chromophore overlaps with the absorption spectrum of the acceptor chromophore, such that when the donor and acceptor chromophores are brought into close proximity by the binding agent a proportion of the energy which normally would produce fluorescence emitted by the donor chromophore (following irradiation with incident radiation of a wavelength absorbed by the donor chromophore) will be non radiatively transferred to the adjacent acceptor chromophore, a process known in the art as FRET, with the result that a proportion of the fluorescent signal emitted by the donor chromophore is quenched and, in some instances, that the acceptor chromophore emits fluorescence. Fluorescence resonance energy transfer will generally only occur when the donor and acceptor chromophores are brought into close proximity by the binding of analyte analog to analyte binding agent. Thus, in the presence of analyte, which competes with the analyte analog for binding to the analyte binding agent, the amount of quenching is reduced (resulting in a measurable increase in the intensity of the fluorescent signal emitted by the donor chromophore or a fall in the intensity of the signal emitted by the acceptor chromophore)

as labeled analyte analog is displaced from binding to the analyte binding agent. The intensity or lifetime of the fluorescent signal emitted from the donor chromophore thus correlates with the concentration of analyte in the fluid bathing the sensor.

An additional advantageous feature of the fluorescence resonance energy transfer assay format arises from the fact that any fluorescent signal emitted by the acceptor chromophore following excitation with a beam of incident radiation at a wavelength within the absorption spectrum of the acceptor chromophore is unaffected by the fluorescence resonance energy transfer process. It is therefore possible to use the intensity of the fluorescent signal emitted by the acceptor chromophore as an internal reference signal, for example in continuous calibration of the sensor or to monitor the extent to which the sensor has degraded and thus indicate the need to replace the sensor. As the sensor degrades, the amount of acceptor chromophore present in the sensor will decrease and hence the intensity of fluorescent signal detected upon excitation of the acceptor chromophore will also decrease. The fall of this signal below an acceptable baseline level would indicate the need to implant or inject a fresh sensor. Competitive binding assays using the fluorescence resonance energy transfer technique which are capable of being adapted for use in the sensor of the disclosure are known in the art. U.S. Pat. No. 3,996,345 describes immunoassays employing antibodies and fluorescence resonance energy transfer between a fluorescer-quencher chromophoric pair. Meadows and Schultz (Anal. Chim. Acta (1993 280: pp 21-30) describe a homogeneous assay method for the measurement of glucose based on fluorescence resonance energy transfer between a labeled glucose analog (FITC labeled dextran) and a labeled glucose binding agent (rhodamine labeled concanavalin A). In all of these configurations the acceptor and donor chromophores/quenchers can be linked to either the binding agent or the analyte analog.

Fluorescence lifetime or fluorescence intensity measurements may be made. As described in Lakowitz et al, Analytica Chimica Acta, 271, (1993), 155-164, fluorescence lifetime may be measured by phase modulation techniques.

Figure 16:
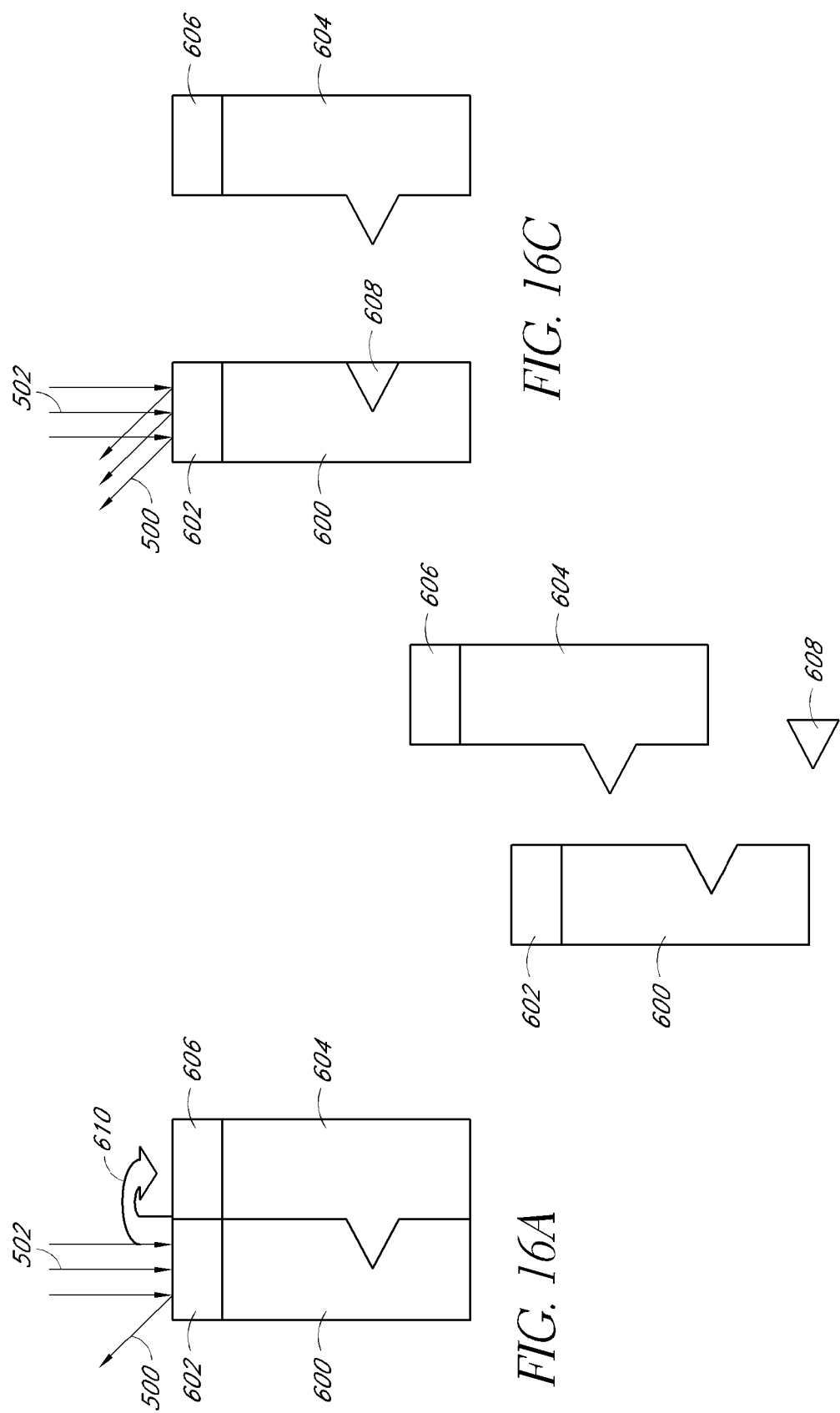
FIGS. 16A, 16B, and 16C schematically illustrate a competitive binding system for measuring glucose using FRET which comprises a glucose binding molecule linked to a donor fluorophore and a glucose analog linked to an acceptor molecule.

In some preferred embodiments as shown in FIGS. 16A, 16B and 16C, a competitive binding system to measure glucose using FRET comprises a glucose binding molecule 600 linked to a donor fluorophore 602 and a glucose analog 604 linked to an acceptor molecule 606. The glucose binding molecule 600 is capable of binding with both glucose 608 and the glucose analog 604. As shown in FIG. 16A, when the glucose analog 604 is bound to the glucose binding molecule 600, the fluorescent emission 500 from the fluorophore 602 is reduced in magnitude and shifted in phase and lifetime by FRET 610 because the fluorophore 502 is in close proximity to the acceptor 606. In other embodiments, the fluorophore 602 is molecule 600.

As shown in FIG. 16B, glucose 608 competes with the glucose analog 604 for the binding site on the glucose binding molecule 600. As shown in FIG. 16C, the glucose molecule 608 can displace the glucose analog 604 from the glucose binding molecule 600 so that the acceptor 606 does not alter the emission lifetime 500 of the fluorophore 602 via FRET 610.

In a system where there are a certain concentration of glucose binding molecules, glucose analogs and glucose molecules, an equilibrium will exist between the number of bound glucose molecules to the number of bound glucose analogs. A change in the number of glucose molecules in the system, changes the equilibrium between bound glucose molecules to bound glucose analogs. This in turn changes the mean lifetime of the fluorophore emission.

In some embodiments, the system is excited by a frequency modulated excitation light less than approximately 1 MHz, between approximately 1 to 200 MHZ, or greater than approximately 200 MHz. In some embodiments, the frequency is approximately 0.05, 0.1, 1, 10, 20, 30, 40, 50, 60, 70, 80, 90, 100, 110, 120, 130, 140, 150, 160, 170, 180, 190 or 200 MHz. By measuring the degree of the phase shift of the system, an average FRET induced phase shift for the system can be determined which corresponds to an average lifetime value for the system as defined by Equations B and C described above. Both the phase shift and the lifetime values can be correlated to the glucose concentration. The magnitude of the phase shift is independent of the amplitude of the emission.

In other embodiments, the system is excited by a pulse and the decay of the fluorescence is measured over time. The lifetime can be determined using Equation A described above, and glucose concentration can be correlated to the lifetime value.

In embodiments, the glucose binding molecule with a donor fluorophore and the glucose analog with an acceptor can be substantially immobilized in the hydrogel described above such that diffusion of the glucose binding molecule and the glucose analog out of the hydrogel is substantially reduced. In addition, the sensor is configured to provide excitation light at a wavelength absorbed by the donor fluorophore as described above. In some embodiments, the excitation light is provided as a short pulse from a laser or a light emitting diode (LED). In other embodiments, the excitation light is frequency modulated. In some embodiments, the frequency modulated excitation light is provided by a laser. In some embodiments the frequency modulated excitation light is provided by a LED. The sensor also has a detector that detects the amplitude of the emission over time and/or the phase shift of the emission and/or the amplitudes of the AC and DC portions of the emission and excitation light. The detector can be a photodetector or multiple photodetectors. The excitation and emission light can be transmitted throughout the sensor via optical fibers.

Dry Insertion of an Analyte Sensor

In some embodiments, the sensor can be configured for insertion into a patient wherein the hydrogel, as described above, is "dry." Specifically, the sensor and hydrogel can be configured to be stored outside of a liquid after packaging and before insertion. Sensors currently on the market are stored in a sterile liquid during packaging and while on the shelf. These sensors come with associated problems, such as breaches in sterility of the liquid, and overall increased manufacturing costs. A dry sensor adds at least the benefit of reducing the time and cost associated with the packaging and storing the sensor prior to use. With a dry hydrogel, no liquid is needed for storage, and therefore adequate hydration is not necessary prior to insertion into a patient. After completing any optional modulation tests, the sensors can be washed (e.g., in an aqueous solution at pH 5. The sensors can then be dried in air at room temperature for a time, for example, about 10 min, 20, min, 30 min, 40 min, 50 min, 1 hour, 2 hours, 3 hours, 4 hours, etc., preferably about 1 hour. Other drying methods may be used including drying over an absorbent, heating, heating under vacuum, lyophilization, etc. The sensors can then be packaged and sterilized. In some embodiments, the sensors are sterilized through EtO sterilization. In some embodiments, the sensors are not wetted again until they are inserted into the physiological fluid in a patient.

The dry hydrogel sensor can be inserted into a patient, for example in the patient's blood stream, tissue, or interstitial fluid, in its dry form. The sensor can be inserted, for example, through a long-term cannula such as a radial artery A-line, or can be inserted through the use of a removable cannula wherein the sensor can be left in the patient after deployment with no additional components. After hydration, the sensor can be calibrated in vivo to determine analyte concentration, and can further be used for continuous analyte sensing. In some embodiments, the sensor can be hydrated after approximately 1 to 2 hours after dry insertion into a patient. In other embodiments, the sensor can be hydrated after about 10, 20, 30, 40, or 50 minutes after insertion into a patient. In vivo hydration time can be varied depending on the chemical properties of the polymer matrix. Once hydrated, sensor can be fully calibrated by a single point in vivo calibration (against an independently measured glucose concentration (e.g., YSI laboratory analyzer), pH and temperature), and does not require any prior factory calibration, although the one-point in vivo calibration can optionally be compared with prior factory calibration data stored, e.g., by EPROM or other memory associated with the sensor—e.g., at the proximal end coupling.

The dry sensor can be used with other system components. For example, a monitor can be connected to the sensor to alert when the sensor is fully hydrated. This can allow for the sensor to be at proper hydration prior to in vivo calibration and analyte sensing. Additionally, the sensor can be attached to an alarm that can perform an auditory or visual clue when the sensor is fully hydrated.

The dry sensor does not require the use of any external calibration equipment, e.g., calibration chambers that had previously been used for calibrating an analyte sensor. For example, the dry sensor does not require the use of a heating chamber, an electrical control, fluid injections, waste bags, tubing, among other external calibration equipment. As described in further detail below, the calibration and sensing can all be done in vivo, thus eliminating the requirements of this external calibration paraphernalia.

In some embodiments, the sensors are optionally factory calibrated prior to drying, sterilizing and packaging. They can be run through a set of glucose parameters, such as 0, 50, 150, 250 glucose concentrations, and using the signal data collected, Michaelis-Menten parameters can be derived, such as those described in U.S. App. Pub. No. 2010/0312483, hereby incorporated by reference in its entirety. This data can be placed on any labeling of the sensors, electronically stored, and/or entered into a monitor at the time the sensor is used.

Sensor Calibration

For the analyte sensors disclosed herein, and in particular the glucose sensors, it has been discovered that the fluorescent response of these sensors to glucose concentration may be calibrated in vivo, such as in a patient's blood stream, instead of using values from a known calibration solution and temperature, such as with a calibration chamber, or factory calibration as is the common procedure. All of the calibration can be done in vivo using reference information taken once from the patient. The reference information can be taken through any measuring procedure such as, for example, home blood sugar monitoring, fingerstick testing, YSI testing, electrodes, arterial blood gas analysis, or any other clinical blood chemistry data analysis. The procedure for taking the reference information is not limiting. The reference information can contain certain patient information such as, for example, glucose levels, pH levels, temperature levels, or other body readings, in any combination.

In some embodiments, glucose and pH levels may be obtained for the reference information. In other embodiments, glucose levels may be obtained for the reference information. The calibration method also avoids multiple blood draws from a patient, which is unique compared to other attempts at in vivo calibration that have been disclosed, therefore reducing discomfort. The new method for in vivo calibration of a sensor and calculating an analyte, specifically glucose in some embodiments, is further described below. It was unexpectedly discovered that a Ln-linear relationship forms between the response of fluorescent intensity of the analyte sensor and the amount of glucose in the system. Particularly, this relationship can be modeled between 50 mg/dL and 250 mg/dL glucose, however these ranges are not limiting. The Ln-linear relationship can be described by equation 1:

$$G = M_{factory} * \text{Ln}(\text{Glu}) + B_{factory} \quad (1)$$

where G is the fluorescent intensity of the system, M is the slope of the straight line approximation at factory "calibration," and B is the intercept at factory "calibration." The factor calibrations can be performed prior to packaging of the sensor and the results of the factory calibration can be delivered along with the sensor. $M_{factory}$ and $B_{factory}$ are derivations from the Ln-linear curve fit to the fluorescence vs. glucose response curve of the system. G can be used to represent the fluorescence of the green signals in the system, either G1 or G2. G1 and G2 represent the fluorescence in the acid and base forms of the fluorophore, as described in detail above. Of course the same Ln-linear transformation described above for factory calibration also applies to the one-point in vivo calibration, wherein that equation is: $G = M * \text{Ln}(\text{Glu}) + B$, where G is the fluorescent intensity of the system, M is the slope of the straight line approximation and B is the intercept.

The Ln-linear relationship described in equation 1 can maintain $R^2$ values of >99.5%, as compared with previously disclosed modified Michaelis-Menten models, such as those described in U.S. App. Pub. No. 2010/0312483, hereby incorporated by reference in its entirety.

The Ln-linear relationship described above can additionally be used to correlate to pH in the system. As the sensor can be used in systems with fluctuating glucose, such as in a bloodstream of a patient, it can become necessary to determine the pH of the system and how it affects the calibrations of the analyte sensor. It has been found that a linear relationship exists between the G1 and G2 values and pH at any temperature. The relationship can be described by equation 2:

$$\frac{G1}{G2} = M_{Glu} * \text{pH} + B_{Glu}. \quad (2)$$

In equation 2, M and B are functions of glucose levels in the system. These values were determined through empirical data. M, the slope of the equation, can be defined as equation 3:

$$M_{Glu} = 0.313 + (0.051) * \frac{(240 - Glu)}{190}. \quad (3)$$

Likewise, B, the intercept of the equation, can be defined as equation 4:

$$B_{Glu} = -1.335 - (0.3375) * \frac{(240 - Glu)}{190}. \quad (4)$$

Figure 17:
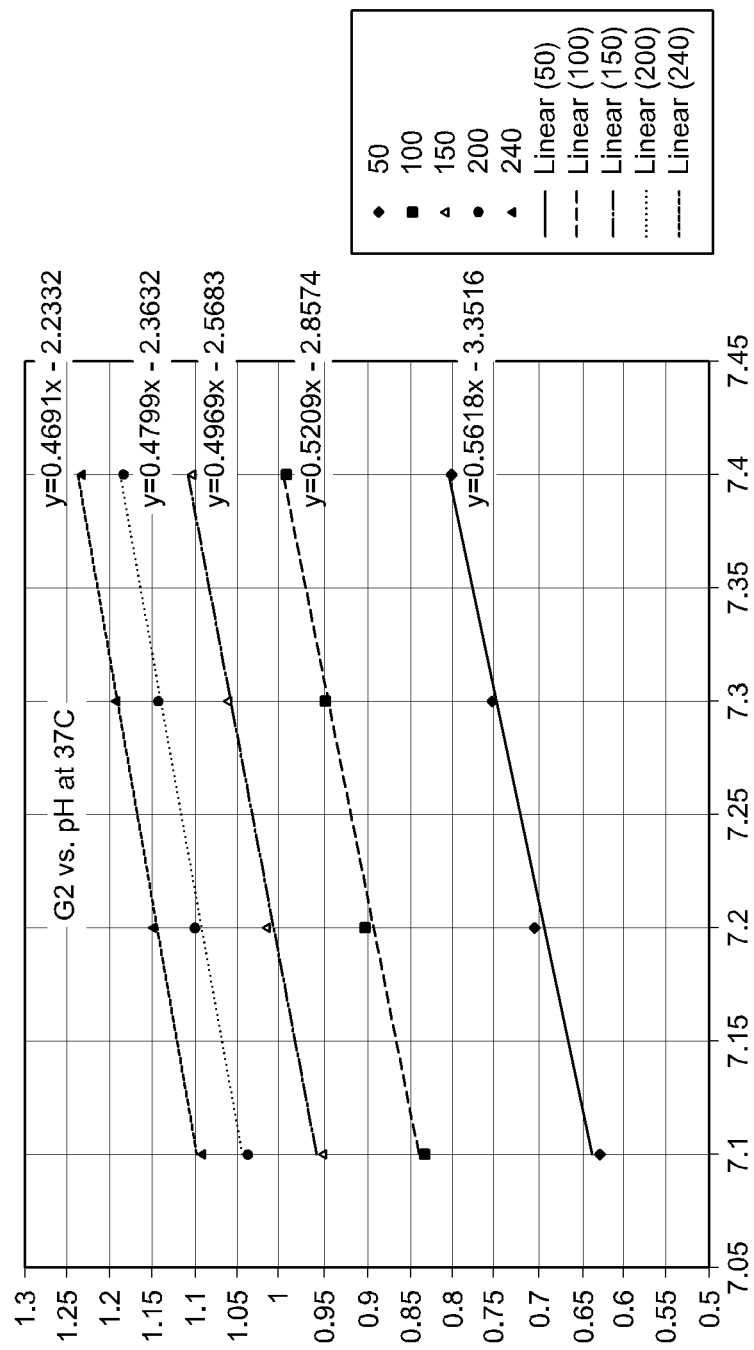
FIG. 17 depicts the Ln-linear relationship between G2 and pH at 37 C at different glucose concentrations.

G2 can also vary with pH as well as glucose. This relationship of G2 with pH has been shown to be virtually linear. FIG. 17 illustrates the linear relationship between G2 and pH. As illustrated in FIG. 17, the lines shown are nearly parallel and linear. However, both the slop of the plotted lines and their intercept change with respect to the levels of glucose in the system.

Because of G2's variance with glucose, the generic form of G2 with pH can be defined as equation 5:

$$G2 = M_{pH} * pH + B_{pH}. \quad (5)$$

Based on FIG. 17, $M_{ph}$ can be defined as equation 6 and B can be defined as equation 7:

$$M_{pH} = 0.4691 + 0.0927 * \frac{(240 - Glu)}{190} \quad (6)$$

and $$B_{pH} = -2.2332 - 1.1184 * \frac{(240 - Glu)}{190}. \quad (7)$$

Equations 6 and 7 can provide for a basis for a first pass estimate of the $G2_{io}$ value, representing the initial fluorescence of G2, based on the pH and glucose values, specifically those values determined in vivo at the time of sensor calibration.

Figure 18:
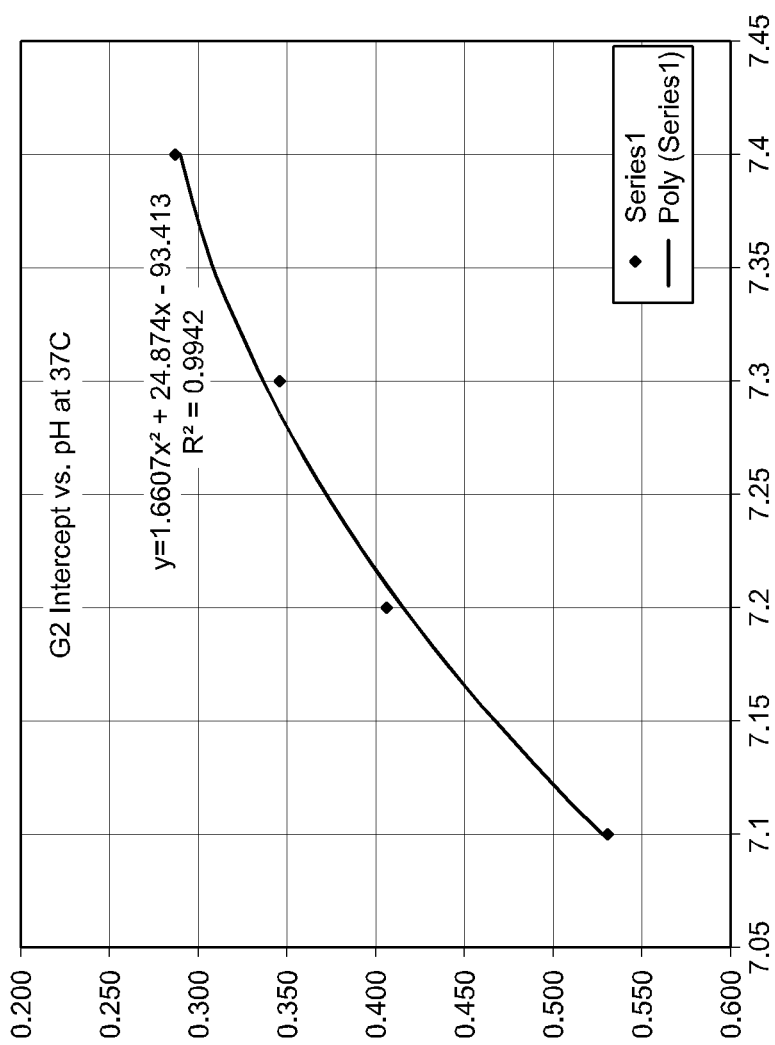
FIG. 18 depicts the relationship between the G2 intercept and pH at 37 C for a range of applicable glucose concentrations.
Figure 19:
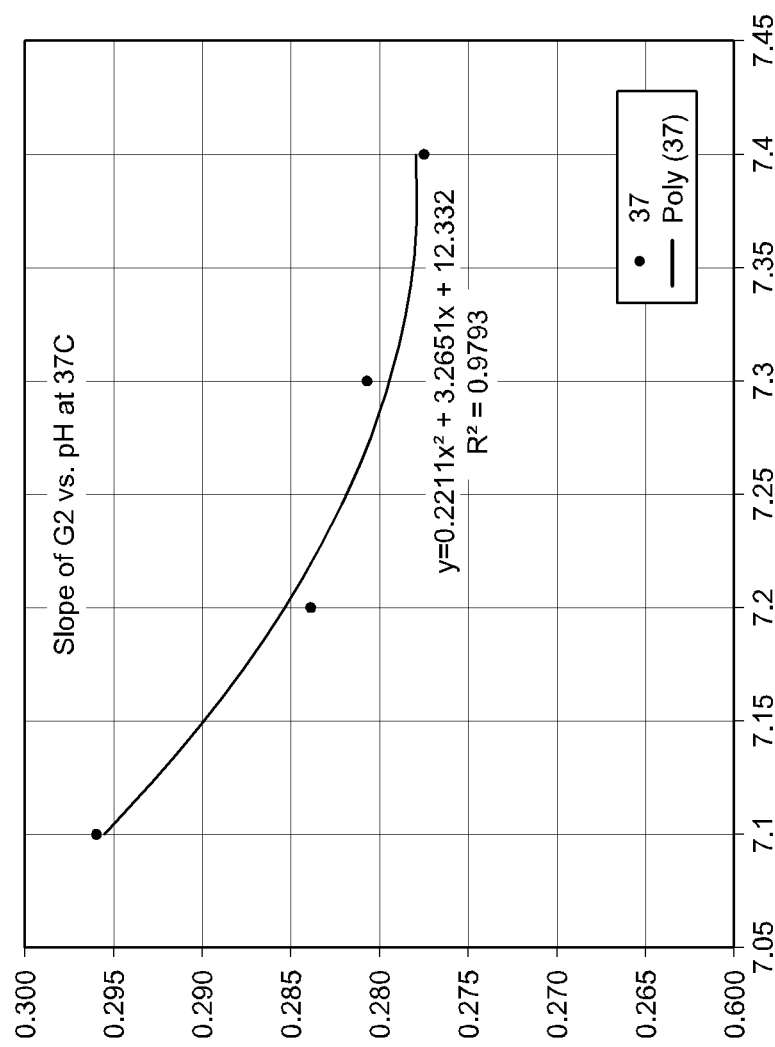
FIG. 19 depicts the relationship between the slope of G2 and pH at 37 for a range of applicable glucose concentrations.

Additionally, we can determine how the slope of G2 varies with pH, as well as the intercept. FIGS. 18 and 19 illustrate the plot of the intercept of G2 and the slope of G2, respectively, vs. pH at a given temperatures. These figures are based on the Ln-linear slope and intercept relationship between fluorescent intensity and glucose concentration. The slope and intercept values for G2 with respect to pH can be defined as equations 8 and 9:

$$M_{G2(pH)} = 0.221 * (pH)^2 - 3.265 * pH + 12.33 \quad (8)$$

and $$B_{G2(pH)} = 1.661 * (pH)^2 + 24.87 * pH - 93.41. \quad (9)$$

Collectively, these equations can describe the underlying methodology for establishing initial intensity, $I_o$, values and a method for tracking glucose in a patient.

Temperature Compensation

While the above equations provide for the calibration of an analyte sensor, such as a glucose sensor, another factor that may be considered is temperature compensation. Analyte sensors, such as the dry insertion analyte sensor disclosed herein, can comprise a thermocouple, or any other temperature sensing device such as a thermistor, to take temperature readings in a patient. The temperature of the sensor can cause fluctuations in the analyte readings, which can be removed by the use of temperature compensation. The temperature coefficient for G2 can vary from approximately 0.5 to 1%/° C., more preferably approximately 0.8%/° C. The temperature coefficient for G1 can vary from approximately 0.5 to 1%/° C., more preferably approximately 0.65%/° C. However, these temperature coefficients can vary based on the values of pH and glucose in the system, and these values are not limiting. For purposes of the below equations, the preferable values are used.

The temperature compensation for G1 and G2 is based on adjusting them to their "equivalent' at 37° C., since that is the temperature upon which the original Michaelis-Menten equations (See e.g., U.S. App. Pub. No. 2010/0312483) were based, and also on the "nominal" body temperature. The compensation for G2 can be defined as equation 10:

$$G2_c = \frac{G2_t}{((-.008 * t) + 1.3553)} \quad (10)$$

where $G2_c$ is the "corrected" value of G2, taking into account temperature, and $G2_t$ is the current value for G2 as measured.

The compensation for G1 can be defined as equation 11:

$$G1_c = \frac{G1_t}{((-.0065 * t) + 1.251)} \quad (11)$$

where $G1_c$ is the "corrected" value of G1, taking into account temperature, and $G1_t$ is the current value for G1 as measured. For both equation 10 and 11, t is a weighted average of thermocouple values in the system. In some equations, this could a 2, 3, 4, 5, 6, 7, 8, 9, or 10 point weighted average, but this is non-limiting and other point weighted averages could be used.

Methods for Calibrating Sensor

Disclosed herein are methods for determining values of the Ln-Linear equations described above used to relate the fluorescent intensity measured by an analyte sensor to the analyte concentration surrounding the sensor. The sensor can be calibrated entirely in vivo. In certain such methods the analyte is glucose, and the glucose sensor is more particularly a GluCath sensor. A GluCath sensor is an optical glucose sensor comprising a chemical indicator system having a fluorophore dye (preferably HPTS-triCys-MA), an analyte binding moiety (preferably 3,3'-oBBV), and an immobilizing means (dye and binding moiety monomers are preferably copolymerized with HEMA and PEGDMA to obtain a hydrogel). In certain such methods, Ln-Linear equations are determined in reference to an analyte sensors based on lifetime chemistry. However, in the description of the methods that follows, reference will be made to a glucose sensor or more particularly a GluCath sensor. Nevertheless, it should be understood that the disclosed methods may be used to calibrate any analyte sensor which may be modeled using the Ln-linear equation.

Methods described below involve a combination of experimental measurement and numerical calculation to establish the appropriate values of the Ln-linear equation describing the sensor response to glucose. As in many chemical systems, the response of the GluCath sensor chemistry is sensitive to other chemical parameters in addition to the analyte of interest. For example, temperature compensation is described above.

In some embodiments, the analyte sensor can be calibrating using the computation values at certain times. In some embodiments, two times can be used, a "draw" time, which refers to the time when a blood is sampled from the patient, and the "applied" time, which refers to the time when the sensor is to be calibrated using the disclosed Ln-linear equation. The samples taken from the patient during the draw time can include valuations of different physiological levels, such as glucose and pH levels at the draw time. The samples taken at the draw time can be tested with, for example, the YSI detection method, known in the art, to analyze the physiological levels.

Using the blood sampled from the patient at the draw time, the slope and intercept of G2 vs. pH can be found from equations 6 and 7. The slope and intercept can then be substituted into equation 5, along with the pH obtained at the draw time. From equation 5, the value of $G2_{io}$, the initial G2 fluorescence, can be obtained as defined in equation 12:

$$G2_{io} = \frac{G2}{M*\text{pH} + B}. \quad (12)$$

Once the initial value of G2 is determined, the ratio of $G2/G2_{io}$ can be calculated for all measurements from the apply time forward. Equation 10 can be applied to the $G2/G2_{io}$ ratio to compute the ratio with temperature compensation.

As $G2_{io}$ has now been established, equations 2, 3, and 4 can be applied to calculate $G1_{io}$, the initial G1 fluorescence, in a similar manner to the method of calculating $G2_{io}$. First, the M and B can be calculated using equations 3 and 4, and then using pH for the draw time, $G1_{io}$ can be calculated using equation 2. Once $G1_{io}$ has been calculated, the ratio $G1/G1_{io}$ can also be calculated from the apply time. Once the ratio is calculated, equation 11 can be applied to $G1/G1_{io}$ to compute the ratio with temperature compensation.

Once the two temperature compensated ratios have been equated, the ratios can be computed used the equation defined by equation 13:

$$\sqrt{\frac{G1}{G1io}} \sqrt{\frac{G2}{G2io}}. \quad (13)$$

This ratio can be calibrated by using, for example, a calibration constant or pH scale factor. As one example, the scale factor can be defined by equation 14:

$$[SF]\text{pH} = \text{pH}/(\text{eq}13) \quad (14)$$

where the pH value is the same pH value that was obtained at the draw time. The $SF_{pH}$ can then be applied to equation 13 to provide a point by point estimate of pH.

As pH has now been established, equations 8 and 9 can be used to compute M (slope) and B (offset) in the Ln-linear equation for glucose as defined in equation 1. By using the results of the above equations, a calibration factor for glucose can be determined, and can be defined in equation 15:

$$CALglu = \frac{Glucal}{\exp(\text{Ln}(glucal))} \quad (15)$$

where CALglu is the calibration factor, Glucal is the value of glucose at the draw time, and Ln(glucalc) is the natural logarithm of the glucose value at the draw time.

The calibration factor, CALglu, can then be applied at the apply time and forward, therefore providing an accurate sensor calibration for continued analyte sensing.

Furthermore, the analyte sensor can be recalibrated by approximately the same process as described above. $I_o$ can be reestablished for both G2 and G1, and the above equations can then calculated to obtain another CALglu calibration factor.

Figure 20:
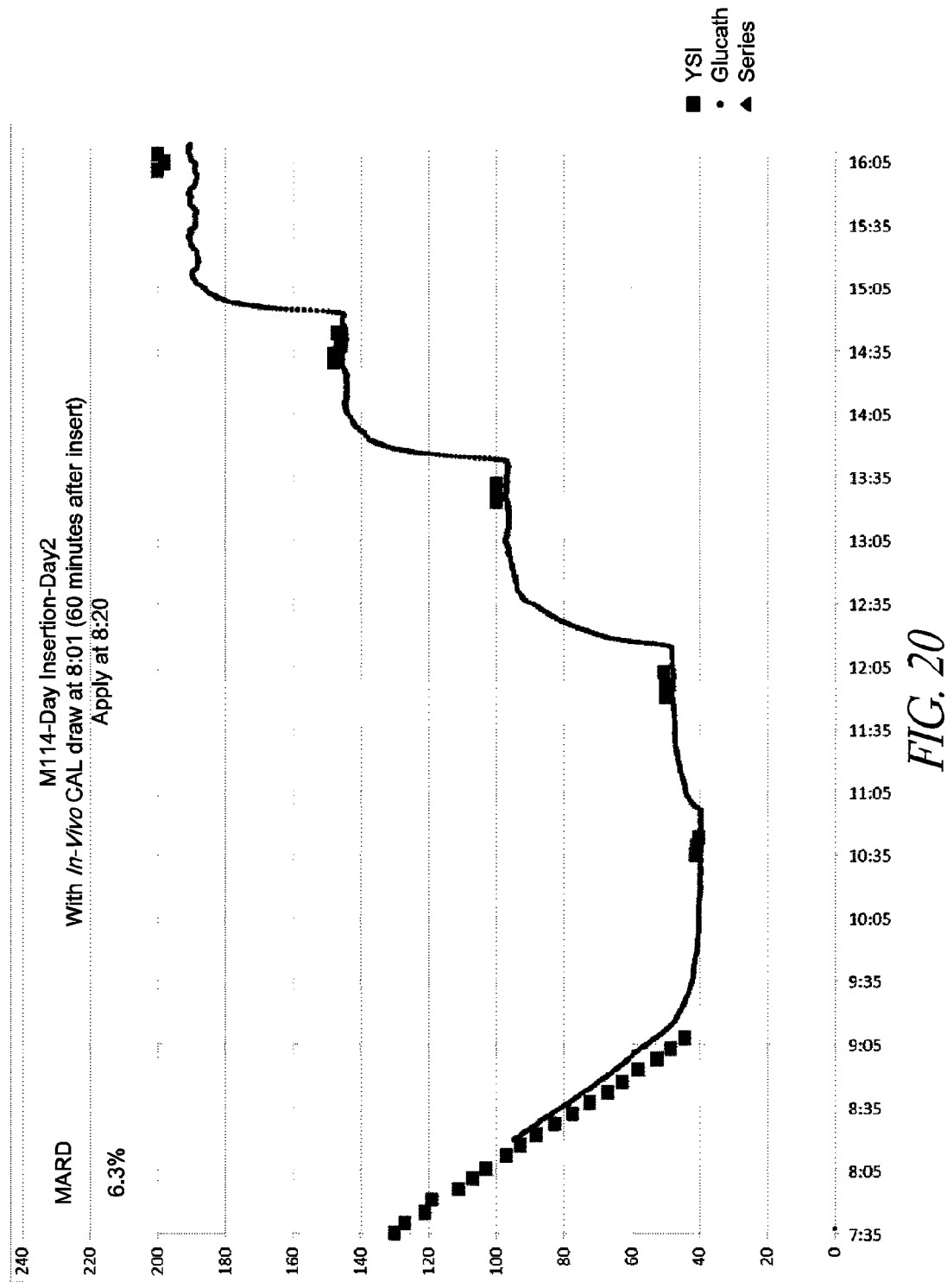
FIG. 20 compares the glucose determinations using a dry inserted optical glucose sensor with one-point in vivo calibration and the YSI laboratory analyzer.

With reference to FIG. 20, the results of glucose determination over time and with infused glucose in an in-vitro study are compared for a continuous glucose sensor in accordance with a preferred embodiment of the present disclosure (-GluCath) and the Yellow Springs Instrument glucose oxidase lab analyzer (●YSI), the gold standard of blood glucose measurements. The sensor used the Ln-linear equation for calibration with a draw time at 8:01 and an apply time at 8:20. The draw was taken approximately 60 minutes after insertion of the sensor into a patient. The GluCath equilibrium fluorescence glucose sensor used in this experiment comprised HPTS-triCysMA dye and 3,3'-oBBV glucose binding moiety. FIG. 20 shows an 8 hr time course with changes in circulating glucose in the range of 40-200 mg/dl. The data show that the equilibrium fluorescence glucose sensor provides continuous monitoring of blood glucose which is as accurate as the YSI lab analyzer. Additionally, FIG. 20 illustrates that even with declining levels of glucose, the sensor calibrates and tracks consistently.

Figure 21:
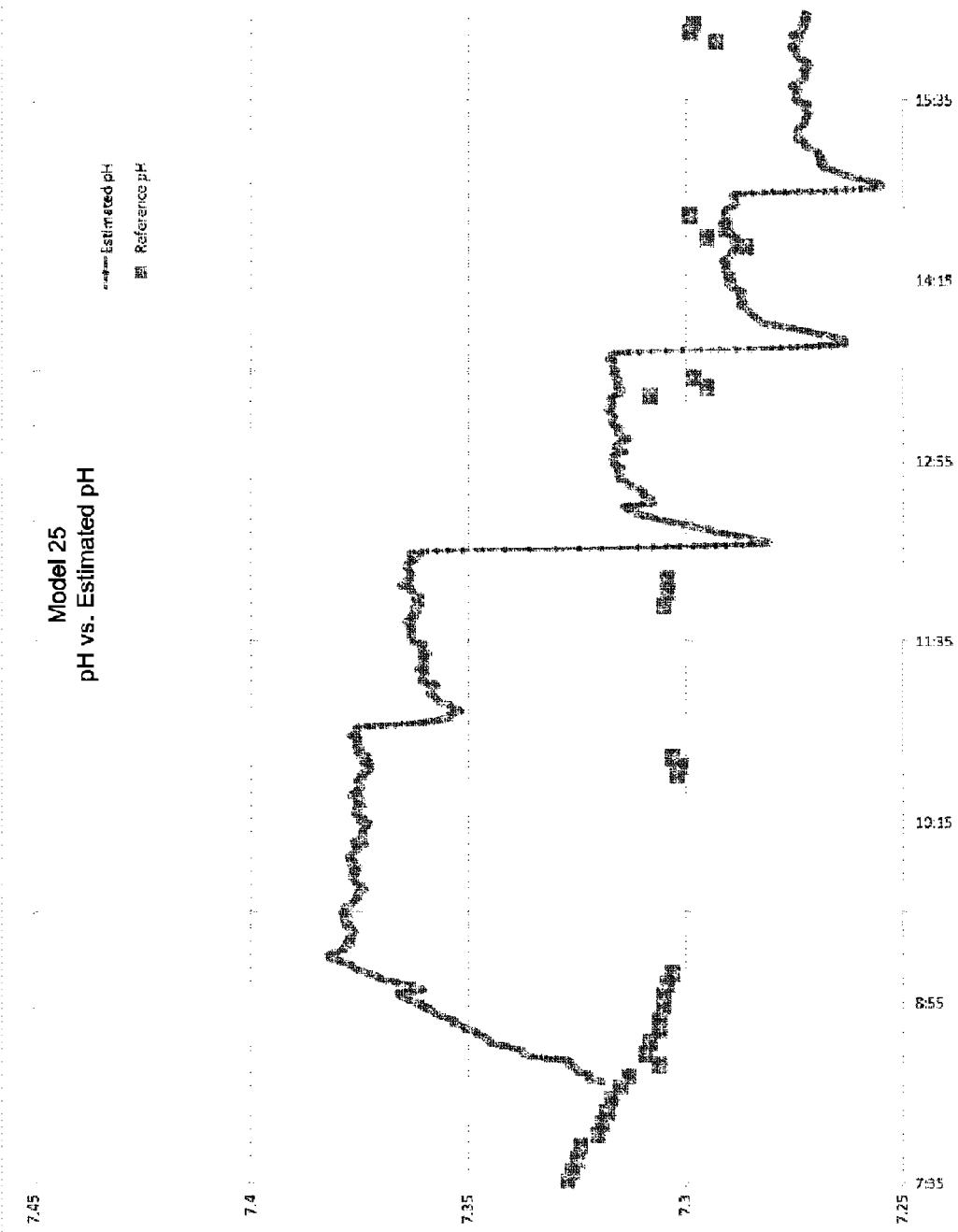
FIG. 21 compares the ratiometric pH estimation using a dry inserted optical glucose sensor and a laboratory pH meter (reference pH).

With reference to FIG. 21, the results of pH determination over time are compared to a reference pH (laboratory pH meter). The graph shows a range of pH from 7.25 to 7.4, a very minimal range, and shows an 8 hr. time course. As illustrated in the figure, the equations disclosed above track very well with the reference pH, with only minimal errors of less than 0.1 pH.

Figure 22:
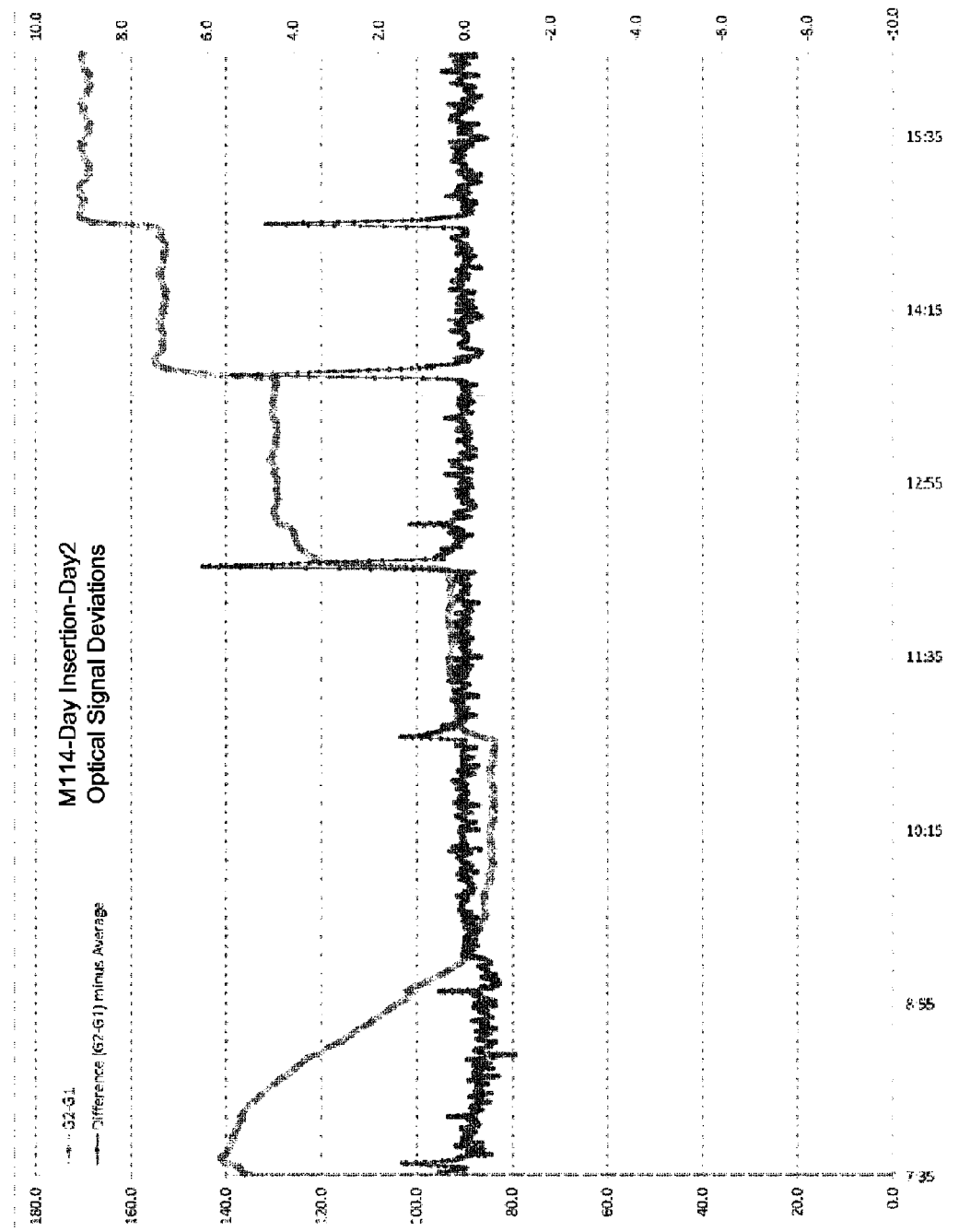
FIG. 22 is a plot of the difference between G2 and G1, and that difference minus the average.

With reference to FIG. 22, G1 and G2 illustrate how the raw signals change over the course of a simulated run of calibration. These values can be used for signal quality metrics, including for error warnings or bad signal indicators.

Figure 23:
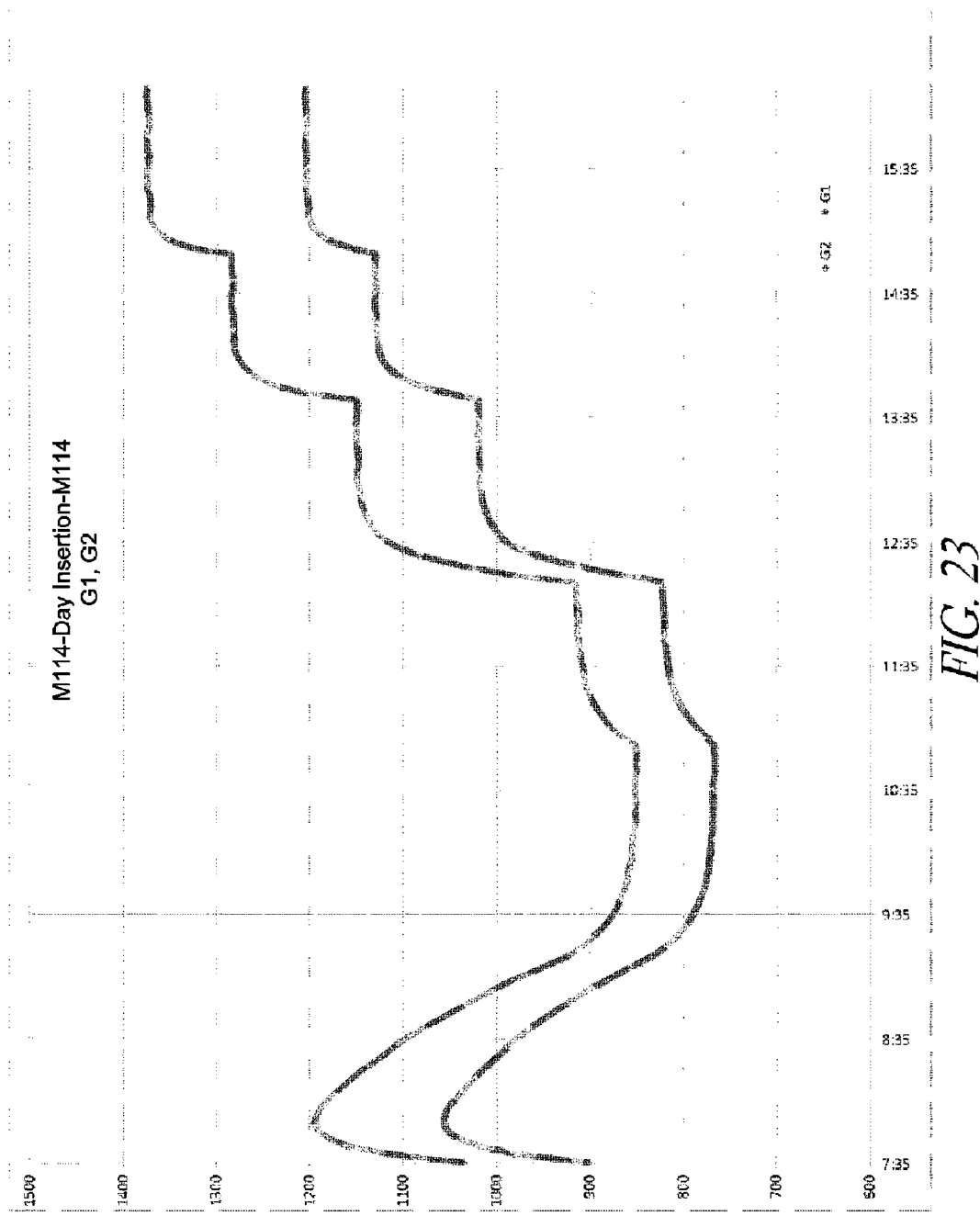
FIG. 23 compares the ratiometric pH estimation using a dry inserted optical glucose sensor and a laboratory pH meter (reference pH).

FIG. 23 illustrates the fluorescent wavelengths of G1 and G2, the acid and base forms of the fluorophore. These values can be used for signal quality metrics, including for error warnings or bad signal indicators.

Figure 24:
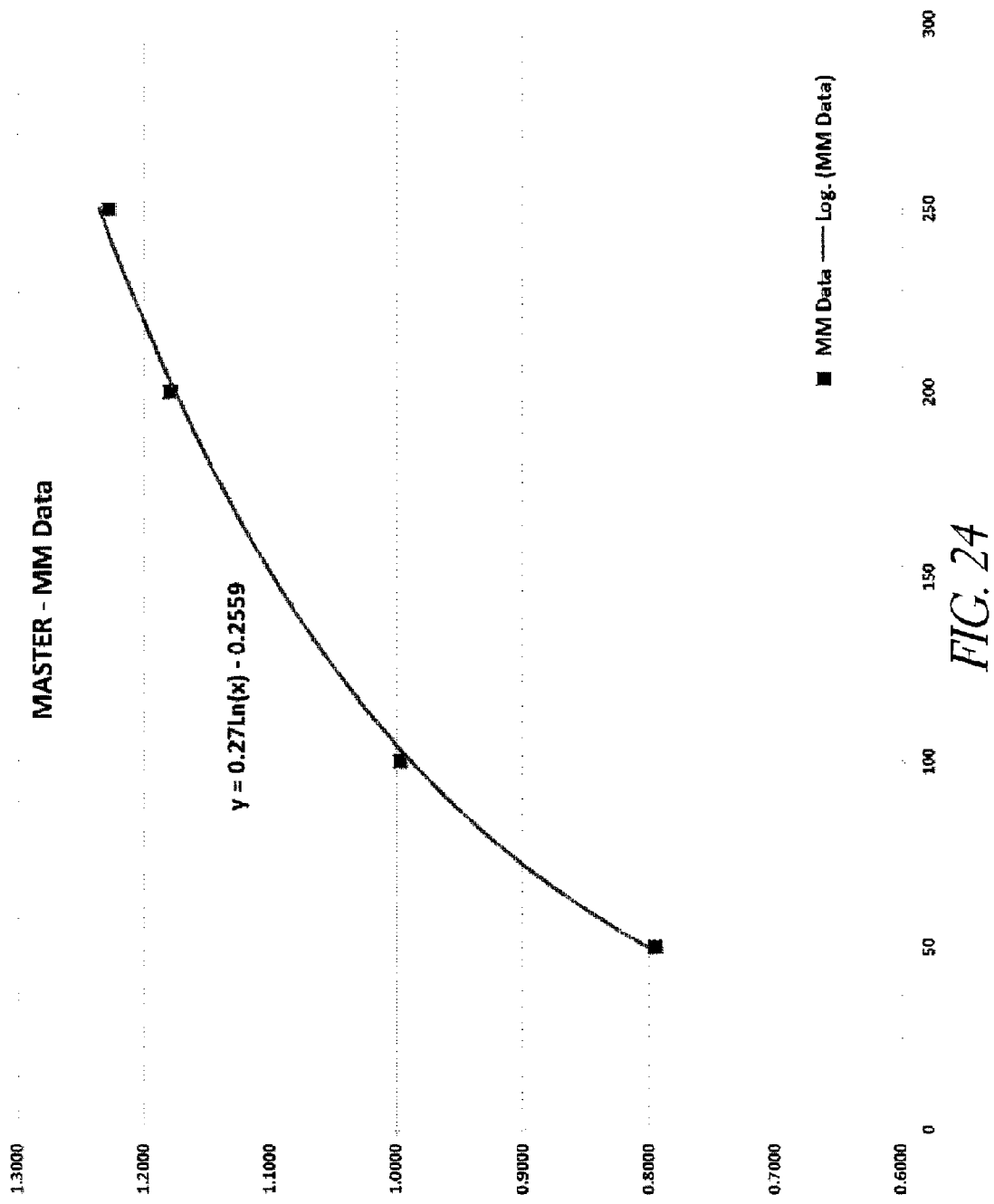
FIG. 24 is a plot of the correlation of the Ln-linear method to a modified Michaelis-Menten equation.

FIG. 24 illustrates the close correlation of the Ln-linear transformation method to the modified Michaelis-Menten transformation method, discussed above. As shown, the correlation for almost every sensor is >99.5%, demonstrating the effectiveness of the simpler Ln-linear equation for determining glucose.

Figure 25:
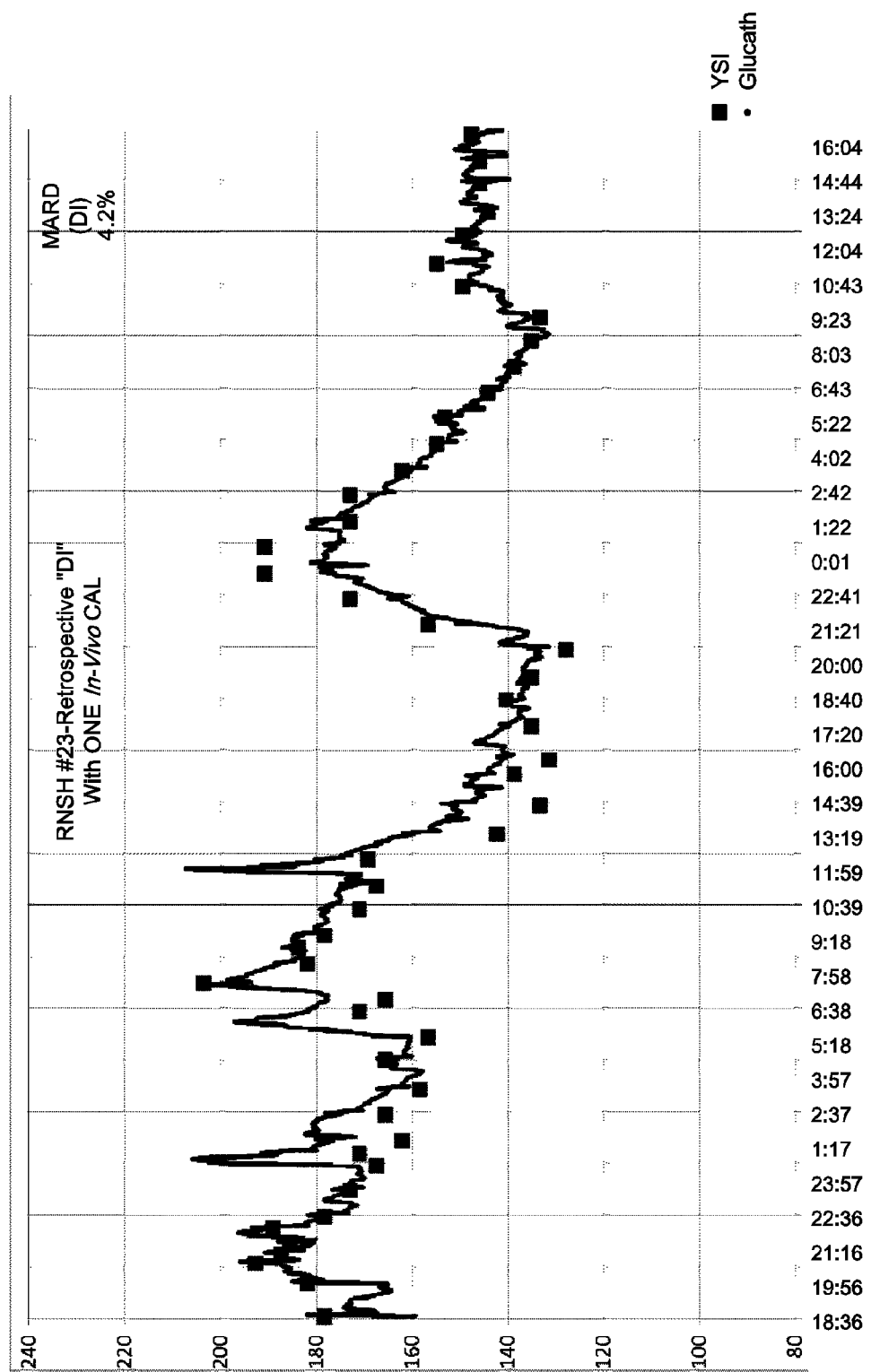
FIG. 25 is a test case showing glucose concentrations determined using a dry-inserted optical glucose sensor with one-point in vivo calibration compared with the glucose concentrations determined using the YSI laboratory analyzer.
Figure 26:
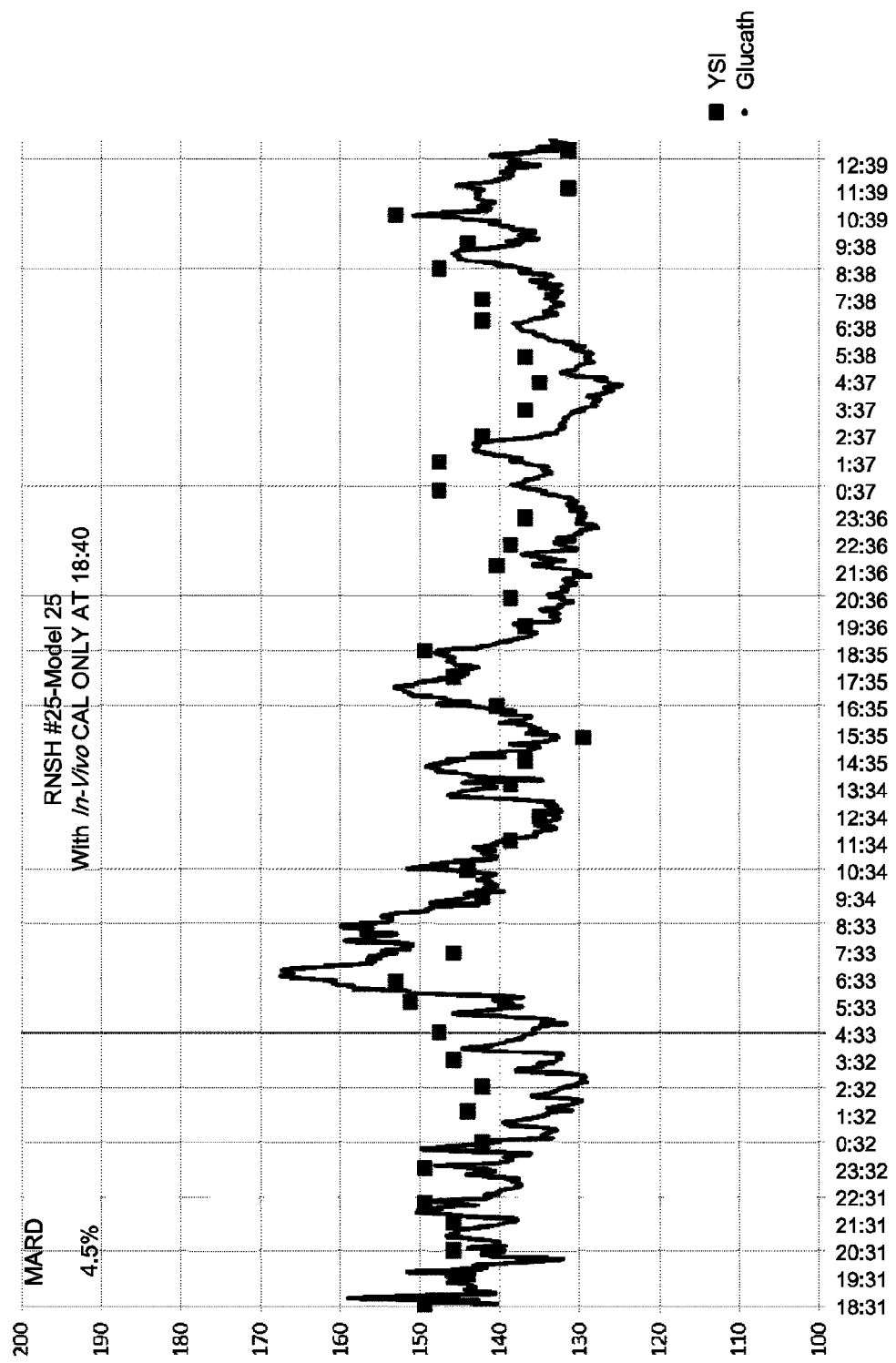
FIG. 26 is another test case showing glucose concentrations determined using a dry-inserted optical glucose sensor with one-point in vivo calibration compared with the glucose concentrations determined using the YSI laboratory analyzer.

Additional data are shown with reference to FIGS. 25 and 26, illustrating in vivo testing in humans. The dry sensor was inserted intravascularly into a patient and was indwelling for about 5-6 hours before testing began. A single calibration was taken at the beginning of the test, as discussed above, but no further recalibrations were made. Again, as shown, the sensor tracks well with the YSI lab analyzer. All values were derived "in vivo" in the system, thus avoiding the need for a calibration chamber.

Implementation into an Analyte Monitoring System

In some embodiments, an analyte sensor can be functionally connected to an analyte monitor. In various embodiments, the analyte monitor can convert fluorescence readings to analyte measurements, display analyte readings, transmit analyte readings, store analyte readings, compare analyte readings, or some combination of these functions. Keyboard or data entry subsystems can be functionally attached to or integrated into a monitor. Various parts can be interconnected by wire, cable, and/or wireless connections, and involve electrical, optical, radio signals, or other appropriate techniques.

The monitor can utilize one or more values of the calibration equations and the correction factor CALglu. In some embodiments, values of calibration equations can be preloaded into the monitor, such as by storing one or more value in memory, whether by the user or another party. In some embodiments, one or more values of the calibration equations can be entered after following a calibration procedure, either with the analyte sensor functionally connected to the monitor or with the analyte sensor connected to a different monitor or reading device. In some embodiments, when a different monitor or reading device is used for calibration, information relating to the calibration can be communicated directly or indirectly between the monitor and the different monitor or reading device functionally connected to the analyte sensor during calibration. In some embodiments, the monitor will receive information relating to the measurement of analyte concentrations as determined with a different device or by a different technique, and use the information during calibration. In some instances, the information can be sent to the monitor with manual entry, such as by keyboard or touchscreen or other manual methods; or by direct or indirect communication with a separate device determining the analyte concentration; or by reading values from an information storage medium such as scanning written or printed information, scanning barcodes, reading magnetic, optical, or computer storage medium including disks, strips, RAM, flash drives, etc.

In some embodiments, the calibration can be performed with purchased or prepared standards, including those with known concentrations of analyte or causing a response by the analyte sensor that is correlatable to analyte levels. In some embodiments, the purchased or prepared standard can include information, such as recorded on a tag, label, inclosure, etc. that is read by the monitor or a device functionally connected to the monitor.

In some embodiments, a monitor can have multiple sets of calibration values stored in memory. Different values can be associated with different sensors, different classes of sensors, different types of sensors, different types of displays, and different types of analyte reading correlation, such as to correlate with a particular brand of analyzer or for analysis performed by a particular methodology. Transition between different calibration values can be by switch, soft switch, jumper, secure connector, or other appropriate techniques. Security protocols and/or access limiting techniques can be utilized to prevent inadvertent or an authorized changing of calibration values.

In some embodiments, the monitor can be a dedicated monitor, such as for a single sensor for a single analyte determination. In some embodiments, the monitor can be a multiuse device which includes other patient monitoring and/or data storage functions, or the analyte monitoring function can be integrated into a patient monitoring system used for monitoring other conditions.

In some embodiments, a monitor can include a computer or microprocessor adapted for use with fluorometric analyte measurements with software or firmware capable of utilizing a Ln-linear equation as a part of a determination of analyte levels, or, in addition, utilizing correction factors to determine analyte levels, as described above. In some embodiments, a monitor capable of determining the values of these parameters can be utilized.

In some embodiments, the monitoring system can be integrated into a network including other devices such as additional monitors, displays including remote displays, televisions, data entry locations, computers, PDAs, telephones, monitoring stations, doctor offices, hospitals, etc. Networking can be via the Internet, local area network, wide-area network, secure network, private network, etc.

Use with Particular Types of Analyte Sensors

In some embodiments, the calibration techniques and methods described herein may be utilized with fluorescence-based analyte sensors, such as those having a fluorophore functionally connected to an amine and a derivative of boronic, arsenious, or germanic acid (including derivatives of their salts) and those having a fluorophore functionally connected to a derivative of boronic, arsenious, or germanic acid (including derivatives of their salts), as described above. In particular embodiments, a fluorescence-based analyte sensor can have a fluorophore that exists in at least two different forms depending on the concentration of a second analyte, such as where these two different forms of the fluorophore fluoresce at different wavelengths. The sensor can also include a binding moiety that binds a first analyte, and the binding moiety can be operably coupled to the fluorophore and causes an optical change in the apparent concentration of the fluorophore related to concentration of the first analyte. The fluorophore can be a fluorescent dye and it can be a fluorescent dye that is a discrete compound or part of a larger molecule. Exemplary materials that can be used as the fluorophore include HPTS-CysMA and HPTS-LysMA. In one embodiment, the binding moiety comprises a quencher, which can change or eliminate fluorescence from a fluorescent dye, in a binding region which can reversibly bind the first analyte. Exemplary materials that can be used as the binding moiety include viologen, compounds comprising a benzylboronic acid group, and compounds comprising a viologen-boronic acid adduct. In another embodiment, the binding moiety includes 3,3'-oBBV and derivatives thereof. Embodiments include those fluorescence-based sensors able to measure glucose levels in fluids including blood. Suitable sensors include those described in U.S. patent application Ser. Nos. 11/671,880 and 12/027,158.

In some embodiments, the calibration techniques and methods described herein may be utilized with analyte sensors based on lifetime chemistry as described above.

Calibration Accuracy

In some embodiments, the objective of a calibration can be to linearize the signal readings in relation to the analyte levels, with far less emphasis on obtaining analyte measurements that are deemed "correct" or in agreement with other analyses. Linearization alone can be of use in various situations including those where relative values over time are of interest as well as for other reasons.

In some embodiments, the objective of the calibration can be to determine the actual value of an analyte concentration or to obtain analyte level measurements that are in agreement with measurements taken by another sensor, method, or instrument. In some preferred embodiments, the objective of the calibration can be to linearize the readings, i.e. convert the readings to a form that more closely approximates a line when plotted against the concentration of analyte present or determined as present, and to relate them to readings from other instruments or techniques that can be linearized also. In some preferred embodiments, the readings may be linearized or are linearizable over a particular range. One way to gauge the agreement between the measurements taken by different sensors, methods, or instruments (or the measurement and a value accepted as correct) is to determine the percentage difference between the readings (or reading and value), which is the difference between the two readings (or the reading and the value) divided by their average.

In some embodiments, the agreement or accuracy is more desirable for readings within a particular range than for readings outside of that range. For physiological parameters, a desirable range for readings can be described as a region around a normal reading for the parameter, although what is "normal" will tend to vary somewhat between individuals, situations, and with time. While a calibration for an analyte sensor can be performed over a very broad range, a calibration can also be performed over a more limited range such as by selecting standard calibration solutions that are within about 5%, 10%, 25%, 50%, 100%, 200%, 400%, or about 600% of a normal or target value.

Continuous Glucose Monitoring System

Figure 27:
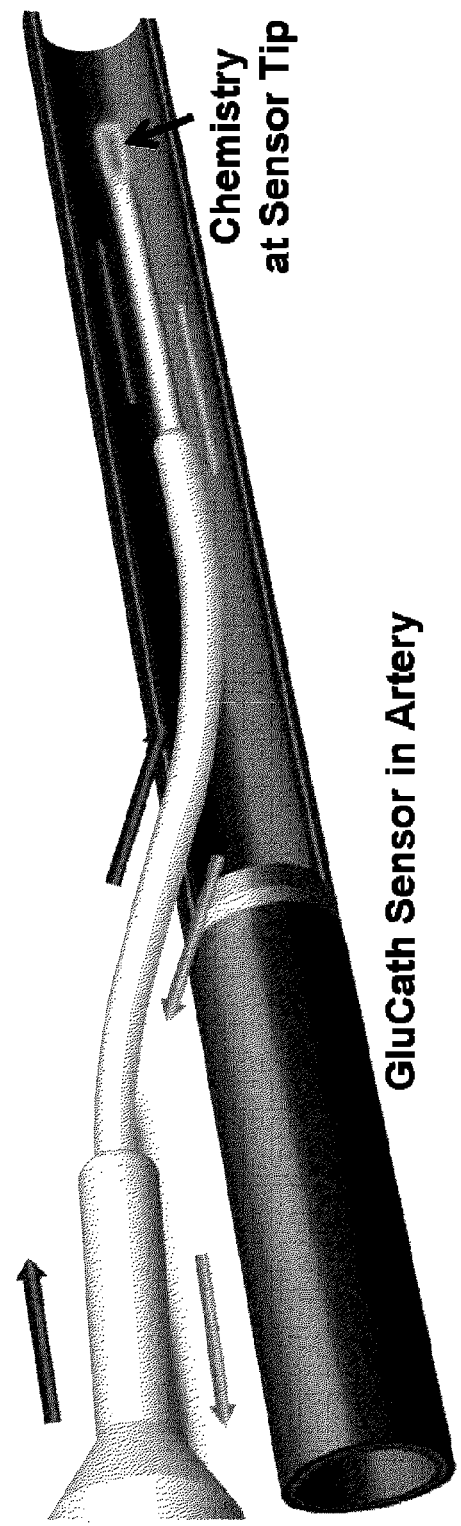
FIG. 27 illustrates an embodiment of a fluorescent sensor attached to the end an arterial catheter.

In some embodiments, a chemical sensor in which fluorescent intensity varies in response to glucose concentrations can be deployed on an optical fiber. The chemical sensor can be deployed, for example, at the tip of the sensor, although the position is not limiting. The optical fiber can be a 100 micron, 150 micron, 200 micron, 250 micron, or 300 micron fiber, although the size of the fiber is not limiting. The sensor can be, for example, 0.30, 0.40, or 0.55 mm in diameter, preferably about 0.42 mm. In some embodiments, the sensor can be inserted via a standard arterial sensor, such as a 20 Ga radial artery catheter used for pressure monitoring, as shown in FIG. 27. Blue light can travel down the optical fiber to the sensor to excite the sensor to produce green fluorescence, and the green fluorescence can travel back up the fiber, although the colors of the light are not limited. In some embodiments, glucose measurements can be taken, for example, every 1, 2, 3, 4, 5, 6, 7, 8, 9, 10, 11, 12, 13, 14, or 15 seconds for up to 12, 24, 36, 48, or 72 hours. In some embodiments, the sensor can be calibrated using one in vivo reference point, with optional daily recalibration. Additionally, the sensor can be configured to adjust for pH and/or temperature compensation.

Figure 28:
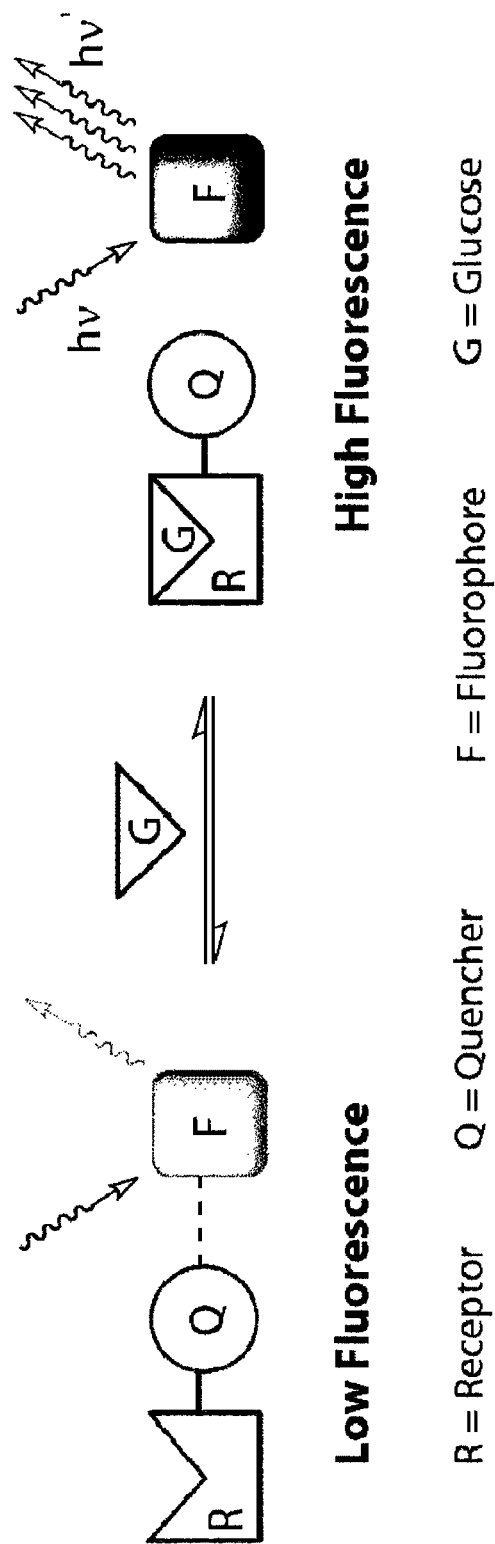
FIG. 28 shows the effect of glucose on an embodiment of a complex comprising a pyranine-based fluorophore, a boronic acid receptor, and a quencher complex.

The sensor chemistry can use a three component system (receptor, quencher and fluorophore). In some embodiments, a pyranine-based fluorophore, a boronic acid receptor, and a quencher complex can be used. In the absence of glucose, the quencher can inhibit the fluorescence of the fluorophore. In the presence of glucose, the bond between the quencher and the fluorescent dye can be changed, and the dye can emit green light when excited by, for example, blue light, in proportion to the surrounding glucose. The boronic acid receptor can form a reversible, non-enzymatic, covalent bond with glucose, and the receptor-quencher complex can be tailored for glucose selectivity. FIG. 28 illustrates an embodiment of the three component system.

Sensors using boronic acid based receptors can be configured to have sensitivity to other saccharides. In some embodiments, the receptor can use two boronic acids. This can change the molecular geometry, creating an affinity preference to bind glucose over fructose, or other saccharides.

In some embodiments, a sensor can have improved mean absolute relative difference values. Piper et al., hereby incorporated by reference in its entirety, (Piper, Hannah G. "Real-Time Continuous Glucose Monitoring in Pediatric Patients During and After Cardiac Surgery," in Pediatrics, Vol. 118, No. 3, September 2006 ("Piper")), discusses the performance characteristics of a subcutaneously implanted continuous (48 hours) glucose sensor (the "Guardian RT" from Medtronic Minimed—a glucose oxidase electrochemical sensor; no equilibrium fluorescence sensors were available then (or now)). As discussed in the article (see e.g., Statistical Analysis and Results), mean absolute relative difference ("MARD") was used to compare accuracy of the Guardian RT and reference arterial values. The overall MARD between sensor glucose values and arterial samples was 17.6%. Note, the MARD for many of the Guardian RT sensors was much higher than 17.6% (Sensor 12—MARD of 100.1%; Sensor 13—MARD of 43.2%; Sensor 14—MARD of 57.9%, etc.). The article concluded that the Guardian RT real-time subcutaneous sensor "provided clinically reliable measurement when compared with blood glucose concentrations [arterial reference values] . . . . The MARD between sensor readings and laboratory blood glucose values in this study was 17.6%, whereas other groups have reported a range between 16% and 19% (citing Goldberg et al., Diabetes Technol Ther. 2004; 6: 339-347; Guerci et al., Diabetes Care 2003; 26: 582-589; Vriesendorp et al., Diabetes Technol Ther. 2005; 7: 315-322.)" (See Discussion, $1^{st}$ sentence). Goldberg et al. is hereby incorporated by reference in its entirety.

Figure 29:
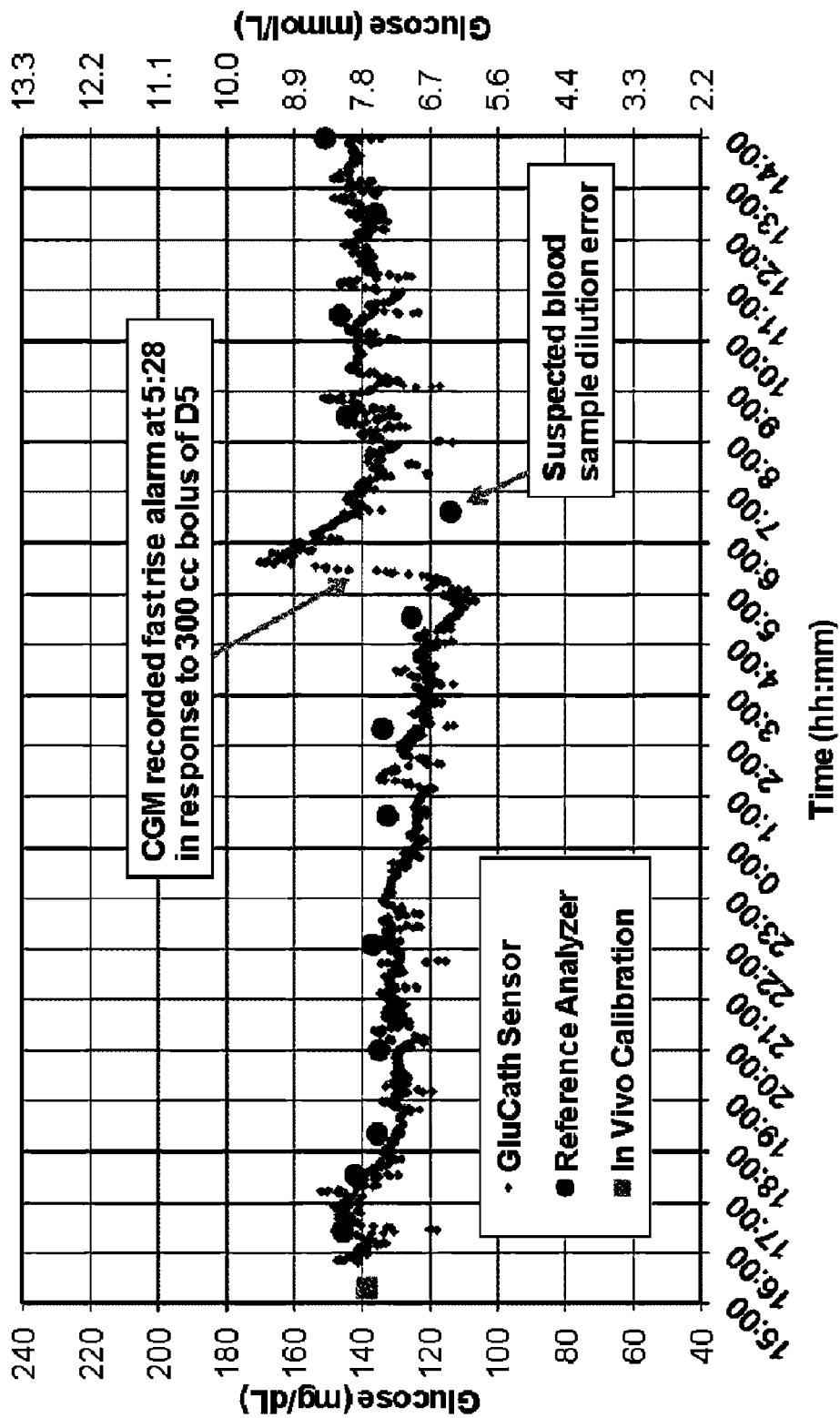
FIG. 29 shows the results initial 24 hour clinical study demonstrating the feasibility of an intra-arterial deployment of an embodiment of an analyte sensor.

FIG. 29 illustrates an initial 24 hour clinical study demonstrating the feasibility of intra-arterial deployment. As shown, the sensor has an 8.9% MARD value, illustrating its superior accuracy.

Figure 30:
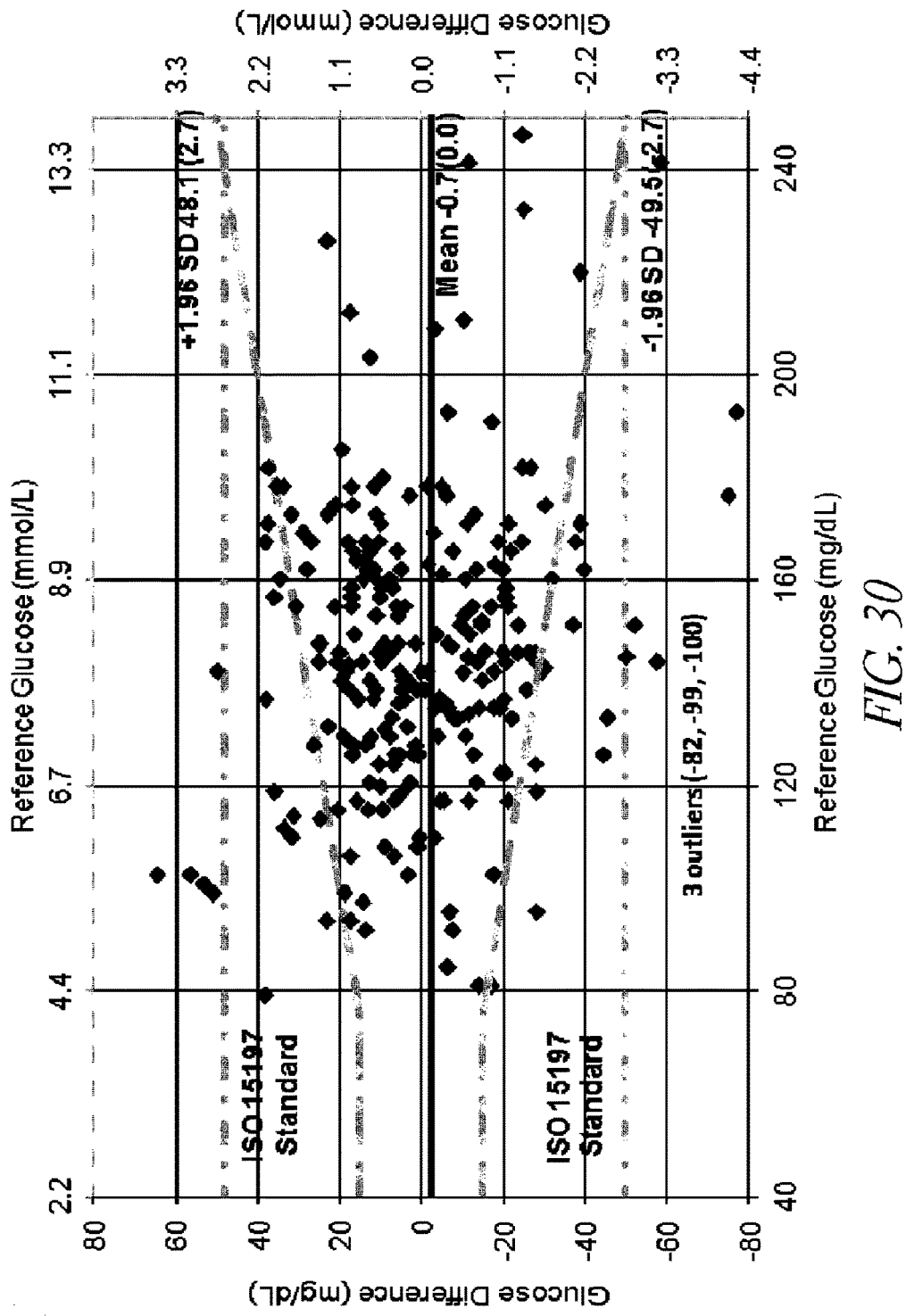
FIG. 30 shows the results of a multi-center lead-in subject experience with identified procedural and device enhancements according to an embodiment of an analyte sensor.

FIG. 30 illustrates a multi-center lead-in subject experience identifying procedural and device enhancements. Procedural enhancements can include, for example, cardiovascular surgery focus and marking time prior to sampling. Device enhancements can include extension set, securement, and temperature compensation. Additionally, as shown, the sensor can be prospectively calibrated with no filtering and no dropped points.

Figure 31A:
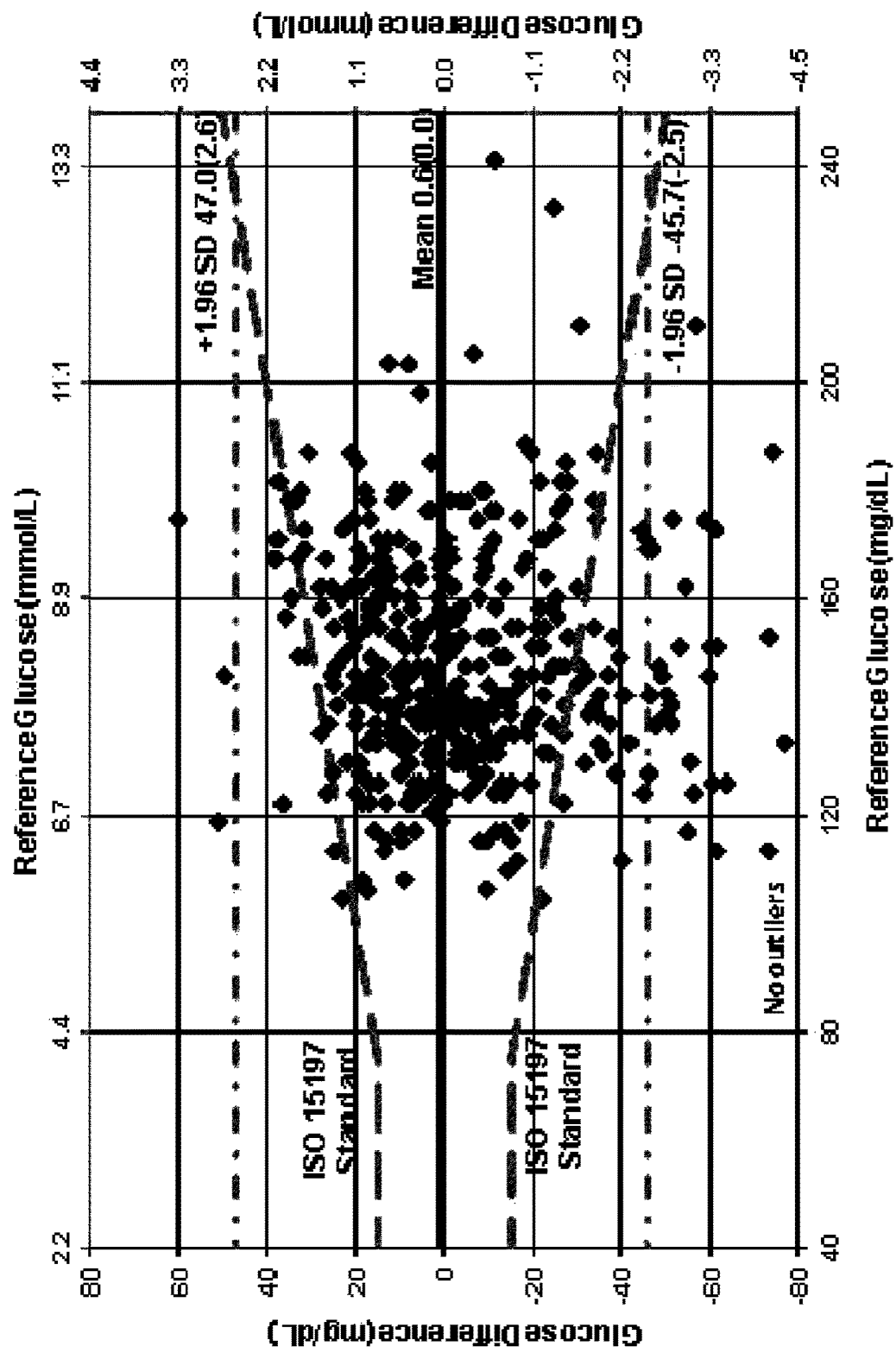
FIGS. 31A and B show a comparison between prospective and post-processed testing using an embodiment of an analyte sensor.
Figure 31B:
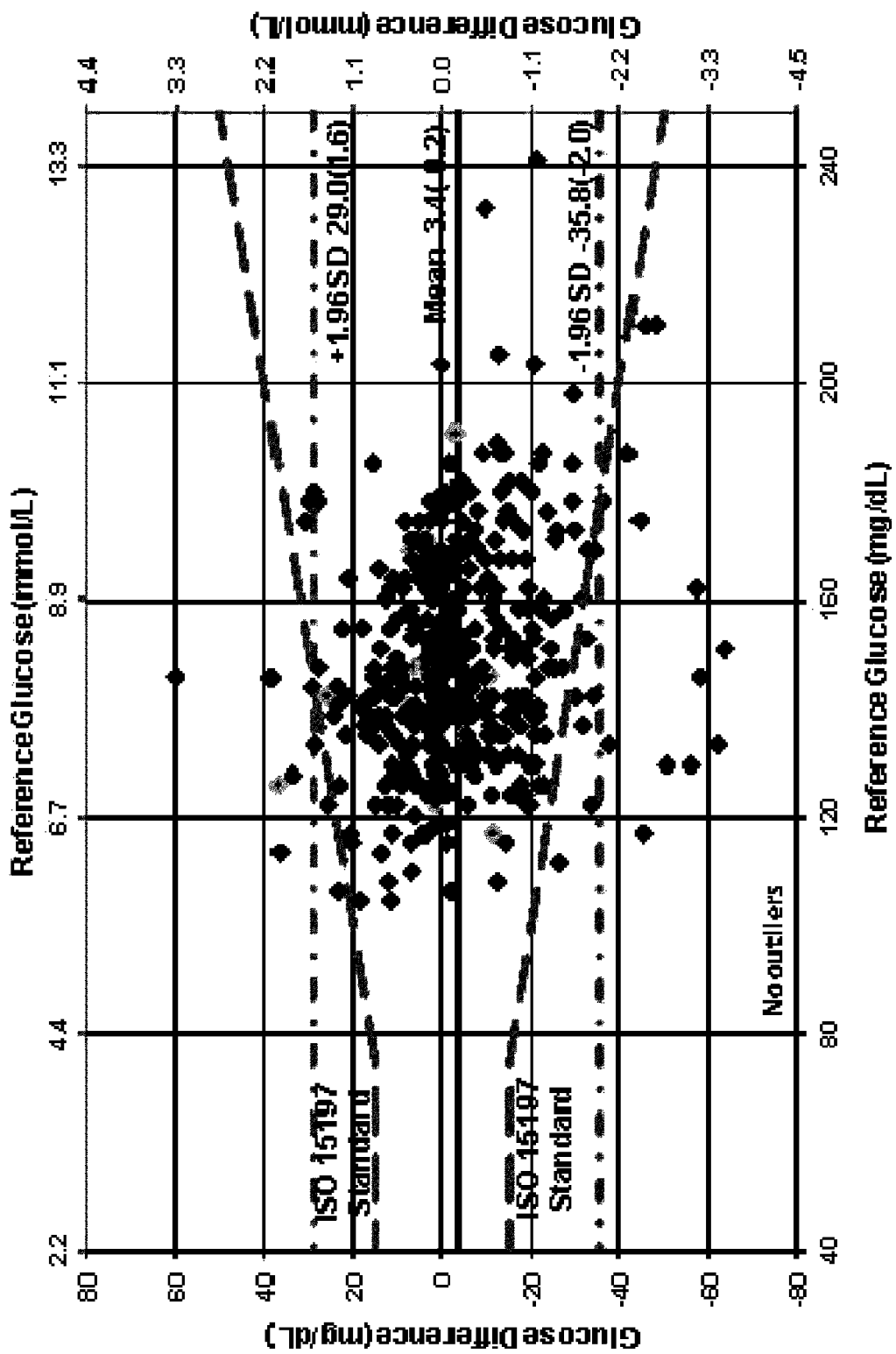

FIGS. 31A and B illustrate the back testing of measurement algorithm enhancements using post-processing methods. The figures illustrate a single site data set among 20 post-elective CV surgery subjects with 413 paired points. As shown, the prospective data in FIG. 31A has an 84% ISO and a 12.3% MARD, whereas the post-processed data has a 92% ISO and an 8.0% MARD. Excluded data included optical signal shifts (<1%), flush contamination (8%) and sensor failures (2%). The method used included reference values paired to the sensor reading immediately prior to sampling, and recalibration using enhanced algorithms for temperature and pH compensation.

Figure 32A:
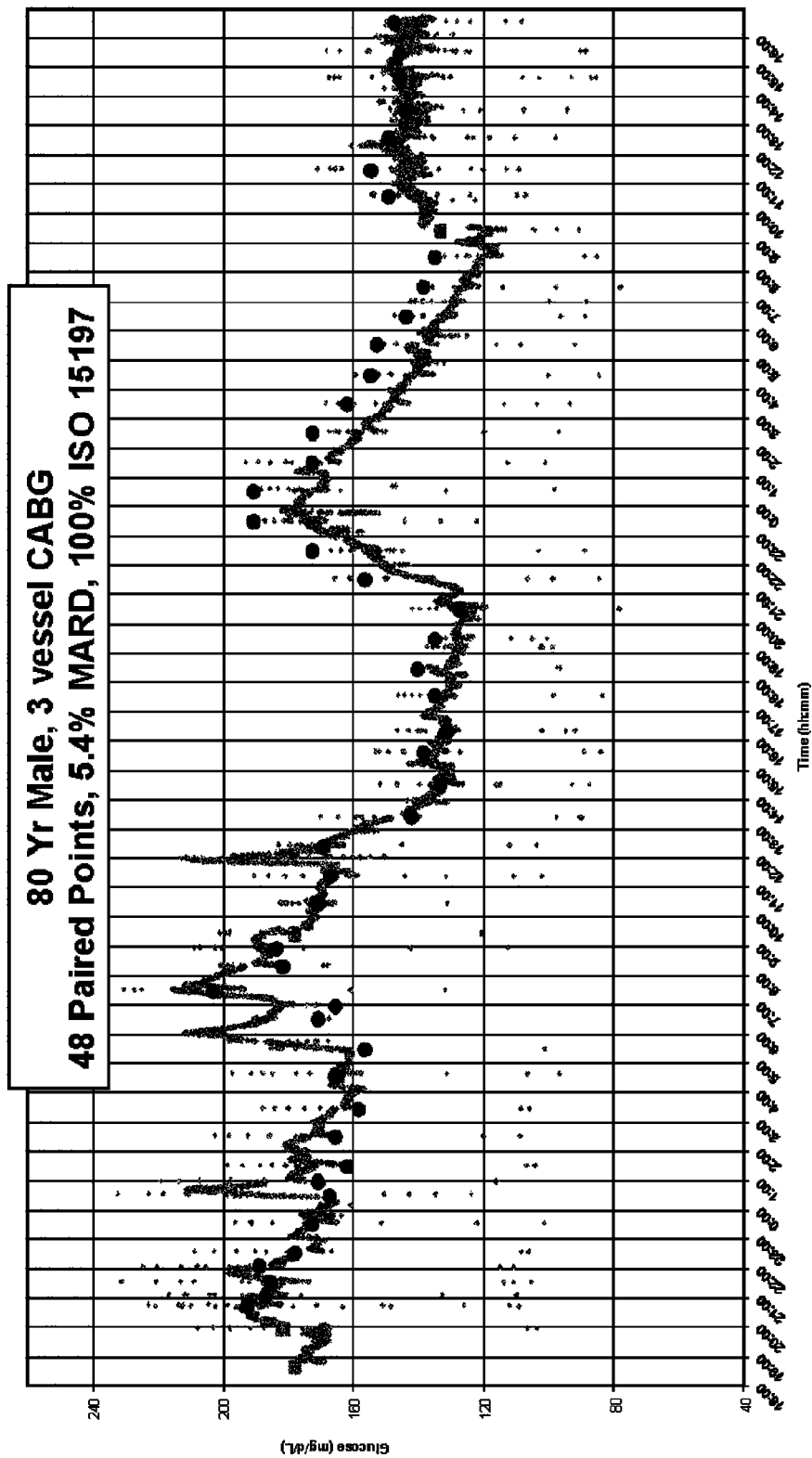
FIGS. 32A and B show the results of a clinical experience at 48 hours using an embodiment of an analyte sensor.
Figure 32B:
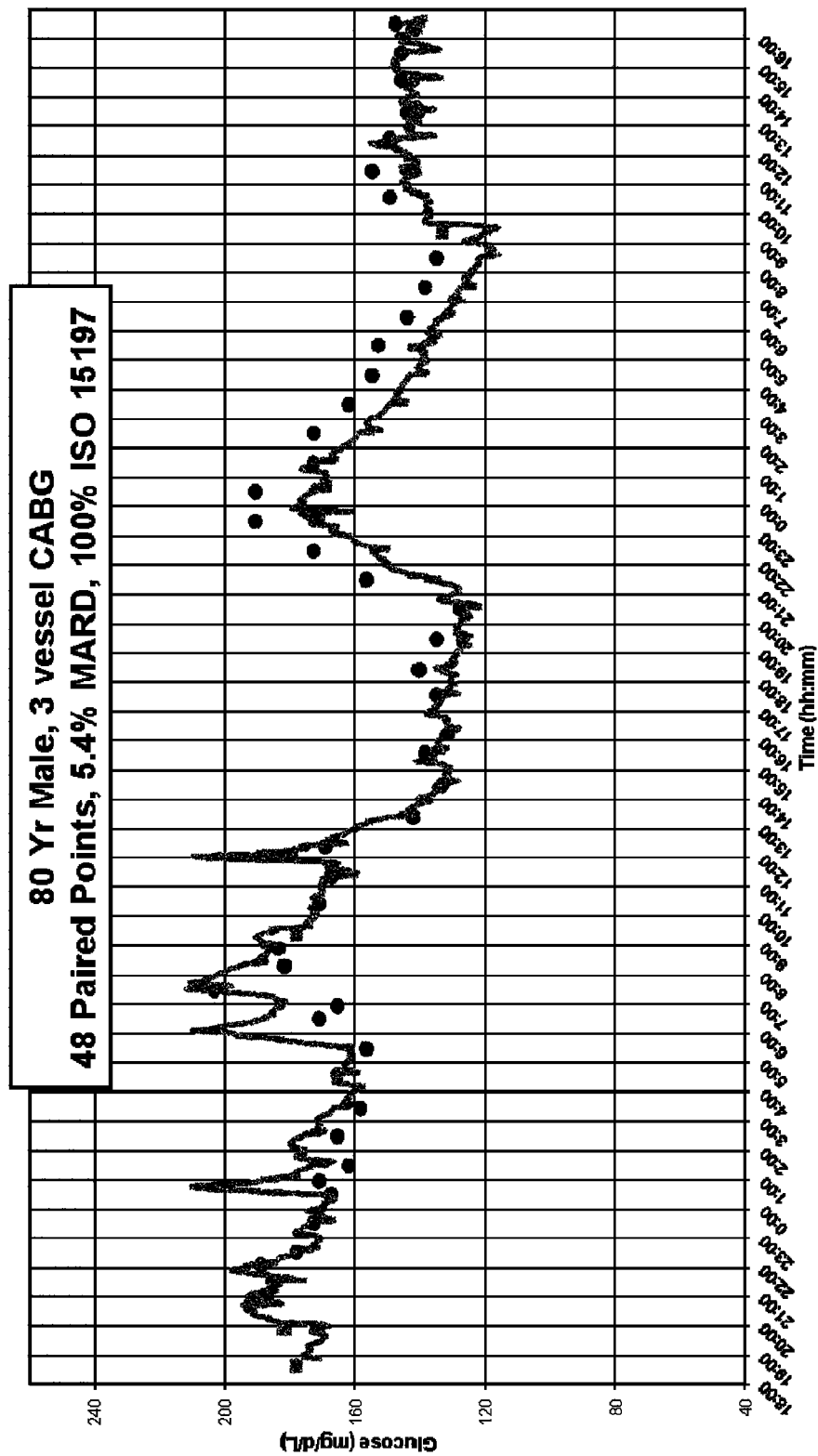

FIGS. 32A and B illustrate recent clinical experiences at 48 hours prospectively validating enhancements. FIG. 32A illustrates the results prospectively calibrated, with no filtering and no dropped points. FIG. 32B illustrates results prospectively calibrated with 5 minute averaging and no dropped points.

Figure 33:
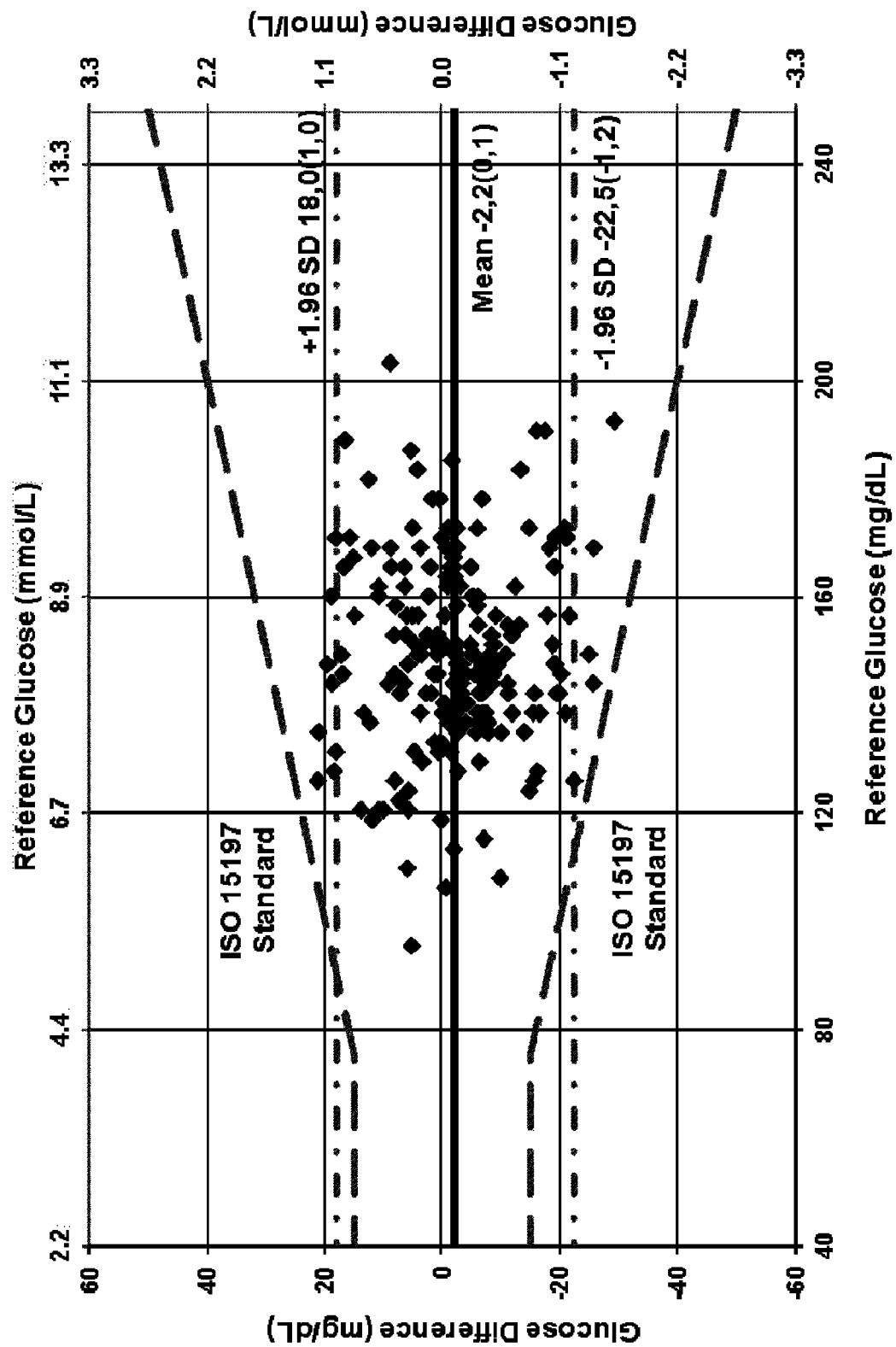
FIG. 33 shows the results of a single-site 48 hour lead-in with 5 subjects.

FIG. 33 illustrates a single-site 48 hour lead-in subject with 5 different subjects. Table I below illustrates the MARD ratings for the different subjects. The testing was prospectively calibrated, with no filtering and no dropped points.

TABLE I

| Subject | MARD |
|---|---|
| 22 | 5.6% |
| 23 | 5.4% |
| 24 | 8.5% |
| 25 | 4.0% |
| 26 | 3.9% |
| N = 5 | 5.5% |

In some embodiments of the disclosed sensor, the sensor can be truly continuous with rapid response time and can be highly selective for glucose. A single-point calibration could be used with daily recalibration. Additionally, the disclosed sensor is well-suited to critical care environments as, for example, the sensor can be inserted through radial artery catheter and the sensor is configured to be a small and portable instrument in some embodiments.

Clinical Study

Figure 34A:
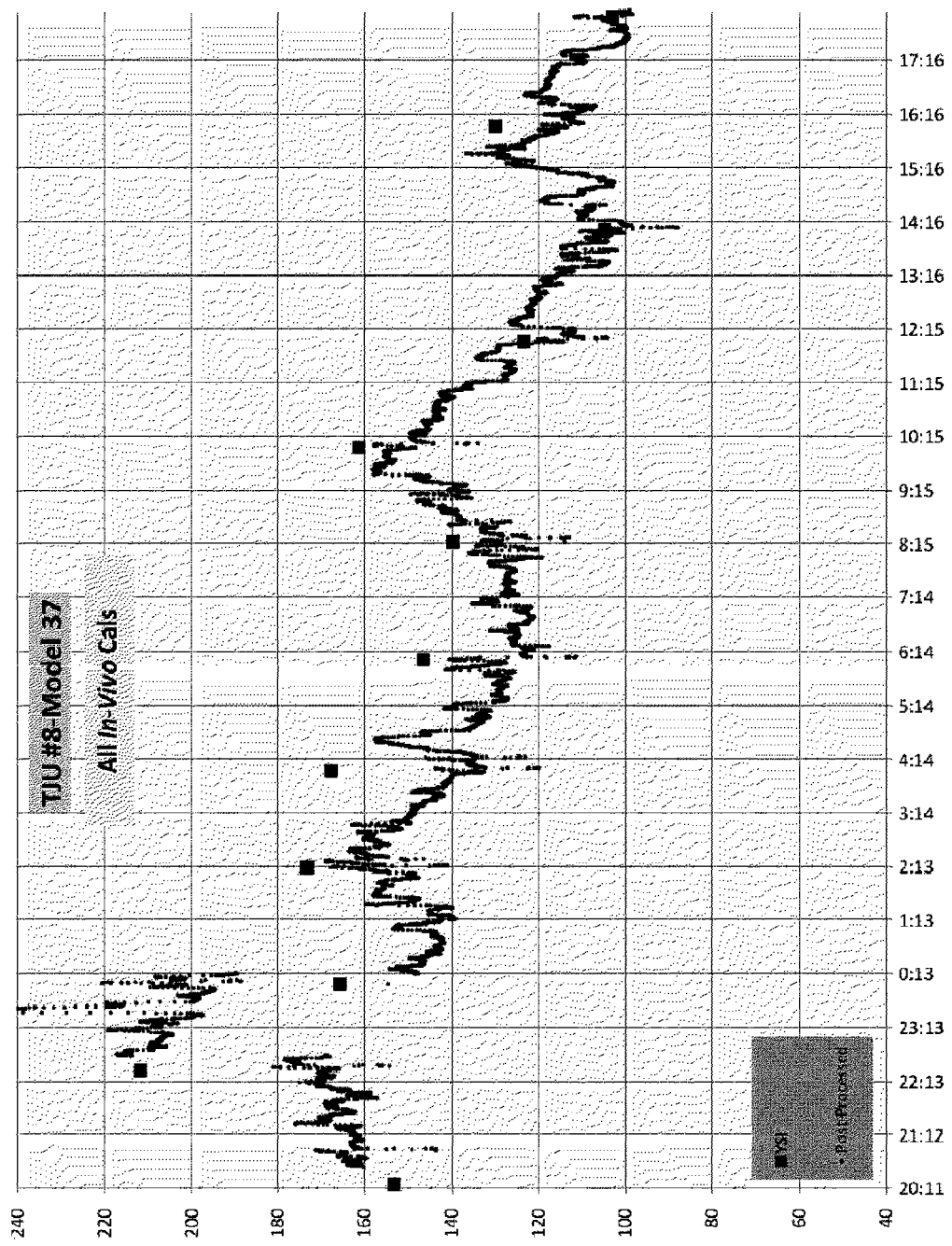
FIGS. 34A-C show the results of a study using an embodiment of a dry insertion sensors.
Figure 34B:
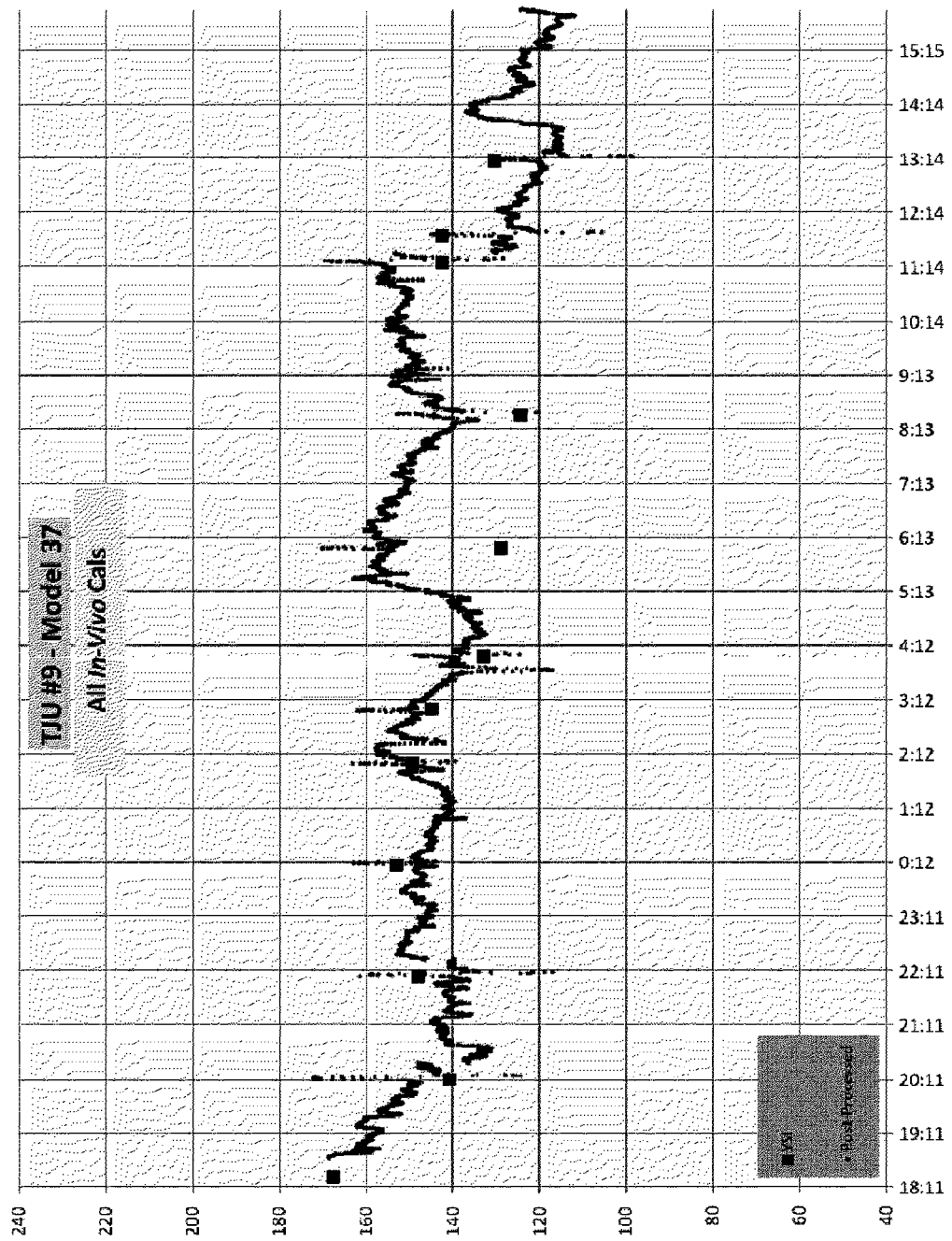
Figure 34C:
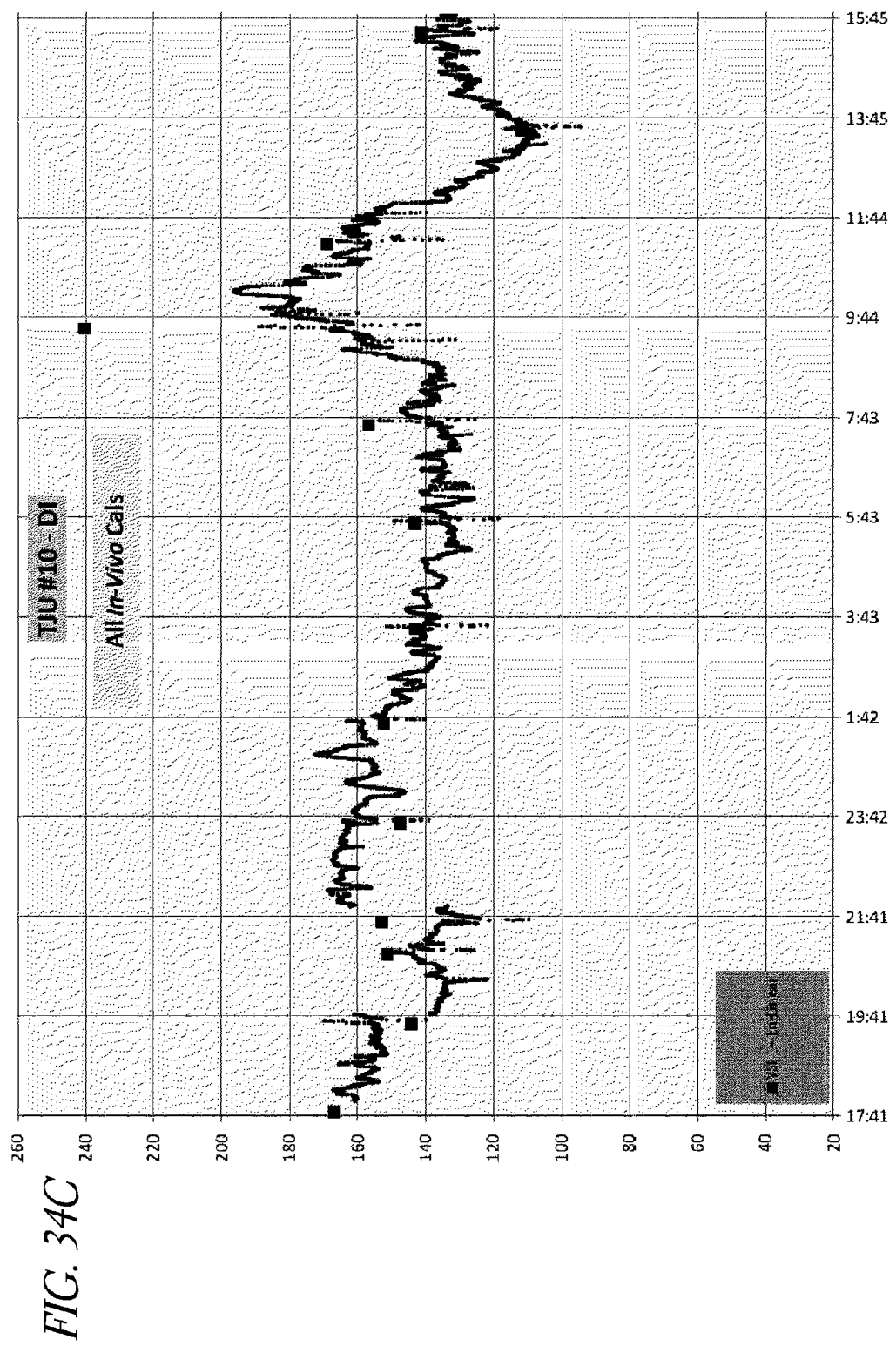

Testing was performed at Thomas Jefferson University with embodiments of the disclosed dry insertion and in vivo calibration methods. FIGS. 34A-C illustrate testing results on three different subjects. As shown, the sensors exhibited excellent MARD results, with the sensor in patient 8 resulting in a MARD of 7.7%, the sensor in patient 9 resulting in a MARD of 8.5%, and the sensor in patient 10 resulting in a MARD of 8.7%.

The sensors used to test patients 8-10 were not hydrated prior to insertion in the patients, and no Michaelis-Menten coefficients were factored in.

Table II compares the results of testing using an embodiment of the Ln-linear method disclosed above as compared to the Michaelis-Menten parameters described in U.S. Pat. Publ. Nos. 2011/0224516 and 2010/0312483, both of which are herein incorporated by reference in their entireties.

TABLE II

Clinical Test Results

| Clinical Site | Patient # | MM MARD (%) | LL MARD (%) |
|---|---|---|---|
| RNSH | 1 | 17.9 | 9.4 |
| RNSH | 2 | 8.1 | 4.9 |
| RNSH | 3 | 11.8 | 10.5 |
| RNSH | 4 | 6.9 | 3.0 |
| RNSH | 5 | 10.5 | 13.0 |
| RNSH | 6 | 9.8 | 3.4 |
| RNSH | 7 | 5.7 | 5.5 |
| RNSH | 8 | 15.5 | 12.4 |
| RNSH | 9 | 5.2 | 3.4 |
| RNSH | 10 | 6.2 | 6.2 |
| RNSH | 11 | 21.4 | 21.8 |
| RNSH | 12 | 33.4 | 32.6 |
| RNSH | 13 | 22.0 | 20.4 |
| RNSH | 14 | 12.6 | 5.4 |
| RNSH | 16 | 9.6 | 11.5 |
| RNSH | 18 | 11.4 | 12.7 |
| RNSH | 19 | 6.5 | 6.7 |
| RNSH | 20 | 13.8 | 4.5 |
| RNSH | 21 | 19.0 | 12.6 |
| RNSH | 22 | 5.7 | 4.9 |
| RNSH | 23 | 6.3 | 5.5 |
| RNSH | 24 | 8.9 | 8.1 |
| RNSH | 25 | 3.6 | 3.5 |
| RNSH | 26 | 3.6 | 4.0 |
| RNSH | 27 | 9.8 | 7.4 |
| RNSH | 28 | 7.5 | 6.9 |
| OLVG | 1 | 15.7 | 13.0 |
| OLVG | 2 | 12.9 | 14.8 |
| OLVG | 3 | 12.3 | 12.0 |
| OLVG | 4 | 15.2 | 12.9 |
| OLVG | 5 | 26.7 | 28.0 |
| TJU | 5 | 12.8 | 13.3 |
| TJU | 6 | 10.6 | 4.0 |
| TJU | 7 | 27.2 | 22.0 |
| Overall Average | | 12.5 | 10.6 |
| Average RNSH | | 11.3 | 9.2 |
| Average OLVG | | 16.6 | 16.1 |

What is claimed is:

1. A method for monitoring glucose concentration in a physiological fluid in a patient, comprising:
    providing a sensor comprising an equilibrium fluorescence chemical indicator system immobilized in a hydrogel disposed along a distal region of an optical fiber, wherein the hydrogel comprising the immobilized chemical indicator system is in a dry state;
    deploying the distal region of the optical fiber in the physiological fluid, wherein the hydrogel with immobilized chemical indicator system disposed along the distal region of the optical fiber is deployed in a dry state;
    allowing the hydrogel with immobilized chemical indicator system to hydrate in vivo in the physiological fluid;
    after in vivo hydration, performing an in vivo calibration of the fluorescent response of the immobilized chemical indicator system against an independently measured glucose concentration in the physiological fluid; and
    monitoring the glucose concentration in the physiological fluid after calibration.

2. The method of claim 1, wherein the chemical indicator system comprises a fluorophore having acid and base forms.

3. The method of claim 2, wherein the in vivo calibration is corrected based on an estimated pH of the physiological fluid.

4. The method of claim 3, wherein the pH of the physiological fluid is estimated based on a ratio of fluorescent emissions from the acid and base forms of the fluorophore.

5. The method of claim 1, further comprising measuring the temperature of the physiological fluid.

6. The method of claim 5, wherein the in vivo calibration is corrected based on the measured temperature of the physiological fluid.

7. The method of claim 1, wherein the hydrogel is hydrated for at least about 10 minutes.

8. The method of claim 1, wherein the hydrogel is hydrated for approximately 1-2 hours.

9. The method of claim 1, further comprising performing a factory calibration of the chemical indicator system against a known glucose solution and storing the factory calibration data.

10. The method of claim 1, wherein the in vivo calibration comprises applying the equation:

$$G = M*\text{Ln}(\text{Glu}) + B$$

wherein G is a fluorescence intensity of the chemical indicator system, Glu is the glucose concentration in the physiological fluid, M is the slope of the straight line approximation at calibration, and B is the intercept of the straight line approximation at calibration;

wherein G is adjusted by a calibration factor to take into account pH using the equation $$CALglu = \frac{Glucal}{\exp(\text{Ln}(glucalc))}$$

wherein CALgul is the calibration factor, Glucal is the value of the independently measured glucose concentration of the physiological sample, and Ln(glucalc) is the natural logarithm of the independently measured glucose concentration of the physiological sample.

11. The method of claim 1, wherein the in vivo calibration comprises applying the equation:

$$G = M*\text{Ln}(\text{Glu}) + B$$

wherein G is a fluorescence intensity of the chemical indicator system, Glu is the glucose concentration in the physiological fluid, M is the slope of the straight line approximation at calibration, and B is the intercept of the straight line approximation at calibration.

12. The method of claim 1, wherein the in vivo calibration is a one-point calibration.

13. A method for monitoring glucose concentration in a physiological fluid in a patient, comprising:

providing a sensor comprising an equilibrium fluorescence chemical indicator system immobilized in a hydrogel disposed along a distal region of an optical fiber, wherein the hydrogel comprising the immobilized chemical indicator system is in a dry state;

deploying the distal region of the optical fiber in the physiological fluid without performing ex vivo calibration, wherein the hydrogel with immobilized chemical indicator system disposed along the distal region of the optical fiber is deployed in a dry state;

allowing the hydrogel with immobilized chemical indicator system to hydrate in vivo in the physiological fluid for at least 10 minutes;

after in vivo hydration, performing a one-point in vivo calibration of the fluorescent response of the immobilized chemical indicator system against an independently measured glucose concentration in the physiological fluid; and monitoring the glucose concentration in the physiological fluid after calibration.

14. The method of claim 13, wherein the one-point in vivo calibration comprises applying the equation:

$G = M^* \text{Ln}(\text{Glu}) + B$ wherein G is a fluorescence intensity of the chemical indicator system, Glu is the glucose concentration in the physiological fluid, M is the slope of the straight line approximation at calibration, and B is the intercept of the straight line approximation at calibration.

15. The method of claim 14, wherein G is adjusted by a calibration factor to take into account pH using the equation $$CALglu = \frac{Glucal}{\exp(\text{Ln}(glucalc))}$$

wherein CALglu is the calibration factor, Glucal is the value of the independently measured glucose concentration of the physiological sample, and Ln(glucalc) is the natural logarithm of the independently measured glucose concentration of the physiological sample.

16. The method of claim 13, wherein the hydrogel is hydrated for approximately 1-2 hours.

* * * * *